US008778021B2

(12) United States Patent
Cartledge

(10) Patent No.: US 8,778,021 B2
(45) Date of Patent: Jul. 15, 2014

(54) POST-OPERATIVE ADJUSTMENT TOOL, MINIMALLY INVASIVE ATTACHMENT APPARATUS, AND ADJUSTABLE TRICUSPID RING

(75) Inventor: Richard G. Cartledge, Boca Raton, FL (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

(21) Appl. No.: 12/875,464

(22) Filed: Sep. 3, 2010
(Under 37 CFR 1.47)

(65) Prior Publication Data
US 2011/0196480 A1    Aug. 11, 2011

Related U.S. Application Data

(63) Continuation of application No. 12/692,415, filed on Jan. 22, 2010.

(60) Provisional application No. 61/146,560, filed on Jan. 22, 2009, provisional application No. 61/157,649, filed on Mar. 5, 2009.

(51) Int. Cl.
A61B 17/08        (2006.01)

(52) U.S. Cl.
USPC .................. 623/2.37; 623/2.36; 623/2.11

(58) Field of Classification Search
USPC ............................................. 623/1.37, 2.37
See application file for complete search history.

(56) References Cited

U.S. PATENT DOCUMENTS

| 4,042,979 A | 8/1977 | Angell |
| 4,489,446 A | 12/1984 | Reed |
| 4,602,911 A | 7/1986 | Ahmadi et al. |
| 4,676,253 A | 6/1987 | Newman et al. |
| 5,064,431 A | 11/1991 | Gilbertson et al. |
| 5,102,417 A | 4/1992 | Palmaz |
| 5,119,674 A | 6/1992 | Nielsen |
| 5,201,880 A | 4/1993 | Wright et al. |
| 5,243,976 A | 9/1993 | Ferek-Petric et al. |
| 5,306,296 A | 4/1994 | Wright et al. |
| 5,405,378 A | 4/1995 | Strecker |

(Continued)

FOREIGN PATENT DOCUMENTS

| EP | 0495417 A1 | 7/1992 |
| EP | 1 554 990 A2 | 7/2005 |

(Continued)

OTHER PUBLICATIONS

U.S. Appl. No. 13/123,768.

(Continued)

Primary Examiner — Melanie Tyson
Assistant Examiner — Todd J Scherbel
(74) Attorney, Agent, or Firm — Lerner, David, Littenberg, Krumholz & Mentlik, LLP

(57) ABSTRACT

An implantable device system for controlling the dimensions of internal anatomic passages corrects physiologic dysfunctions resulting from a structural lumen which is either too large or too small. Implantable devices are disclosed which employ various mechanisms for adjusting and maintaining the size of an orifice to which they are attached. Systems permit the implants to be implanted using minimally invasive procedures and permit final adjustments to the dimensions of the implants after the resumption of normal flow of anatomic fluids in situ.

13 Claims, 41 Drawing Sheets

(56) References Cited

U.S. PATENT DOCUMENTS

| | | |
|---|---|---|
| 5,411,552 A | 5/1995 | Andersen et al. |
| 5,423,851 A | 6/1995 | Samuels |
| 5,443,477 A | 8/1995 | Marin et al. |
| 5,522,884 A | 6/1996 | Wright |
| 5,593,424 A | 1/1997 | Northrup, III |
| 5,601,604 A | 2/1997 | Vincent |
| 5,674,279 A | 10/1997 | Wright et al. |
| 5,709,695 A | 1/1998 | Northrup, III |
| 5,709,701 A | 1/1998 | Parodi |
| 5,713,951 A | 2/1998 | Garrison et al. |
| 5,769,812 A | 6/1998 | Stevens et al. |
| 5,814,097 A | 9/1998 | Sterman et al. |
| 5,824,055 A | 10/1998 | Spiridigliozzi et al. |
| 5,908,435 A | 6/1999 | Samuels |
| 5,961,539 A | 10/1999 | Northrup, III et al. |
| 5,972,030 A | 10/1999 | Garrison et al. |
| 5,984,959 A | 11/1999 | Robertson et al. |
| 5,989,284 A | 11/1999 | Laufer |
| 6,067,991 A | 5/2000 | Forsell |
| 6,110,200 A | 8/2000 | Hinnenkamp |
| 6,152,144 A | 11/2000 | Lesh et al. |
| 6,168,616 B1 | 1/2001 | Brown, III |
| 6,168,816 B1 | 1/2001 | Hammond |
| 6,187,040 B1 | 2/2001 | Wright |
| 6,217,610 B1 | 4/2001 | Carpentier et al. |
| 6,231,561 B1 | 5/2001 | Frazier et al. |
| 6,245,012 B1 | 6/2001 | Kleshinski |
| 6,269,819 B1 | 8/2001 | Oz et al. |
| 6,355,030 B1 | 3/2002 | Aldrich et al. |
| 6,368,348 B1 | 4/2002 | Gabbay |
| 6,402,781 B1 | 6/2002 | Langberg et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,464,707 B1 | 10/2002 | Bjerken |
| 6,470,892 B1 | 10/2002 | Forsell |
| 6,514,265 B2 | 2/2003 | Ho et al. |
| 6,524,338 B1 | 2/2003 | Gundry |
| 6,537,314 B2 | 3/2003 | Langberg et al. |
| 6,547,801 B1 | 4/2003 | Dargent et al. |
| 6,551,332 B1 | 4/2003 | Nguyen et al. |
| 6,564,805 B2 | 5/2003 | Garrison et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,629,534 B1 | 10/2003 | St. Goar et al. |
| 6,641,593 B1 | 11/2003 | Schaller et al. |
| 6,651,671 B1 | 11/2003 | Donlon et al. |
| 6,689,164 B1 | 2/2004 | Seguin |
| 6,706,065 B2 | 3/2004 | Langberg et al. |
| 6,709,456 B2 | 3/2004 | Langberg et al. |
| 6,716,243 B1 | 4/2004 | Colvin et al. |
| 6,723,038 B1 | 4/2004 | Schroeder et al. |
| 6,749,630 B2 | 6/2004 | McCarthy et al. |
| 6,767,362 B2 | 7/2004 | Schreck |
| 6,776,789 B2 | 8/2004 | Bryant et al. |
| 6,790,229 B1 | 9/2004 | Berreklouw |
| 6,793,673 B2 | 9/2004 | Kowalsky et al. |
| 6,797,002 B2 | 9/2004 | Spence et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 6,840,246 B2 | 1/2005 | Downing |
| 6,872,223 B2 | 3/2005 | Roberts et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,911,035 B1 | 6/2005 | Blomme |
| 6,921,407 B2 | 7/2005 | Nguyen et al. |
| 6,926,715 B1 | 8/2005 | Hauck et al. |
| 6,932,838 B2 | 8/2005 | Schwartz et al. |
| 6,942,694 B2 | 9/2005 | Liddicoat et al. |
| 6,974,476 B2 | 12/2005 | McGuckin, Jr. et al. |
| 6,986,738 B2 | 1/2006 | Glukhovsky et al. |
| 6,989,028 B2 | 1/2006 | Lashinski et al. |
| 7,011,082 B2 | 3/2006 | Husges |
| 7,011,682 B2 * | 3/2006 | Lashinski et al. ............ 623/2.37 |
| 7,097,658 B2 | 8/2006 | Oktay |
| 7,169,141 B2 | 1/2007 | Brock et al. |
| 7,175,660 B2 | 2/2007 | Cartledge et al. |
| 7,179,225 B2 | 2/2007 | Shluzas et al. |
| 7,220,237 B2 | 5/2007 | Gannoe et al. |
| 7,258,701 B2 | 8/2007 | Aram et al. |
| 7,297,150 B2 | 11/2007 | Cartledge et al. |
| 7,329,280 B2 | 2/2008 | Bolling et al. |
| 7,361,190 B2 | 4/2008 | Shaoulian et al. |
| 7,377,916 B2 | 5/2008 | Rudko et al. |
| 7,381,219 B2 | 6/2008 | Salahieh et al. |
| 7,442,207 B2 | 10/2008 | Rafiee |
| 7,455,690 B2 | 11/2008 | Cartledge et al. |
| 7,527,647 B2 | 5/2009 | Spence |
| 7,655,040 B2 * | 2/2010 | Douk et al. ................... 623/2.11 |
| 7,666,204 B2 | 2/2010 | Thornton et al. |
| 7,815,676 B2 | 10/2010 | Greenberg |
| 7,842,098 B2 | 11/2010 | Rioux et al. |
| 8,226,707 B2 | 7/2012 | White |
| 8,236,049 B2 | 8/2012 | Rowe et al. |
| 8,449,605 B2 | 5/2013 | Lichtenstein et al. |
| 8,470,023 B2 | 6/2013 | Eidenschink et al. |
| 2001/0021874 A1 | 9/2001 | Carpentier et al. |
| 2001/0049558 A1 | 12/2001 | Liddicoat et al. |
| 2002/0007222 A1 | 1/2002 | Desai |
| 2002/0095175 A1 | 7/2002 | Brock et al. |
| 2002/0128708 A1 | 9/2002 | Northrup et al. |
| 2002/0151961 A1 | 10/2002 | Lashinski et al. |
| 2002/0151967 A1 | 10/2002 | Mikus et al. |
| 2002/0173841 A1 * | 11/2002 | Ortiz et al. ................... 623/2.11 |
| 2003/0018358 A1 | 1/2003 | Saadat |
| 2003/0040791 A1 | 2/2003 | Oktay |
| 2003/0050649 A1 | 3/2003 | Brock et al. |
| 2003/0050693 A1 | 3/2003 | Quijano et al. |
| 2003/0074012 A1 | 4/2003 | Nguyen et al. |
| 2003/0083742 A1 | 5/2003 | Spence et al. |
| 2003/0093148 A1 | 5/2003 | Bolling et al. |
| 2003/0130730 A1 | 7/2003 | Cohn et al. |
| 2003/0199974 A1 | 10/2003 | Lee et al. |
| 2003/0233142 A1 | 12/2003 | Morales et al. |
| 2004/0011365 A1 | 1/2004 | Govari et al. |
| 2004/0019378 A1 | 1/2004 | Hlavka et al. |
| 2004/0030382 A1 | 2/2004 | St. Goar et al. |
| 2004/0068276 A1 | 4/2004 | Golden et al. |
| 2004/0088047 A1 | 5/2004 | Spence et al. |
| 2004/0111099 A1 | 6/2004 | Nguyen et al. |
| 2004/0127980 A1 | 7/2004 | Kowalsky et al. |
| 2004/0133147 A1 | 7/2004 | Woo |
| 2004/0138744 A1 | 7/2004 | Lashinski et al. |
| 2004/0148019 A1 | 7/2004 | Vidlund et al. |
| 2004/0148021 A1 | 7/2004 | Cartledge et al. |
| 2004/0153144 A1 | 8/2004 | Seguin |
| 2004/0153147 A1 | 8/2004 | Mathis |
| 2004/0161611 A1 | 8/2004 | Mueller et al. |
| 2004/0162611 A1 | 8/2004 | Marquez |
| 2004/0172046 A1 | 9/2004 | Hlavka et al. |
| 2004/0176840 A1 | 9/2004 | Langberg et al. |
| 2004/0181238 A1 | 9/2004 | Zarbatany et al. |
| 2004/0186566 A1 | 9/2004 | Hindrichs et al. |
| 2004/0193191 A1 | 9/2004 | Starksen et al. |
| 2004/0204760 A1 | 10/2004 | Fitz et al. |
| 2004/0225353 A1 | 11/2004 | McGuckin et al. |
| 2004/0243153 A1 | 12/2004 | Liddicoat et al. |
| 2004/0249453 A1 | 12/2004 | Cartledge et al. |
| 2005/0060030 A1 | 3/2005 | Lashinski et al. |
| 2005/0065550 A1 | 3/2005 | Starksen et al. |
| 2005/0070999 A1 | 3/2005 | Spence |
| 2005/0075736 A1 | 4/2005 | Collazo |
| 2005/0107886 A1 | 5/2005 | Crabtree et al. |
| 2005/0119734 A1 | 6/2005 | Spence et al. |
| 2005/0119735 A1 | 6/2005 | Spence et al. |
| 2005/0131533 A1 | 6/2005 | Alfieri et al. |
| 2005/0143766 A1 | 6/2005 | Bachmann et al. |
| 2005/0149114 A1 | 7/2005 | Cartledge et al. |
| 2005/0192601 A1 | 9/2005 | Demarais |
| 2005/0216079 A1 | 9/2005 | MaCoviak |
| 2005/0222678 A1 | 10/2005 | Lashinski et al. |

(56) References Cited

U.S. PATENT DOCUMENTS

| | | |
|---|---|---|
| 2006/0074485 A1 | 4/2006 | Realyvasquez |
| 2006/0100697 A1 | 5/2006 | Casanova |
| 2006/0106405 A1 | 5/2006 | Fann et al. |
| 2006/0135964 A1 | 6/2006 | Vesely |
| 2006/0241748 A1 | 10/2006 | Lee et al. |
| 2007/0016287 A1 | 1/2007 | Cartledge et al. |
| 2007/0051377 A1* | 3/2007 | Douk et al. ............. 128/897 |
| 2007/0118215 A1 | 5/2007 | Moaddeb |
| 2007/0233239 A1 | 10/2007 | Navia et al. |
| 2007/0244556 A1 | 10/2007 | Rafiee et al. |
| 2007/0250160 A1 | 10/2007 | Rafiee |
| 2007/0299543 A1 | 12/2007 | Cartledge et al. |
| 2008/0004697 A1 | 1/2008 | Lichtenstein et al. |
| 2008/0027483 A1 | 1/2008 | Cartledge et al. |
| 2008/0109076 A1 | 5/2008 | Cartledge et al. |
| 2008/0306586 A1 | 12/2008 | Cartledge et al. |
| 2009/0005760 A1* | 1/2009 | Cartledge et al. ............. 604/534 |
| 2009/0054974 A1 | 2/2009 | McGuckin, Jr. et al. |
| 2009/0062825 A1 | 3/2009 | Pool et al. |
| 2009/0125102 A1 | 5/2009 | Cartledge et al. |
| 2009/0210052 A1 | 8/2009 | Forster et al. |
| 2009/0234404 A1 | 9/2009 | Fitzgerald et al. |
| 2009/0248148 A1 | 10/2009 | Shaolian et al. |
| 2010/0161047 A1 | 6/2010 | Cabiri |
| 2010/0168835 A1 | 7/2010 | Dorn |
| 2010/0211166 A1 | 8/2010 | Miller et al. |
| 2010/0217385 A1 | 8/2010 | Thompson et al. |
| 2010/0305609 A1 | 12/2010 | Cartledge et al. |
| 2010/0331949 A1 | 12/2010 | Habib |
| 2011/0009956 A1 | 1/2011 | Cartledge et al. |
| 2011/0022168 A1* | 1/2011 | Cartledge ............. 623/2.37 |
| 2011/0066231 A1 | 3/2011 | Cartledge et al. |
| 2011/0093060 A1* | 4/2011 | Cartledge et al. ............. 623/1.15 |
| 2011/0093062 A1* | 4/2011 | Cartledge et al. ............. 623/2.11 |
| 2011/0118828 A1 | 5/2011 | Thompson |
| 2011/0202130 A1 | 8/2011 | Cartledge et al. |
| 2011/0208283 A1 | 8/2011 | Rust |
| 2011/0208295 A1 | 8/2011 | Cartledge et al. |
| 2011/0257633 A1 | 10/2011 | Cartledge et al. |
| 2011/0257737 A1 | 10/2011 | Fogarty et al. |
| 2011/0264191 A1 | 10/2011 | Rothstein |
| 2012/0022633 A1 | 1/2012 | Olson et al. |
| 2012/0022640 A1 | 1/2012 | Gross et al. |
| 2012/0059458 A1 | 3/2012 | Buchbinder et al. |
| 2012/0123531 A1* | 5/2012 | Tsukashima et al. ........ 623/2.37 |
| 2012/0136436 A1 | 5/2012 | Cabiri et al. |
| 2012/0158115 A9 | 6/2012 | Arnault De La Menardiere et al. |
| 2012/0197379 A1 | 8/2012 | Laske et al. |
| 2012/0277842 A1 | 11/2012 | Kunis |
| 2013/0006352 A1 | 1/2013 | Yaron |
| 2013/0144371 A1 | 6/2013 | Kavteladze |
| 2013/0172977 A1 | 7/2013 | Forde et al. |

FOREIGN PATENT DOCUMENTS

| | | |
|---|---|---|
| EP | 1611868 A2 | 1/2006 |
| JP | 61013818 | 1/1986 |
| JP | 05-049655 | 3/1993 |
| JP | 10-503399 A | 3/1998 |
| JP | 3049359 B2 | 6/2000 |
| JP | 3180136 B2 | 4/2001 |
| JP | 3180136 B2 | 6/2001 |
| JP | 2002509448 A | 3/2002 |
| JP | 2002523172 A | 7/2002 |
| JP | 2002526194 A | 8/2002 |
| JP | 2003533275 A | 11/2003 |
| JP | 2004535851 A | 12/2004 |
| JP | 2005537067 A | 12/2005 |
| JP | 2006507104 A | 3/2006 |
| JP | 2006520651 A | 9/2006 |
| JP | 2006520670 A | 9/2006 |
| WO | 9101697 A1 | 2/1991 |
| WO | 9315690 A2 | 8/1993 |
| WO | 9603938 A1 | 2/1996 |
| WO | 97/16135 A1 | 5/1997 |
| WO | 9719655 A1 | 6/1997 |
| WO | 99/04730 A1 | 2/1999 |
| WO | 99/30647 A1 | 6/1999 |
| WO | 9960952 A1 | 12/1999 |
| WO | 00/03759 A2 | 1/2000 |
| WO | 0015158 A1 | 3/2000 |
| WO | 0016700 A1 | 3/2000 |
| WO | 01/26586 A1 | 4/2001 |
| WO | 01 50985 A1 | 7/2001 |
| WO | 2004/012583 A2 | 2/2004 |
| WO | 2004/019816 A2 | 3/2004 |
| WO | 2004019826 A1 | 3/2004 |
| WO | 2004047677 A2 | 6/2004 |
| WO | 2004/060217 A1 | 7/2004 |
| WO | 2004080336 A2 | 9/2004 |
| WO | 2004/112585 A2 | 12/2004 |
| WO | 2004/112651 A2 | 12/2004 |
| WO | 2004/112658 A1 | 12/2004 |
| WO | 2005/007036 A1 | 1/2005 |
| WO | 2005/007037 A1 | 1/2005 |
| WO | 2005/007219 A2 | 1/2005 |
| WO | 2005009285 | 2/2005 |
| WO | 2005/025644 A2 | 3/2005 |
| WO | 2005/046488 A2 | 5/2005 |
| WO | 2005/055883 A1 | 6/2005 |
| WO | 2005/062931 A2 | 7/2005 |
| WO | 2005084592 A2 | 9/2005 |
| WO | 2006/105084 A2 | 10/2006 |
| WO | 2007/136783 A2 | 11/2007 |
| WO | 2008/085814 A2 | 7/2008 |
| WO | 2009/052509 A1 | 4/2009 |
| WO | 2010/085649 A1 | 7/2010 |
| WO | 2010/085659 A1 | 7/2010 |

OTHER PUBLICATIONS

Extended European Search Report for Application No. 10733913 dated Dec. 11, 2012.
Letter dated Jan. 27, 2011 from Richard H. Levinstein, Esq.
Extended European Search Report for Application No. EP13166640 dated Jul. 1, 2013.

* cited by examiner

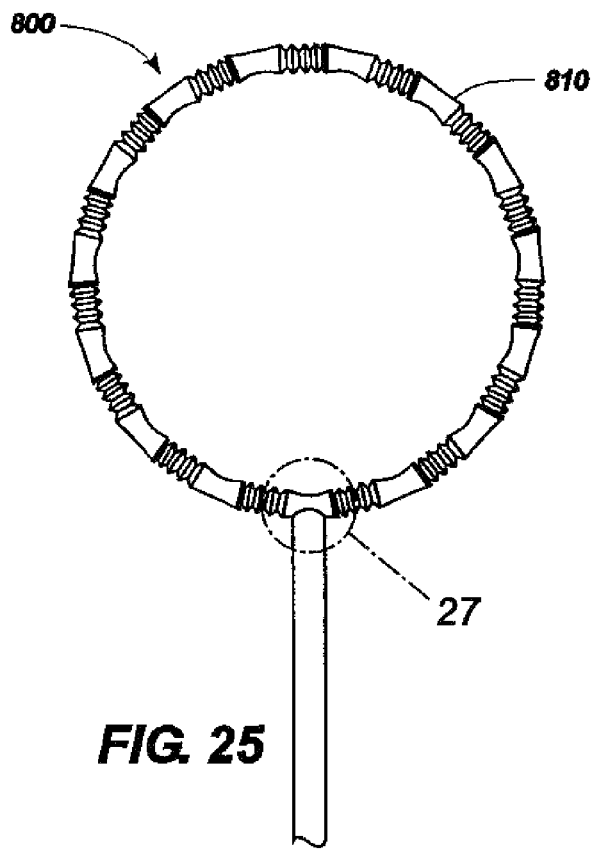
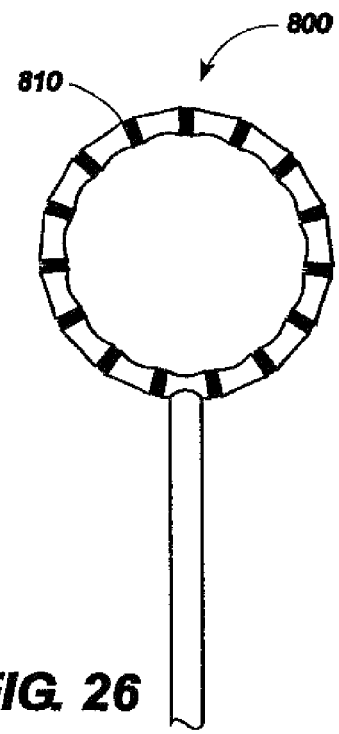
FIG. 25
FIG. 26
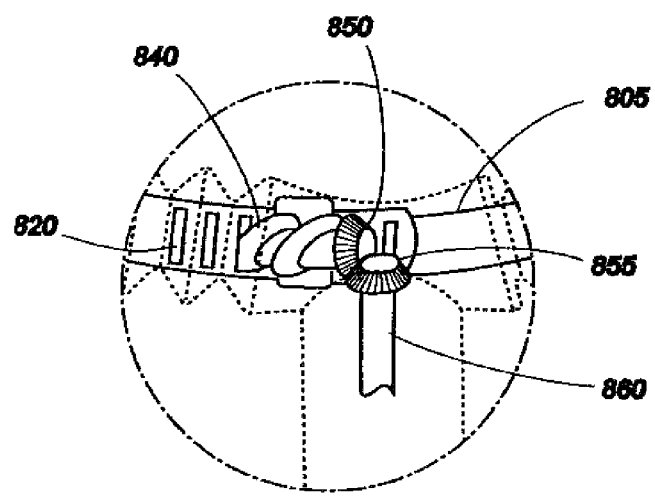
FIG. 27

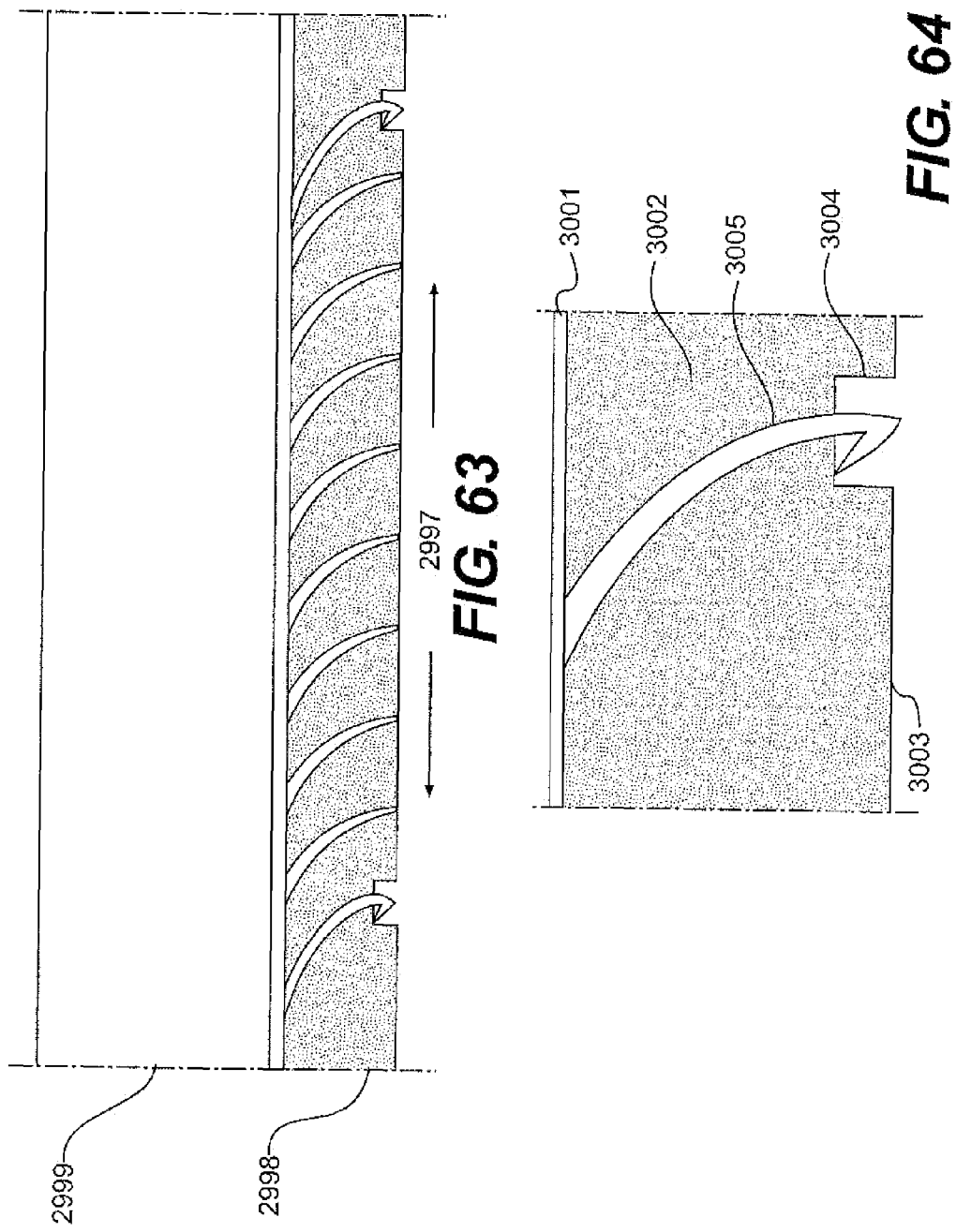

POST-OPERATIVE ADJUSTMENT TOOL, MINIMALLY INVASIVE ATTACHMENT APPARATUS, AND ADJUSTABLE TRICUSPID RING

CROSS REFERENCE TO RELATED APPLICATIONS

This application is a continuation of U.S. patent application Ser. No. 12/692,415, filed Jan. 22, 2010, which claims priority to U.S. Provisional Patent Application No. 61/146,560, filed Jan. 22, 2009; and U.S. Provisional Patent Application No. 61/157,649, filed Mar. 5, 2009, all of which are hereby incorporated by reference.

STATEMENT REGARDING SPONSORED RESEARCH OR DEVELOPMENT

Not Applicable.

BACKGROUND OF THE INVENTION

1. Field of the Invention

This invention relates generally to implantable devices for controlling at least one of shape and size of an anatomic structure or lumen.

2. Description of Related Art

There is often a need to reduce the internal circumference of an orifice or other open anatomic structure to narrow or increase the size of the orifice or opening to achieve a desired physiologic effect. Often, such surgical procedures require interruption in the normal physiologic flow of blood, other physiologic fluids, or other structural contents through the orifice or structure. The exact amount of the narrowing or widening required for the desired effect often cannot be fully appreciated until physiologic flow through the orifice or structure is resumed. It would be advantageous, therefore, to have an adjustable means of achieving the narrowing or widening effect, such that the degree of narrowing or widening could be changed after its implantation, and after the resumption of normal flow in situ.

One example of a dysfunction within an anatomic lumen is in the area of cardiac surgery, and specifically valvular repair. Approximately one million open heart surgical procedures are now performed annually in the United States, and twenty percent of these operations are related to cardiac valves.

The field of cardiac surgery was previously transformed by the introduction of the pump oxygenator, which allowed open heart surgery to be performed. Valvular heart surgery was made possible by the further introduction of the mechanical ball-valve prosthesis, and many modifications and different forms of prosthetic heart valves have since been developed. However, the ideal prosthetic valve has yet to be designed, which attests to the elegant form and function of the native heart valve.

As a result of the difficulties in engineering a perfect prosthetic heart valve, there has been growing interest in repairing a patient's native valve. These efforts have documented equal long-term durability to the use of mechanical prostheses, with added benefits of better ventricular performance due to preservation of the subvalvular mechanisms and obviation of the need for chronic anticoagulation. Mitral valve repair has become one of the most rapidly growing areas in adult cardiac surgery today.

Mitral valve disease can be subdivided into intrinsic valve disturbances and pathology extrinsic to the mitral valve ultimately affecting valvular function. Although these subdivisions exist, many of the repair techniques and overall operative approaches are similar in the various pathologies that exist.

Historically, most valvular pathology was secondary to rheumatic heart disease, a result of a streptococcal infection, most commonly affecting the mitral valve, followed by the aortic valve, and least often the pulmonic valve. The results of the infectious process are mitral stenosis and aortic stenosis, followed by mitral insufficiency and aortic insufficiency. With the advent of better antibiotic therapies, the incidence of rheumatic heart disease is on the decline, and accounts for a smaller percentage of valvular heart conditions in the developed world of the present day. Commissurotomy of rheumatic mitral stenosis was an early example of commonly practiced mitral valve repair outside of the realm of congenital heart defects. However, the repairs of rheumatic insufficient valves have not met with good results due to the underlying valve pathology and the progression of disease.

Most mitral valve disease other than rheumatic results in valvular insufficiency that is generally amenable to repair. Chordae rupture is a common cause of mitral insufficiency, resulting in a focal area of regurgitation. Classically, one of the first successful and accepted surgical repairs was for ruptured chordae of the posterior mitral leaflet. The technical feasibility of this repair, its reproducible good results, and its long-term durability led the pioneer surgeons in the field of mitral valve repair to attempt repairs of other valve pathologies.

Mitral valve prolapse is a fairly common condition that leads over time to valvular insufficiency. In this disease, the plane of coaptation of the anterior and posterior leaflets is "atrialized" relative to a normal valve. This problem may readily be repaired by restoring the plane of coaptation into the ventricle.

The papillary muscles within the left ventricle support the mitral valve and aid in its function. Papillary muscle dysfunction, whether due to infarction or ischemia from coronary artery disease, often leads to mitral insufficiency (commonly referred to as ischemic mitral insufficiency). Within the scope of mitral valve disease, this is the most rapidly growing area for valve repair. Historically, only patients with severe mitral insufficiency were repaired or replaced, but there is increasing support in the surgical literature to support valve repair in patients with moderate insufficiency that is attributable to ischemic mitral insufficiency. Early aggressive valve repair in this patient population has been shown to increase survival and improve long-term ventricular function.

In addition, in patients with dilated cardiomyopathy the etiology of mitral insufficiency is the lack of coaptation of the valve leaflets from a dilated ventricle. The resultant regurgitation is due to the lack of coaptation of the leaflets. There is a growing trend to repair these valves, thereby repairing the insufficiency and restoring ventricular geometry, thus improving overall ventricular function.

Two essential features of mitral valve repair are to fix primary valvular pathology (if present) and to support the annulus or reduce the annular dimension using a prosthesis that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using transesophageal echocardiography (TEE). If significant residual valvular insufficiency is then documented, the surgeon must re-arrest the heart, re-open the heart, and then re-repair or replace the valve. This increases overall operative, anesthesia, and bypass times, and therefore increases the overall operative risks.

If the prosthesis used to reduce the annulus is larger than the ideal size, mitral insufficiency may persist. If the prosthesis is too small, mitral stenosis may result.

The need exists, therefore, for an adjustable prosthesis that would allow a surgeon to adjust the annular dimension in situ in a beating heart under TEE guidance or other diagnostic modalities to achieve optimal valvular sufficiency and function.

Cardiac surgery is but one example of a setting in which adjustment of the annular dimension of an anatomic orifice in situ would be desirable. Another example is in the field of gastrointestinal surgery, where the Nissen fundoplication procedure has long been used to narrow the gastro-esophageal junction for relief of gastric reflux into the esophagus. In this setting, a surgeon is conventionally faced with the tension between creating sufficient narrowing to achieve reflux control, but avoiding excessive narrowing that may interfere with the passage of nutrient contents from the esophagus into the stomach. Again, it would be desirable to have a method and apparatus by which the extent to which the gastro-esophageal junction is narrowed could be adjusted in situ to achieve optimal balance between these two competing interests.

Aside from the problem of adjusting the internal circumference of body passages in situ, there is often a need in medicine and surgery to place a prosthetic implant at a desired recipient anatomic site. For example, existing methods proposed for percutaneous mitral repair include approaches through either the coronary sinus or percutaneous attempts to affix the anterior mitral leaflet to the posterior mitral leaflet. Significant clinical and logistical problems attend both of these existing technologies. In the case of the coronary sinus procedures, percutaneous access to the coronary sinus is technically difficult and time consuming to achieve, with procedures which may require several hours to properly access the coronary sinus. Moreover, these procedures employ incomplete annular rings, which compromise their physiologic effect. Such procedures are typically not effective for improving mitral regurgitation by more than one clinical grade. Finally, coronary sinus procedures carry the potentially disastrous risks of either fatal tears or catastrophic thrombosis of the coronary sinus.

Similarly, percutaneous procedures which employ sutures, clips, or other devices to affix the anterior mitral leaflets to the posterior mitral leaflets also have limited reparative capabilities. Such procedures are also typically ineffective in providing a complete repair of mitral regurgitation. Furthermore, surgical experience indicates that such methods are not durable, with likely separation of the affixed valve leaflets. These procedures also fail to address the pathophysiololgy of the dilated mitral annulus in ischemic heart disease. As a result of the residual anatomic pathology, no ventricular remodeling or improved ventricular function is likely with these procedures.

The need exists, therefore, for a delivery system and methods for its use that would avoid the need for open surgery in such exemplary circumstances, and allow delivery, placement, and adjustment of a prosthetic implant to reduce the diameter of such a mitral annulus in a percutaneous or other minimally invasive procedure, while still achieving clinical and physiologic results that are at least the equivalent of the yields of the best open surgical procedures for these same problems.

The preceding cardiac applications are only examples of some applications according to the present invention. Another exemplary application anticipated by the present invention is in the field of gastrointestinal surgery, where the aforementioned Nissen fundoplication procedure has long been used to narrow the gastro-esophageal junction for relief of gastric reflux into the esophagus. In this setting, a surgeon is conventionally faced with the tension between creating sufficient narrowing to achieve reflux control, but avoiding excessive narrowing that may interfere with the passage of nutrient contents from the esophagus into the stomach. Additionally, "gas bloat" may cause the inability to belch, a common complication of over-narrowing of the GE junction. An adjustable prosthetic implant according to the present invention could allow in situ adjustment in such a setting under physiologic assessment after primary surgical closure.

Such an adjustable prosthetic implant according to the present invention could be placed endoscopically, percutaneously, or with an endoscope placed within a body cavity or organ, or by trans-abdominal or trans-thoracic approaches. In addition, such an adjustable prosthetic implant according to the present invention could be coupled with an adjustment means capable of being placed in the subcutaneous or other anatomic tissues within the body, such that remote adjustments could be made to the implant during physiologic function of the implant. This adjustment means can also be contained within the implant and adjusted remotely, i.e. remote control adjustment. Such an adjustment means might be capable of removal from the body, or might be retained within the body indefinitely for later adjustment.

The present invention and the methods for its use anticipate many alternate embodiments in other potential applications in the broad fields of medicine and surgery. Among the other potential applications anticipated according to the present invention are adjustable implants for use in the treatment of morbid obesity, urinary incontinence, anastomotic strictures, arterial stenosis, urinary incontinence, cervical incompetence, ductal strictures, and anal incontinence. The preceding discussions are intended to be exemplary embodiments according to the present invention and should not be construed to limit the present invention and the methods for its use in any way.

SUMMARY OF THE INVENTION

An object of the present invention is to provide an implantable device for controlling at least one of shape and size of an anatomical structure or lumen.

These and other objects of the present invention are achieved in an implantable device for controlling at least on of shape and size of an anatomical structure or lumen. An implantable device is provided that has an adjustable member configured to adjust the dimensions of the implantable device. In certain embodiments, a torqueable adjustment tool is configured to provide adjustment of the dimensions of the implantable device for a preferred dimension. In other embodiments adjustments for a preferred dimension may be accomplished remotely through activation of internal adjustment mechanisms.

In another embodiment of the present invention, an implantable device is provided for controlling at least one of shape and size of an anatomical structure or lumen that includes an implantable device has an adjustable member configured to adjust the dimensions of the implantable device, a particularly a preferred dimension. An adjustment tool is configured to provide adjustment of the dimensions of the implantable device, the adjustment tool providing translated motion through rotation.

In another embodiment of the present invention, an implantable device is provided for controlling at least one of shape and size of an anatomical structure or lumen. An implantable device has an adjustable member configured to adjust the dimensions of the implantable device and includes first and second bands. An adjustment tool is configured to provide adjustment of the dimensions of the implantable device for a preferred dimension.

In still another embodiment of the present invention, an implantable device is provided for controlling at least one of shape and size of an anatomical structure or lumen. An implantable device has an adjustable member configured to adjust the dimensions of the implantable device. The implantable device has an anterior portion, a posterior portion and dual threads that provide preferential adjustment of one side or the other of the implantable device. An adjustment tool is configured to provide adjustment of the dimensions of the implantable device.

In yet another embodiment of the present invention, an implantable device controls at least one of shape and size of an anatomical structure or lumen. An implantable device has an adjustable member configured to adjust the dimensions of the implantable device. An adjustment tool is configured to provide adjustment of the dimensions of the implantable device. The adjustment tool provides reciprocating action to provide for the adjustment.

In another embodiment of the present invention, an implantable device controls at least one of shape and size of an anatomical structure or lumen. An implantable device has an adjustable member configured to adjust the dimensions of the implantable device. An adjustment tool is configured to provide adjustment of the dimensions of the implantable device. The adjustment tool provides both course adjustment and fine adjustment.

Other features and advantages of the present invention will become apparent upon reading the following specification, when taken in conjunction with the drawings and the appended claims.

BRIEF DESCRIPTION OF FIGURES

FIG. 17 shows the implant in the folded position, and FIG. 18 shows the implant in the unfolded position.

FIG. 25 is a front view of a fifth embodiment of an implant for reducing the circumference of an anatomic orifice, with the implant shown in its expanded configuration.

FIG. 26 is a front view of the implant of FIG. 25, with the implant shown in its contracted configuration.

FIG. 27 is an enlarged view of the area indicated by the circle 27 in FIG. 25, with the outer body removed to show interior detail.

FIGS. 63-72 show a reversible attachment apparatus that can be used to attach an adjustable implant to an anatomic orifice or lumen using a minimally invasive procedure.

DETAILED DESCRIPTION OF THE INVENTION

Figure 1:
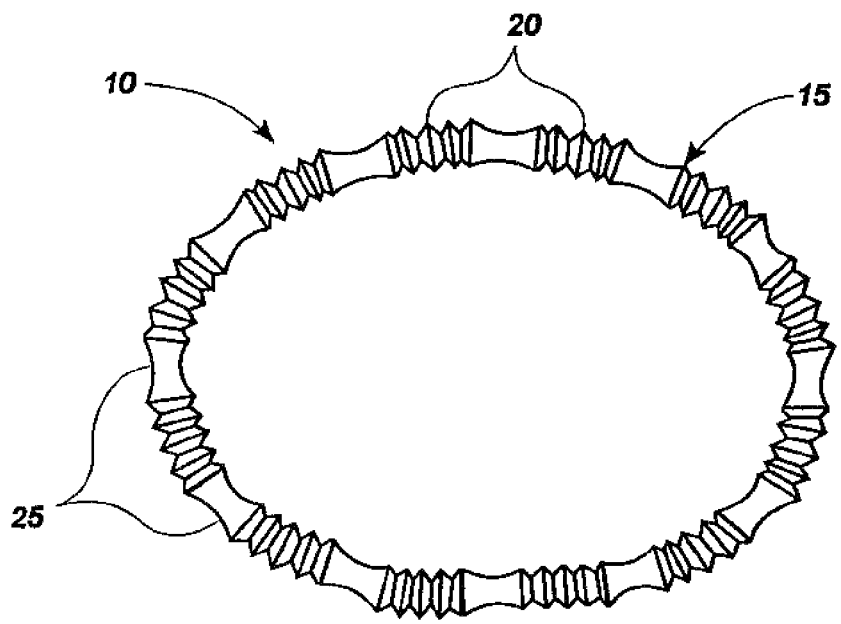
FIG. 1 is a front view of a first embodiment of an implant for reducing the circumference of an anatomic orifice.

Referring now to the drawings, in which like numerals indicate like elements throughout the several views, an exemplary implant 10 comprising an implant body 15 is shown in FIG. 1. The implant body may be provided in a shape and size determined by the anatomic needs of an intended native recipient anatomic site within a mammalian patient. Such a native recipient anatomic site may be, by way of illustration and not by way of limitation, a heart valve, the esophagus near the gastro-esophageal junction, the anus, or other anatomic sites within a mammalian body that are creating dysfunction that might be relieved by an implant capable of changing the size and shape of that site and maintaining a desired size and shape after surgery.

Figure 2:
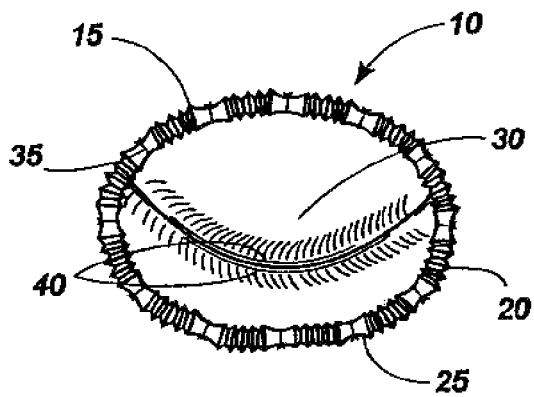
FIG. 2 is a front view of the implant of FIG. 1 secured to the annulus of a mitral valve, with the implant in an expanded position.
Figure 3:
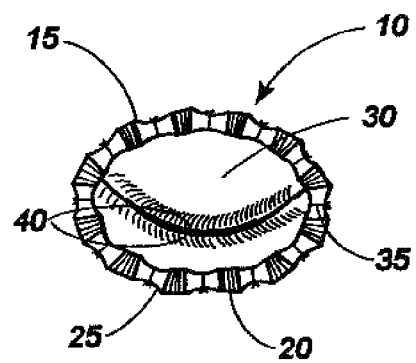
FIG. 3 is a front view of the implant of FIG. 1 secured to the annulus of a mitral valve, with the implant in a contracted position to reduced the size of the heart valve opening.

The implant 10 of FIG. 1 comprises a circular implant body 15 which is provided with adjustable corrugated sections 20 alternating with intervening grommet-like attachment means 25 having narrowed intermediate neck portions. As can be seen in FIGS. 2 and 3, the implant body 15 may be secured to the annulus of a heart valve 30 by a fixation means such as a suture 35 secured over or through the attachment means 25. The corrugated sections 20 fold and unfold as the circumference of the implant body 15 shortens or lengthens. Adjustment of the implant 10 in situ may decrease the overall size of the heart valve 30, increasing the coaptation of the valve leaflets 40, and changing the configuration from that shown in FIG. 2 to that shown in FIG. 3.

Figure 4:
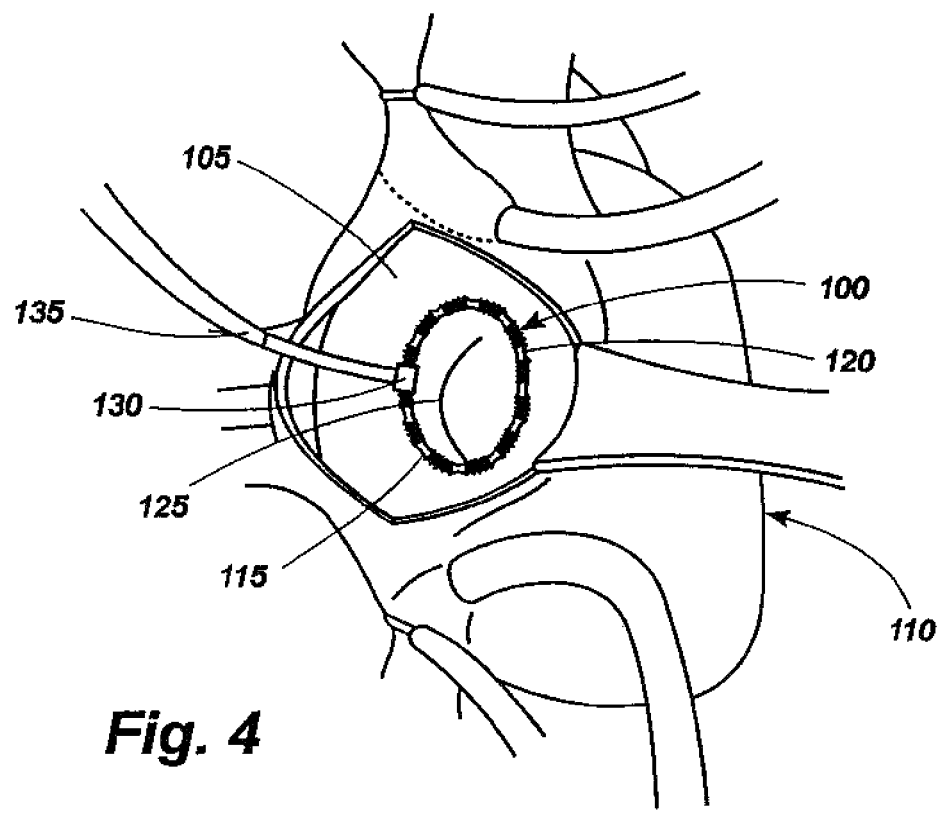
FIG. 4 is a perspective view of a second embodiment of an implant for reducing the circumference of an anatomic orifice, inserted through an open operative cardiac incision and secured around the mitral valve.
Figure 5:
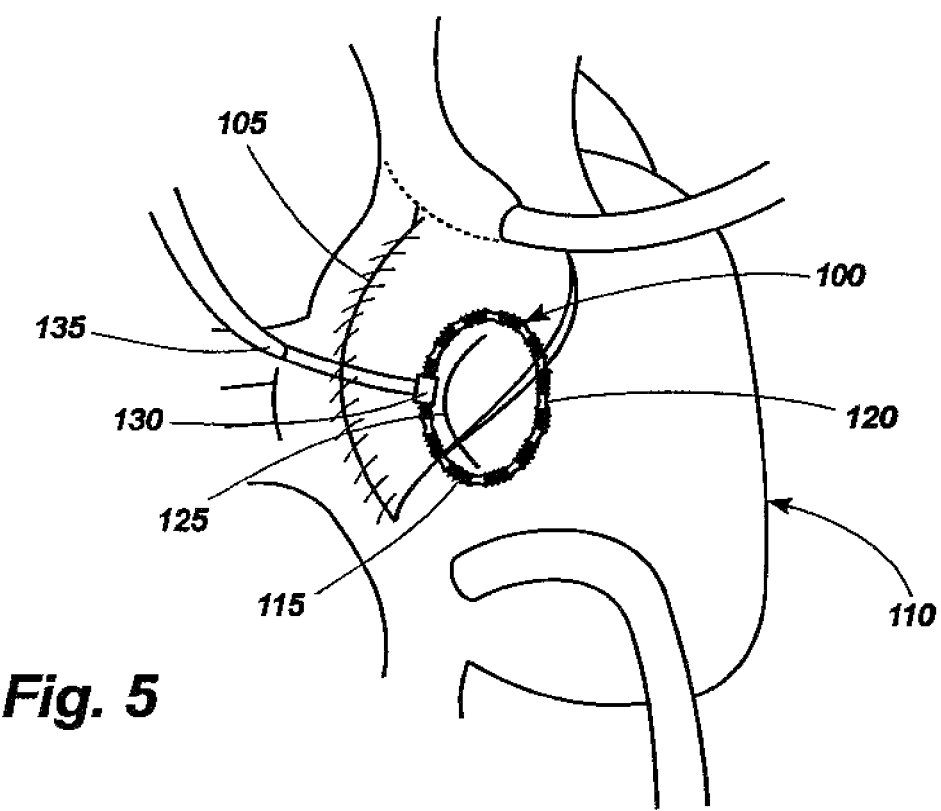
FIG. 5 is a perspective view of the implant of FIG. 4, showing the cardiac incision closed, an adjustment tool extending through the closed incision, and adjustment of the implant possible after the patient has been taken "off pump."

An additional exemplary embodiment 100 of the present invention is shown in FIGS. 4 and 5, with an open operative cardiac incision 105 in a heart 110 shown in FIG. 4, and closure of the cardiac incision 105 in FIG. 5. As shown in FIG. 4, the exemplary adjustable implant 100 according to the present invention comprises an implant body 115 with attachment means 120 that allows fixation to the annulus of a mitral valve 125. The exemplary adjustable implant 100 is further provided with an adjustment means 130 that is controlled by an attached or coupled adjustment tool 135. After closure of the myocardial incision 105 in FIG. 5, the adjustment tool 135 remains attached or coupled to the adjustment means 130, so that the size and shape of the implant 100 may further be affected after physiologic flow through the heart 110 is resumed, but with the chest incision still open. Once the desired shape and function are achieved, the adjustment tool 135 may be disengaged from the adjustment means 130 and withdrawn from the myocardial incision 105. In various embodiments according to the present invention, the adjustment means 130 may be configured and placed to allow retention by or re-introduction of the adjustment tool 135 for adjustment following closure of the chest incision.

To use the implant 100 of FIGS. 4 and 5, the physician makes the open operative incision 105 in the heart 110, as shown in FIG. 4, in the conventional manner. The implant 100, mounted at the forward end of adjustment tool 135, is then advanced through the incision 105 and sutured to the annulus of the mitral valve 125. The adjustment tool 135 is then manipulated, e.g., rotated, depending upon the design of the adjustment means 130, to cause the adjustment means to reduce the size of the implant body 115, and hence the underlying mitral valve 125 to which it is sutured, to an approximate size. The myocardial incision 105 can now be closed, as shown in FIG. 5, leaving the adjustment tool extending through the incision for post-operative adjustment.

Once the patient has been taken "off pump" and normal flow of blood through the heart 110 has resumed, but before the chest incision has been closed, further adjustments to the size of the mitral valve 125 can be made by manipulating the adjustment tool 135.

Figure 6:
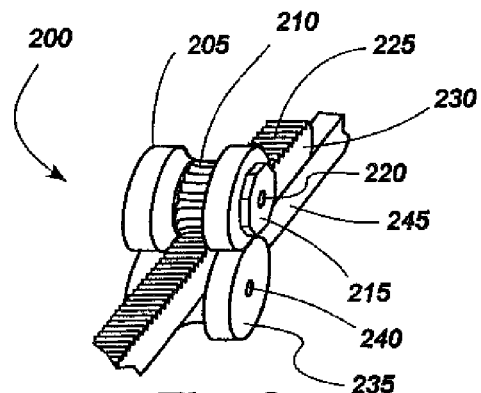
FIG. 6 is a perspective view of a first embodiment of an adjustment means for adjusting the circumference of an implant for reducing the circumference of an anatomic orifice.
Figure 7:
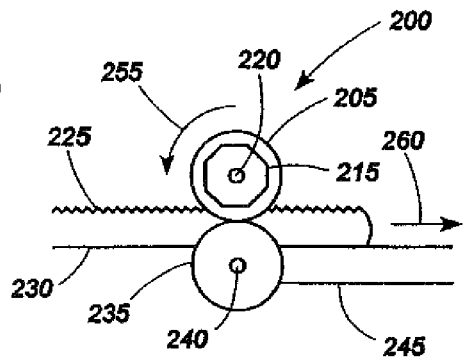
FIG. 7 is a right side view of the adjustment means of FIG. 6.
Figure 8:
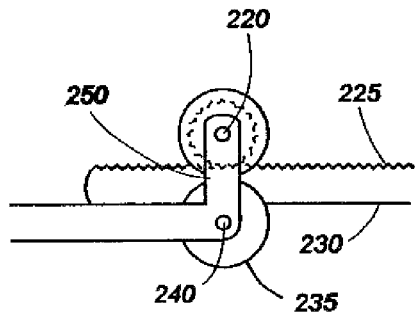
FIG. 8 is a left side view of the adjustment means of FIG. 6.

FIGS. 6-8 show an exemplary adjustment means 200 for adjusting the circumference of an annular implant such as the implant 100 previously described. The adjustment means 200 comprises a rack and pinion system in which a first cam 205 with geared teeth 210 and an engagement coupler 215 turns on a first axle 220. In this example, the first cam 205 engages a geared rack 225 on one or more surfaces of a first band 230. The first band 230 passes between the first cam 205 and a second cam 235 that turns on a second axle 240 that is joined to a second band 245. As shown in FIG. 8, the first and second axles 220, 240 are maintained in suitable spaced-apart relation by means of a bracket 250 formed at the end of the second band 245.

The adjustment means 200 is preferably set within a hollow annular implant 100 of the type previously described, though it is possible to use the adjustment means in a stand-alone configuration wherein the first and second bands 230, 245 are opposing ends of the same continuous annular structure. In either event, to adjust the length of an implant comprising the adjustment means 200, a tool such as a hex wrench engages the engagement coupler 215 on the first cam 205 and rotates the first cam in a counterclockwise direction as shown in FIG. 7, as indicated by the arrow 255. Rotation of the first cam 205 causes the teeth 210 to drive the rack 225 to move the first band 230 toward the right, as indicated by the arrow 260 in FIG. 7. This movement of the first band tightens the circumference of the annular implant. If the physician inadvertently adjusts the implant too tight, reversing direction of the engagement coupler 215 will loosen the implant.

In various embodiments according to the present invention, the first and second bands 230, 245 may be separate structures, or they may be opposing ends of the same continuous structure. In such an embodiment, when motion is imparted to the engagement coupler 215, the first cam 205 is rotated, causing the geared teeth 210 to engage the geared rack 225, and causing the first band 230 to move with respect to the second band 245 to adjust the circumference of an implant.

Figure 9:
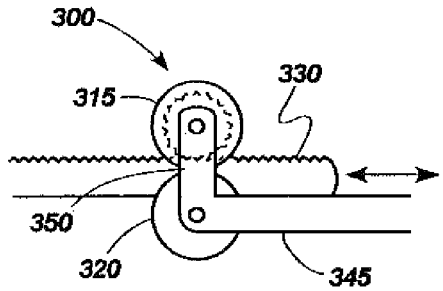
FIG. 9 is a right side view of a second embodiment of an adjustment means for adjusting the circumference of an implant for reducing the circumference of an anatomic orifice.

FIG. 9 shows a somewhat different configuration of an exemplary engagement means 300 according to the present invention, in which there is no engagement coupler, and a bracket 350 is provided on both sides of the cams to maintain the first cam 315 and the second cam 320 in close approximation. In one proposed embodiment, the bracket is designed with close tolerances so as to press the first band 330 closely against the second band 345, thereby to hold the bands in fixed relative position by friction. In another proposed embodiment, the brackets 350 are fabricated from an elastic material such that the cams 315, 320 can be spread apart to insert the first band 330 between the cams, whereupon the cams are pulled back together with sufficient force to hold the bands 330, 345 in fixed relative position by friction. In still another proposed embodiment involving an elastic mounting arrangement between the cams 315, 320, the lower edge of the first band 330 and the upper edge of the second band 345 have mating frictional or mechanical surfaces, whereby the cams 315, 320 can be spread apart to permit relative movement between the bands or released to clamp the bands together in fixed relation.

Figure 10:
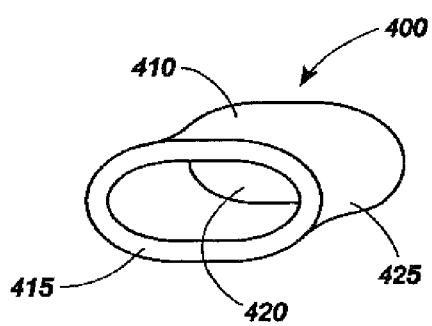
FIG. 10 is a perspective view of a first alternate embodiment of an attachment means for the implant of FIG. 1.

FIG. 10 shows an exemplary attachment means 400 for an implant according to the present invention. The attachment means 400 could be used, for example, in place of the attachment means 25 of the implant 10. The attachment means 400 takes the form of a grommet 410 comprising a wall 415 defining a lumen 420 and an attachment surface 425. Such an attachment means would be used with the implant body extending through the lumen 420 and with fixation devices such as sutures or wires either tied over or affixed through the attachment surface 425.

Figure 11:
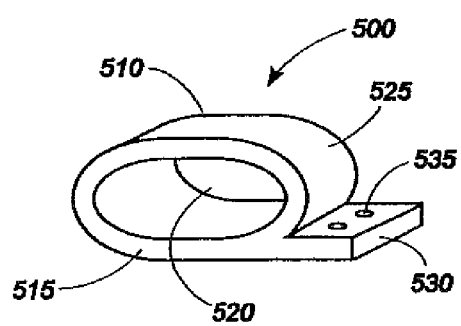
FIG. 11 is a perspective view of a second alternate embodiment of an attachment means for the implant of FIG. 1.
Figure 12:
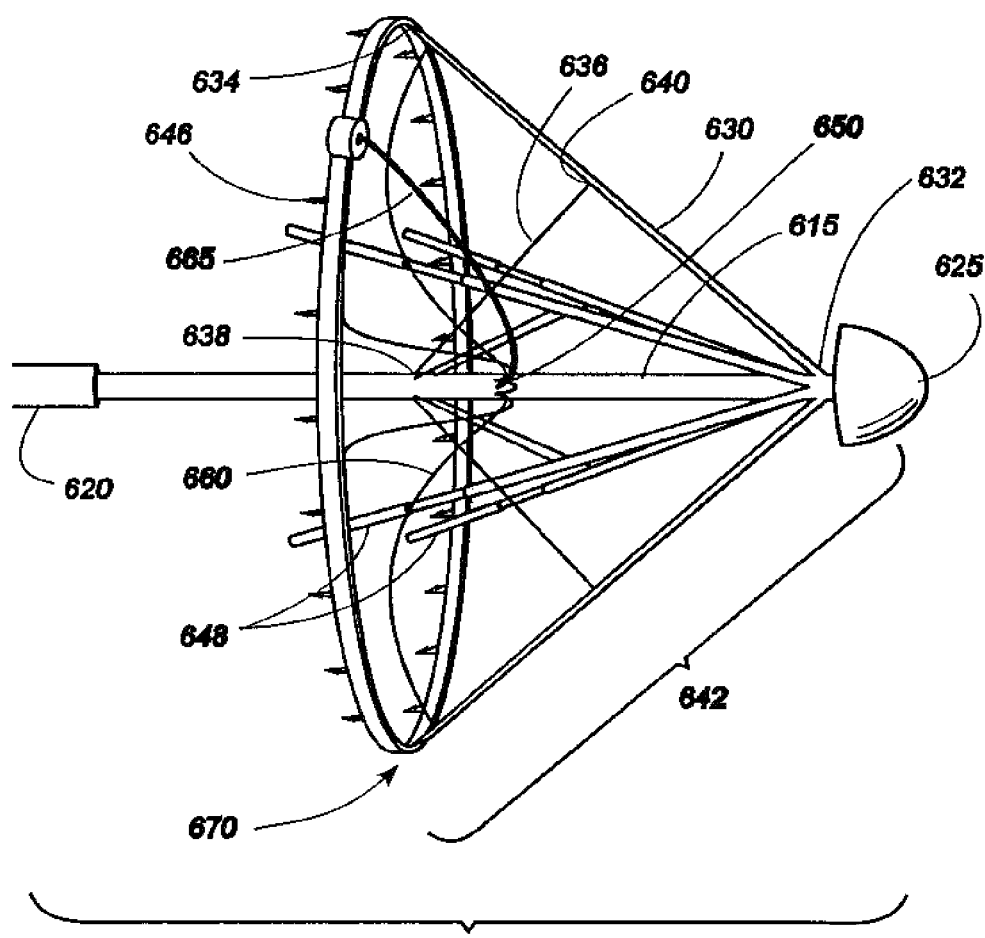
FIG. 12 is a perspective view of a third embodiment of an implant for reducing the circumference of an anatomic orifice.

FIG. 11 shows another alternate embodiment of an attachment means 500 for an implant according to the present invention. The attachment means 500 could also be used, for example, in place of the attachment means 25 of the implant 10. FIG. 11 shows an attachment means 500 in the form of a hollow tube or tube segment 510 comprising a wall 515 defining a lumen 520, an outer surface 525, and an attachment tab 530. Such an attachment means would be used with the implant body extending through the lumen 520 and with fixation devices such as sutures or wires either tied or otherwise affixed over or through the attachment tab 530. Such fixation devices might be placed through holes 535 provided in the attachment tab 530. Alternately a solid attachment tab 530 might be provided, and the fixation devices might be passed through the solid tab. Modifications of these attachment means may be used in conjunction with a sutureless attachment system.

Figure 13:
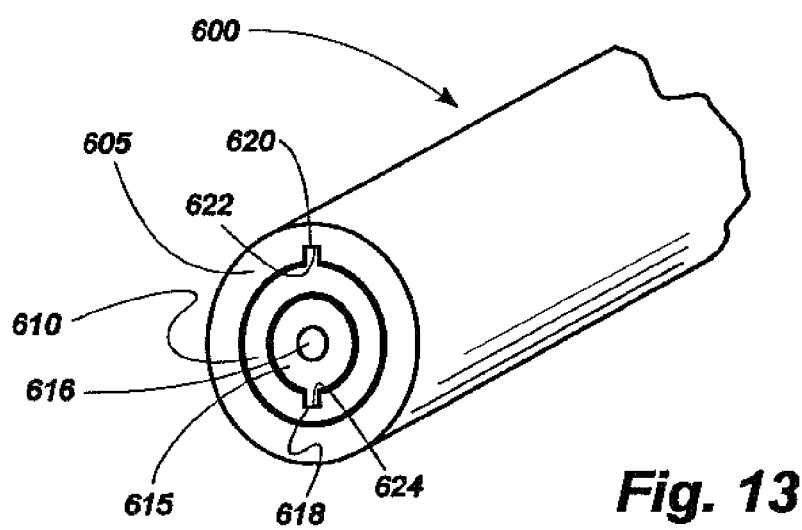
FIG. 13 is a perspective view of one end of the implant of FIG. 12 showing an optional keyed relationship between three coaxial cannulae to prevent relative rotation between the three components.

FIGS. 12-18 show another embodiment of a percutaneous annuloplasty device according to the present invention, in which an implant/delivery system array 600 includes a housing sheath 605 (not seen in FIG. 12), an actuating catheter 610 coaxially slidably mounted within the housing sheath 605, and a core catheter 615 coaxially slidably mounted within the actuating catheter 610. The core catheter has a central lumen 616 (FIG. 13). The actuating catheter 610 and core catheter 615 may be round tubular structures, or as shown in FIG. 13, either or both of the actuating and core catheters may be provided with one or more keyed ridges 618, 620 respectively to be received by one or more reciprocal slots 622, 624 within the inner lumen of either the housing sheath 605 or the actuating catheter 610, respectively. Such keyed ridges 618, 620 would limit internal rotation of an inner element within an outer element, should such restriction be desirable to maintain control of the inner contents from inadvertent displacement due to undersired rotational motion during use.

The implant/delivery system array 600 includes a distal tip 625 at the forward end of the core catheter 615. One or more radial implant support arms 630 have their distal ends 632 pivotably or bendably mounted to the core catheter 615 adjacent its distal tip 625. The proximal ends 634 of the radial implant support arms 630 normally extend along the core catheter 615 but are capable of being displaced outward away from the core catheter.

One or more radial support struts 636 have their proximal ends 638 pivotably or bendably mounted to the distal end of the actuating catheter 610. The distal end 640 of each radial support strut is 636 pivotably or bendably attached to a midpoint of a corresponding radial implant support arm 630. As the actuating catheter 610 is advanced with respect to the core catheter 615, the radial support struts 636 force the radial implant support arms 630 upward and outward in the fashion of an umbrella frame. Thus the actuating catheter 610, core catheter 615, radial support struts 636, and radial support arms 630 in combination form a deployment umbrella 642.

Figure 14:
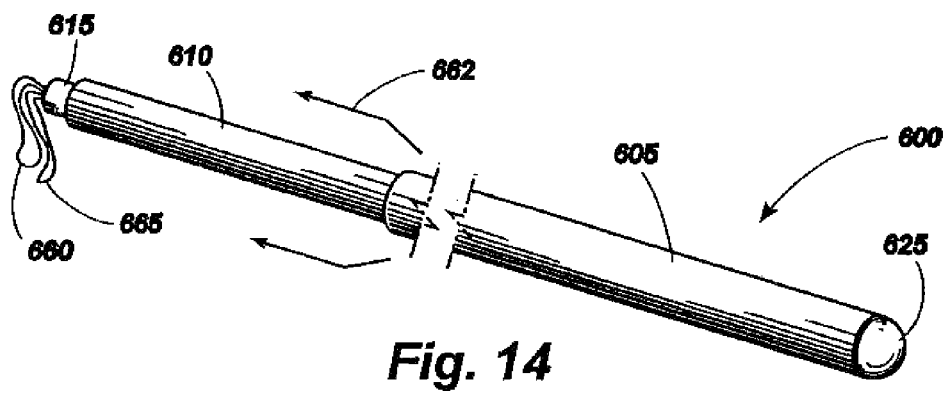
FIG. 14 is a perspective view of the implant of FIG. 12 showing the outer cannula extended to cover the implant.
Figure 15:
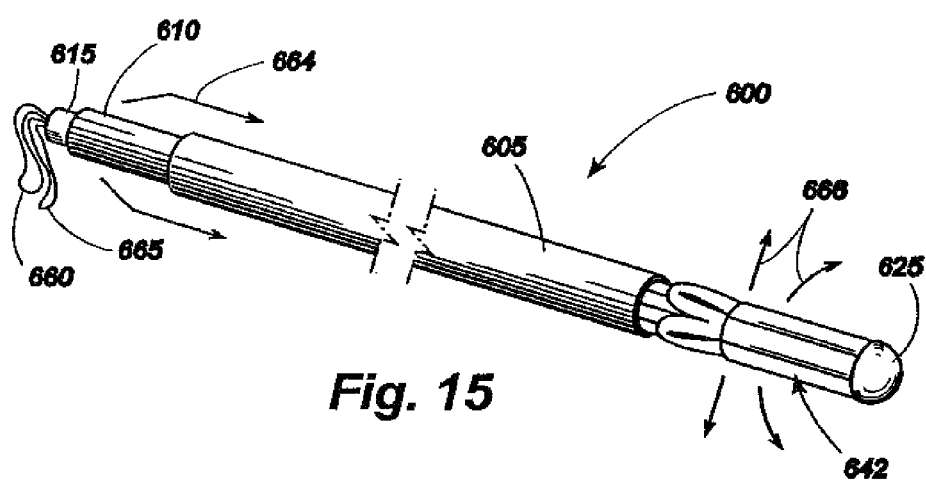
FIG. 15 is a perspective view of the implant of FIG. 12 showing the outer cannula retracted to expose the implant.
Figure 16:
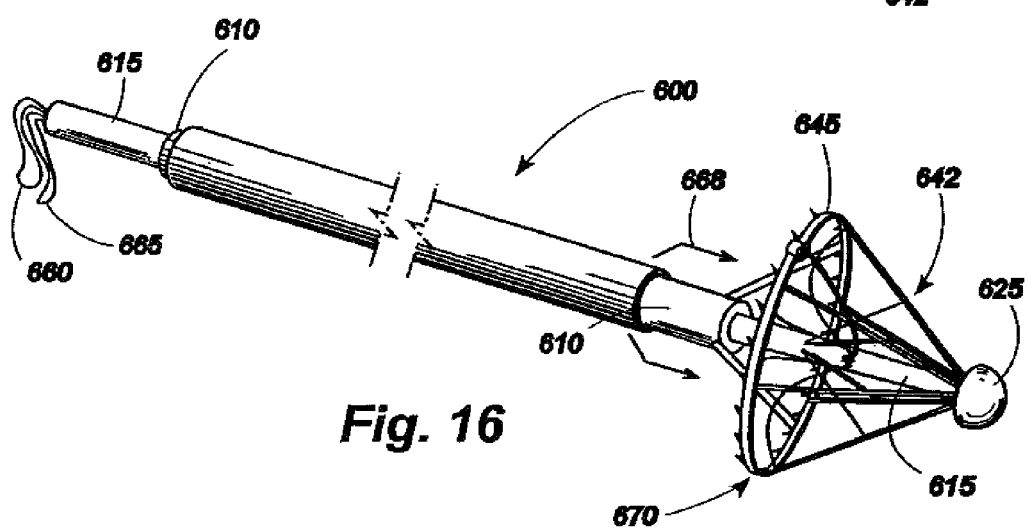
FIG. 16 is a perspective view of the implant of FIG. 12 showing the middle cannula extended to unfold the implant.

A prosthetic implant 645 is releasably attached to the proximal ends 634 of the radial implant support arms 630. Around the periphery of the prosthetic implant 645 and extending proximally therefrom are a plurality of retention barbs 646. In addition, one or more of the radial implant support arms 630 comprise touchdown sensors 648 whose proximal ends extend proximal to the implant 645. Extending through the central lumen 616 (FIG. 13) of the core catheter 615 in the exemplary embodiment 600 and out lateral ports 650 (FIG. 12) spaced proximally from the distal tip 625 are one or more release elements 660, which serve to release the implant 645 from the delivery system, and one or more adjustment elements 665 which serve to adjust the implant's deployed size and effect. Because the release elements 660 and adjustment elements 665 extend through the proximal end of the core catheter 615, as seen in FIGS. 14-16, these elements can be directly or indirectly instrumented or manipulated by the physician. A delivery interface 670 (FIGS. 12,16) is defined in this example by the interaction of the deployment umbrella 642, the release elements 660, and the implant 645. In the disclosed embodiment, the release elements 660 may be a suture, fiber, or wire in a continuous loop that passes through laser-drilled bores in the implant 645 and in the radial implant support arms 630, and then passes through the length of the core catheter 615. In such an embodiment, the implant 645 may be released from the delivery system at a desired time by severing the release element 660 at its proximal end, outside the patient, and then withdrawing the free end of the release element 660 through the core catheter 610.

FIGS. 14-16 show the operation of the implant/delivery system array 600, in which an umbrella-like expansion of the prosthetic implant 645 is achieved by sliding movement of the housing sheath 605, the actuating catheter 610, and the core catheter 615. Referring first to FIG. 14, the housing sheath 605 is extended to cover the forward ends of the actuating catheter 610 and core catheter 615 for intravascular insertion of the implant/delivery system array 600. From this starting position, the housing sheath 605 is retracted in the direction indicated by the arrows 662. In FIG. 15 the housing sheath 605 has been retracted to expose the forward end of the actuating catheter 610 and the collapsed deployment umbrella 642. From this position the actuating catheter 610 is advanced in the direction indicated by the arrows 664. This will cause the deployment umbrellas to expand in the directions indicated by the arrows 666. FIG. 16 shows the expansion of the deployment umbrella 642 produced by distal motion of the actuating catheter 610 relative to the core catheter 615. After the implant 645 has been positioned and adjusted to the proper size, the housing sheath 605 is advanced in the direction indicated by the arrows 668 to collapse and to cover the deployment umbrella 642 for withdrawal of the device from the patient.

Figure 17:
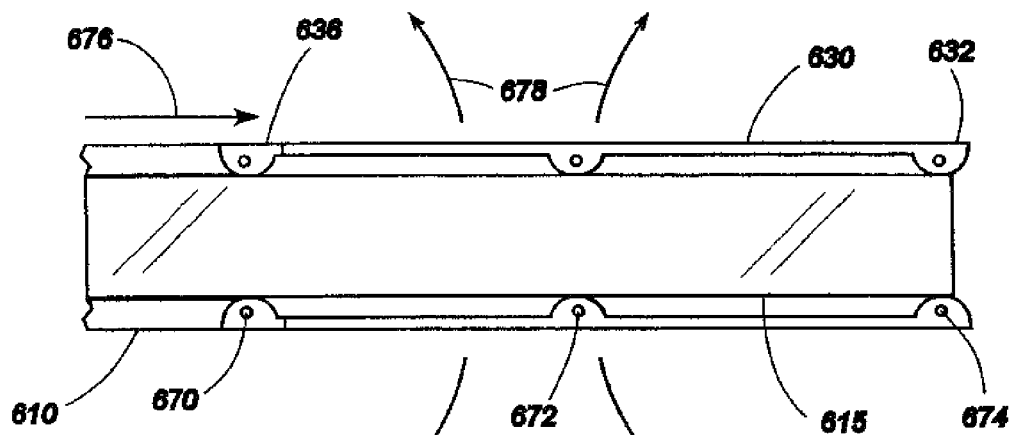
FIGS. 17 and 18 are schematic views illustrating how extension of the middle cannula causes the implant to unfold, where
Figure 18:
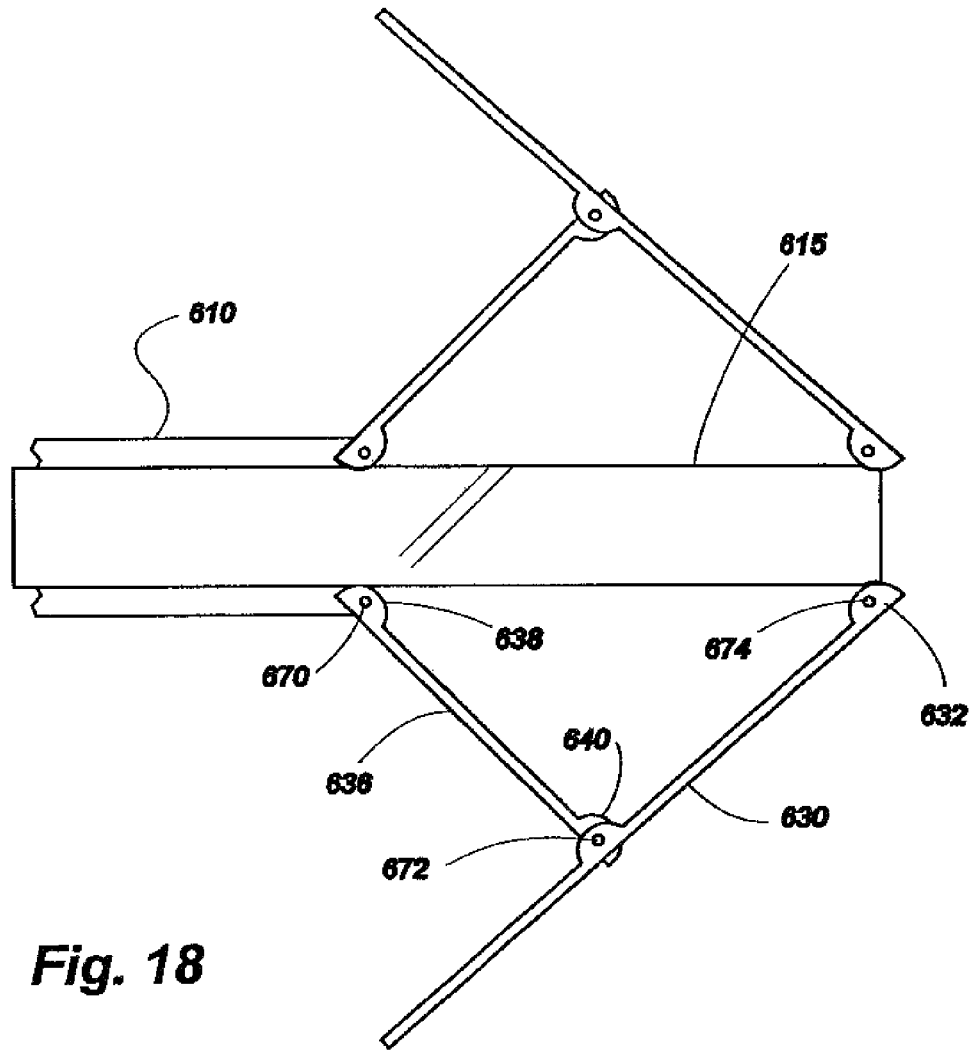

FIGS. 17 and 18 are schematic views illustrating the radial implant support arms 630 and the radial support struts 636 of the implant/delivery system array 600. In FIG. 17, a radial support strut 636 is pivotably attached at its proximal end 638 at a first pivotable joint 670 to the actuation catheter 610. The radial support strut 636 is attached at its distal end 640 to a second pivotable joint 672 at an intermediate point of a corresponding radial implant support arm 630. The radial implant support arm 630 is attached at its distal end 632 by a third pivotable joint 674 to the core catheter 620. FIG. 17 shows the assembly in a closed state. When the actuation catheter 610 is advanced distally over the core catheter 615, as shown by the arrows 676, the radial support strut 636 and the radial implant support arm 630 are extended by the motion at the first pivotable joint 670, the second pivotable joint 672, and the third pivotable joint 674, as shown by the arrow 678. This motion has the effect of expanding the deployment umbrella and folded implant (not shown in FIGS. 17 and 18), allowing it to achieve its greatest radial dimension, prior to engagement and implantation as previously discussed with reference to FIGS. 12-16.

Figure 19:
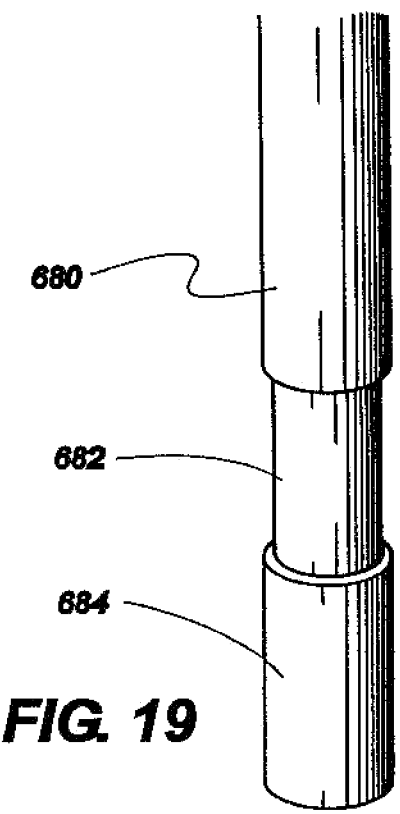
FIG. 19 is a perspective view of the lower end of a touch-down sensor of the implant of FIG. 12, showing the sensor in an uncompressed condition.
Figure 20:
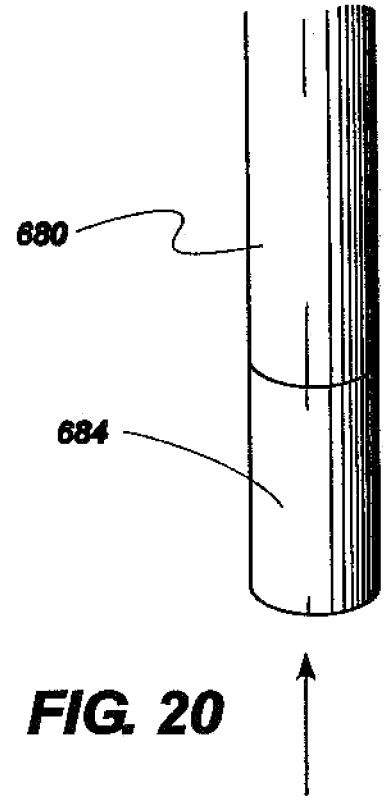
FIG. 20 is a perspective view of the lower end of the touchdown sensor of FIG. 19, showing the sensor in a compressed condition.

FIGS. 19 and 20 show further details of the touchdown sensors 648 shown previously in FIG. 12. The touchdown sensor 648 of FIGS. 19 and 20 includes a distal segment 680, an intermediate segment 682, and a proximal segment 684. The distal segment 680 is spring-mounted, so that it is capable of slidable, telescoping displacement over the intermediate segment 682 to achieve a seamless junction with the proximal segment 684 upon maximal displacement. When the touchdown sensor 648 is in its normal condition, the spring extends the proximal segment such that the sensor assumes the orientation shown in FIG. 19. When the implant 645 (FIG. 12) is seated against the periphery of an anatomical opening, the proximal segment 684 of the sensor 648 is compressed against the distal segment 680, as shown in FIG. 20. The distal segment 680 and the proximal segment 684 are both constructed of, are sheathed by, or otherwise covered with a radio-opaque material. However, the intermediate segment 682 is not constructed or coated with such a radio-opaque material. Therefore, when the distal segment 680 is at rest, it is fully extended from the proximal segment 684, and the gap represented by the exposed intermediate segment 682 is visible on radiographic examination. However, when the distal segment 680 is brought to maximum closeness with the proximal segment 684, no such radio-opaque gap is radiographically visible, and the touchdown sensor is said to be "activated". This embodiment allows radiographic monitoring of the position of the touchdown sensor 648 with respect to the degree of extension of the distal catheter segment 680. In the embodiment according to the present invention as shown, one or more touchdown detectors 648 are employed to ascertain that the delivery system for the prosthetic device is located in the proper position to deploy the implant into the mitral annulus. As this anatomic structure cannot be directly identified on fluoroscopy or standard radiographic procedures, such precise location could be otherwise difficult. At the same time, precise localization and engagement of the mitral annulus is critical for proper implant function and safety.

Touchdown detectors within the embodiments according to the present invention can have a multiplicity of forms, including the telescoping, spring-loaded, radio-opaque elements joined by a non-radio-opaque element as in the aforementioned examples. In embodiments employing magnetic resonance imaging, touchdown detectors according to the present invention may utilize metallic segments interposed by nonmetallic segments in a similar telescoping, spring-loaded array. Other embodiments include a visually-evident system with telescoping, spring-loaded elements with color-coded or other visual features for procedures in which direct or endoscopic observation would be possible. Still other embodiments of touchdown detectors according to the present invention include touchdown detectors provided with microswitches at their tips, such that momentary contact of sufficient pressure completes an electrical circuit and signals the activation of the touchdown detector to the operator. Still other touchdown detectors according to the present invention are provided with fiberoptic pathways for Rahmen laser spectroscopy or other spectral analytical techniques which are capable of detecting unique tissue qualities of the tissue at the desired site for implantation. In addition, still other embodiments according to the present invention include touchdown detectors containing electrodes or other electronic sensors capable of detecting and signaling the operator when a desired electrophysiologic, impedance, or other measurable quality of the desired tissue is detected for proper implantation. Such electrophysiologic touchdown detectors may include electrical circuits that produce visual, auditory, or other signals to the operator that the detectors are activated and that the implant is in the proper position for attachment.

In yet other embodiments according to the present invention, other intracardiac or extracardiac imaging techniques including, but not limited to, intravascular ultrasound, nuclear magnetic resonance, virtual anatomic positioning systems, or other imaging techniques may be employed to confirm proper positioning of the implant, obviating the need for the touchdown sensors as previously described.

Figure 21:
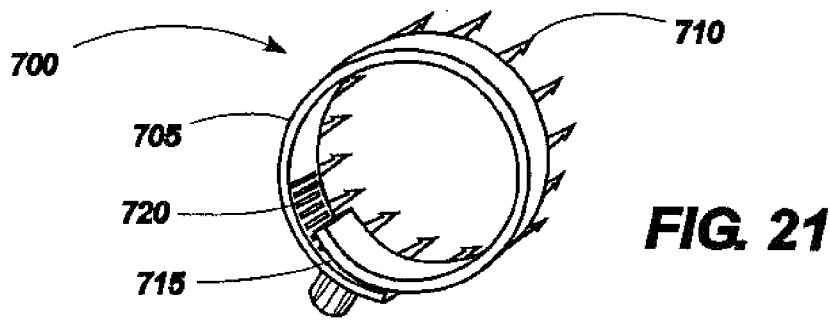
FIG. 21 is a perspective end view of a fourth embodiment of an implant for reducing the circumference of an anatomic orifice.
Figure 22:
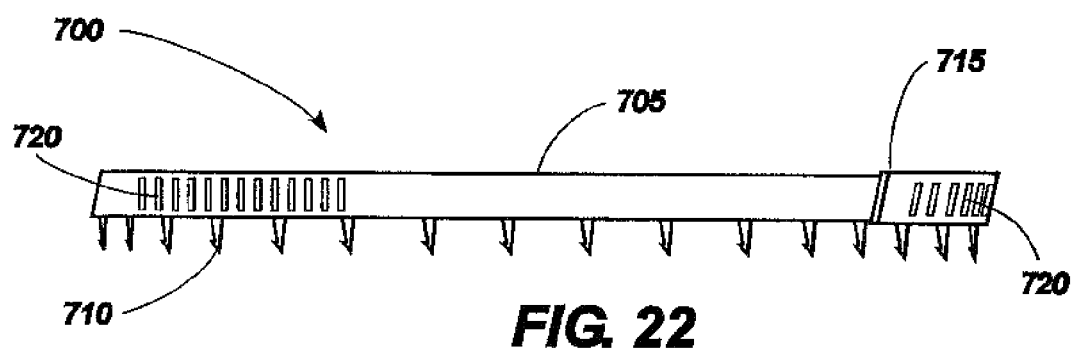
FIG. 22 is a side view of the implant of FIG. 21 with the implant opened up to show its full length.
Figure 23:
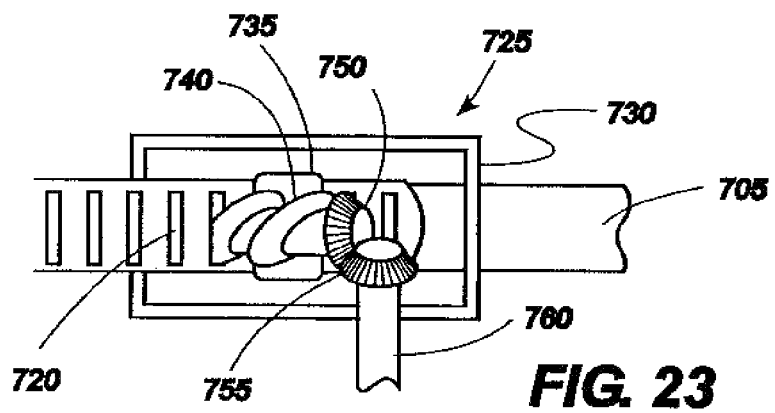
FIG. 23 is a side view of the adjustment mechanism of the implant of FIG. 21.

FIGS. 21-24 show an implant 700 according to one embodiment of the present invention. In this embodiment, the implant body 705 is bandlike and flexible. Through much of its length, the implant body 705 is provided with a series of retention barbs 710 which are oriented to facilitate placement, retention, and removal of the device. The implant body 705 is also provided with an adjustable section 715, which is provided in this example with a series of adjustment stops 720. The adjustment stops 720 may be slots, holes, detents, dimples, ridges, teeth, raised elements, or other mechanical features to allow measured adjustment of the implant 700 in use. In the embodiment shown in FIGS. 21-24, the adjustment stops 720 are engaged by a geared connector 725. FIG. 21 is an end view, showing the implant body 705 curved on itself, with the retention barbs 710 to the exterior, and with the adjustable section 715 passing through its engagement with the geared connector 725 and curving internally within the implant body 705 to form a closed, round structure. FIG. 23 shows details of an exemplary geared connector 725, in which a housing 730 is connected to the implant body 705. The housing 730 contains and supports a mechanical worm 740 with an attached first geared head 750 which mates with a second geared head 755. The second geared head 755 is attached to an adjustment stem 760 which is machined to receive a screwdriver-like adjustment element. The various embodiments according to the present invention may require a number of forms of adjustment elements. In the present example, the adjustment element is provided as a finely coiled wire with a distal tip machined to be received by a receiving slot in the adjustment stem 760 (not shown). The relationship between the distal tip of the adjustment element and the adjustment stem 760 is mechanically similar to a screwdriver bit and screwhead, such that torsion imparted to the adjustment means by the operator will result in the turning of the adjustment stem 760 and second geared head 755 allows motion of the first geared head 750 and worm 740, which creates motion of the adjustable implant section 715 as the worm engages with the series of adjustment tops 725. Excess length of the adjustable section 715 passes though a band slot 735 (FIG. 23), thus allowing the band to move concentrically inside the closed implant body 705. The adjustment element in this embodiment may be designed to remain in place after the deployment umbrella has been retracted and withdrawn. The connection between the adjustment element's distal tip and the adjustment stem 760 may be a simple friction connection, a mechanical key/slot formation, or may be magnetically or electronically maintained.

Figure 24:
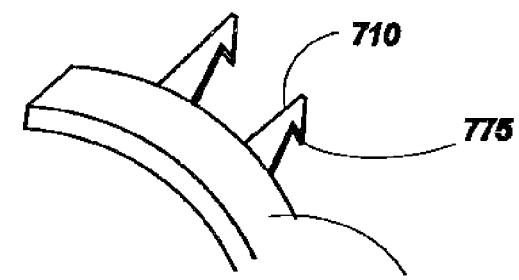
FIG. 24 is a close-up view of two of the retention barbs of the implant of FIG. 21.

As further shown in FIG. 21, the exemplary embodiment employs unidirectional retention barbs 710 which are attached to the outer perimeter of the implant body 705. The retention barbs 710 are oriented in a consistent, tangential position with respect to the implant body 705 such that rotational motion of the implant body will either engage or release the retention barbs 710 upon contact with the desired tissue at the time of deployment. This positioning of the retention barbs 710 allows the operator to "screw in" the implant 700 by turning the implant 700 upon its axis, thus engaging the retention barbs 710 into the adjacent tissue. As shown in FIG. 24, the retention barbs 710 may each be further provided with a terminal hook 775 at the end which would allow for smooth passage through tissue when engaging the retention barbs 710 by rotating the implant 700, without permitting the implant 700 to rotate in the opposite direction, because of the action of the terminal hooks 775 grasping the surrounding tissue (much like barbed fish hooks). The terminal hooks 775 thus ensure the seating of the implant 700 into the surrounding tissue.

FIGS. 25-27 illustrate another embodiment of an implant 800 as contemplated according to the present invention. The implant 800 includes a band 805 (FIG. 27), but the retention barbs of the previous example have been eliminated in favor of an outer fabric implant sheath 810. The fabric sheath 810 can be sutured or otherwise affixed to the anatomic tissue in a desired location. The circumference of the implant body 800 is adjusted through a geared connector 825 similar to the geared connector of the bandlike implant array shown in FIG. 23. More specifically, adjustment stops 820 on the band are engaged by a mechanical worm 840 with an attached first geared head 850. The first geared head 850 mates with a second geared head 855. The second geared head 855 is attached to an adjustment stem 860 which is machined to receive a screwdriver-like adjustment element.

Figure 28:
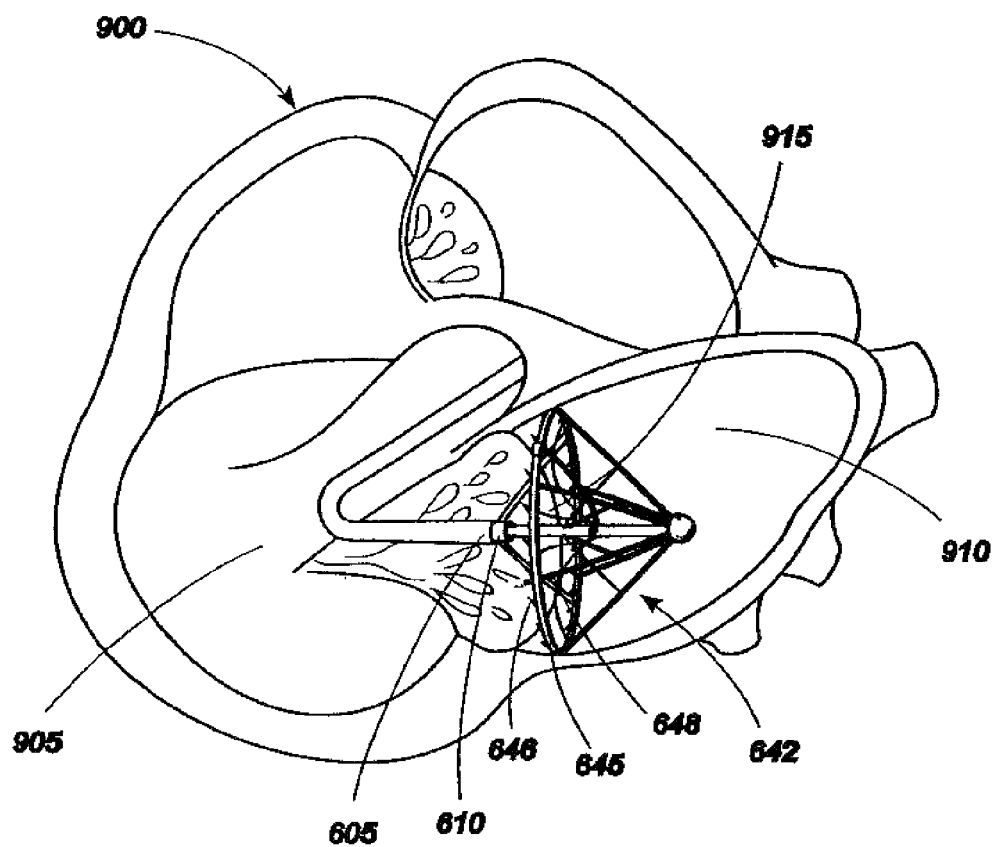
FIG. 28 is a schematic view showing the implant of FIG. 12 anatomically positioned at the mitral annulus in a heart with the implant in a fully expanded state.

FIG. 28 illustrates an example of the method of use of an implant/delivery system array 600 for positioning an implant 645 in a patient with ischemic annular dilatation and mitral regurgitation. Peripheral arterial access is obtained via conventional cutdown, arterial puncture, or other standard access techniques. After access to the arterial system is attained, guidewire placement is performed and intravascular access to the heart 900 is obtained using fluoroscopic, ultrasound, three-dimension ultrasound, magnetic resonance, or other real-time imaging techniques. The guidewire, deployment device, and implant are passed through the aortic valve in a retrograde fashion into the left ventricle 905 and then into the left atrium 910. At this point, the operator retracts the housing sheath 605, thus unsheathing the collapsed deployment umbrella 642 and implant 645. The deployment umbrella 642 is then distended by the distal motion of the actuation catheter, causing the radial support arms and struts to fully distend. At this point, the touchdown detectors 648 are not in contact with any solid structures, and are fully extended with their radiolucent gaps visible on the imaging system. Once the deployment umbrella is distended, the entire assembly is pulled back against the area of the mitral valve 915. At least two touchdown detectors 648 are employed in a preferred embodiment according to the present invention. When all touchdown detectors show the disappearance of their intermediate, non-opaque, intermediate segments and are thus activated, then the deployment umbrella must be in contact with the solid tissue in the region of the mitral annulus/atrial tissue, and further implant deployment and adjustment may proceed. However, if any one touchdown sensor is not activated, and a radiolucent gap persists, then the device is not properly positioned, and must be repositioned before further deployment. Thus, the touchdown sensor system may assist in the deployment and adjustment of prosthetic devices by the delivery system according to the present invention. Once properly positioned, the operator rotates the actuation catheter in a prescribed clockwise or counterclockwise manner to engage the retention barbs on the implant into the tissue in the region of the mitral annulus/atrial tissue. Should re-positioning be required, a reverse motion would disengage the retention barbs from the annular/atrial tissue, and repositioning may be performed, again using the touchdown detectors for proper placement. Once firmly seated, the adjustment element(s) are operated to achieve the desired degree of annular reduction. Real-time trans esophageal echocardiography, intravascular echocardiography, intracardiac echocardiography, or other modalities for assessing mitral function may then be employed to assess the physiologic effect of the repair on mitral function, and additional adjustments may be performed. Once a desired result has been achieved, the release elements are activated to detach the implant from the deployment umbrella. The operator then retracts the actuation catheter and extends the housing sheath, collapsing the deployment umbrella and covering the components for a smooth and atraumatic withdrawal of the device from the heart and vascular system.

If desired, the adjustment elements may be left in position after the catheter components are withdrawn for further physiologic adjustment. In yet other embodiments according to the present invention, a catheter-based adjustment elements may subsequently be re-inserted though a percutaneous or other route. Such an adjustment element may be steerably operable by the operator, and may be provided with magnetic, electronic, electromagnetic, or laser-guided systems to allow docking of the adjustment element with the adjustable mechanism contained within the implant. In still other embodiments, the adjustment mechanism may be driven by implanted electromechanical motors or other systems, which may be remotely controlled by electronic flux or other remote transcutaneous or percutaneous methods.

In the case of pulmonic valve repair, initial catheter access is achieved through a peripheral or central vein. Access to the pulmonary valve is also achieved from below the valve once central venous access is achieved by traversing the right atrium, the tricuspid valve, the right ventricle, and subsequently reaching the pulmonic valve.

In yet other embodiments according to the present invention, catheter access to the left atrium can be achieved from cannulation of central or peripheral veins, thereby achieving access to the right atrium. Then a standard atrial trans-septal approach may be utilized to access the left atrium by creation of an iatrogenic atrial septal defect (ASD). In such a situation, the mitral valve may be accessed from above the valve, as opposed to the retrograde access described in Example 1. The implant and a reversed deployment umbrella may be utilized with implant placement in the atrial aspect of the mitral annulus, with the same repair technique described previously. The iatrogenic ASD may then be closed using standard device methods. Access to the aortic valve may also be achieved from above the aortic valve via arterial access in a similar retrograde fashion.

Figure 29:
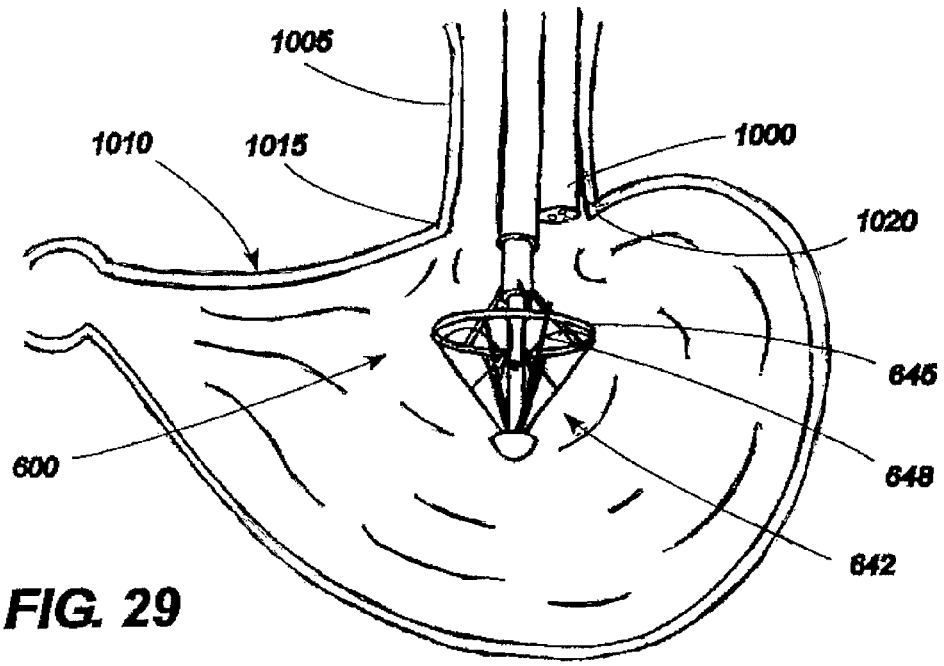
FIG. 29 is a schematic view showing the implant of FIG. 12 anatomically positioned at the gastroesophageal opening with the implant in a fully expanded state.
Figure 30:
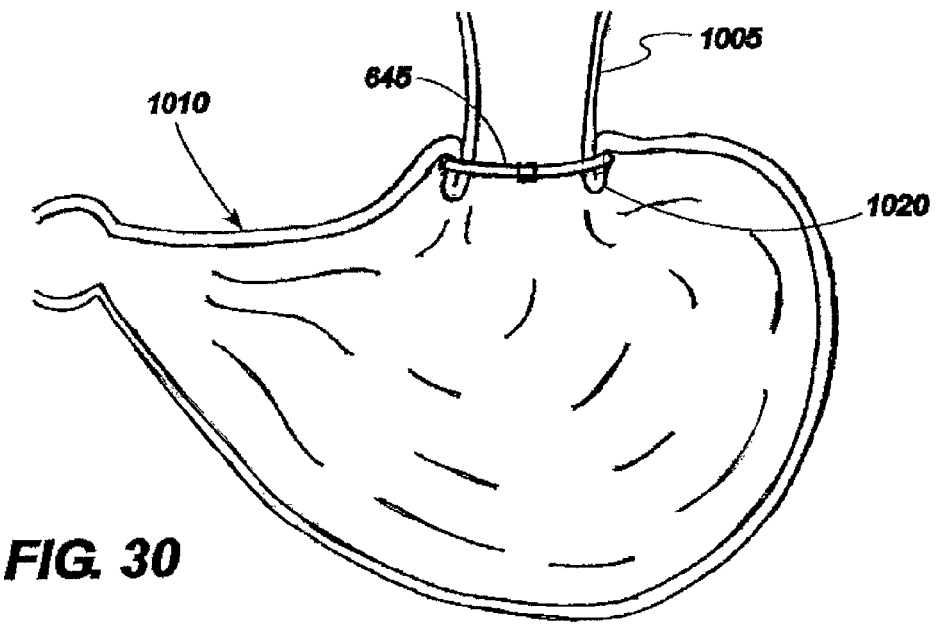
FIG. 30 is a schematic view showing the implant of FIG. 29 implanted to reduce the circumference of the gastroesophageal opening.

Other embodiments of the adjustable implant and methods according to the present invention include gastrointestinal disorders such as gastro-esophageal reflux disease (GERD), a condition in which the gastro-esophageal (GE) junction lacks adequate sphincter tone to prevent the reflux of stomach contents into the esophagus, causing classic heartburn or acid reflux. This not only results in discomfort, but may cause trauma to the lower esophagus over time that may lead to the development of pre-cancerous lesions (Barrett's esophagus) or adenocarcinoma of the esophagus at the GE junction. Surgical repair of the GE junction has historically been achieved with the Nissen Fundoplication, an operative procedure with generally good results. However, the Nissen procedure requires general anesthesia and a hospital stay. Utilizing the devices and methods according to the present invention, an adjustable implant would obviate the need for a hospital stay and be performed in a clinic or gastroenterologist's office. Referring now to FIGS. 29 and 30, an umbrella deployment device 600 with implant 645 is passed under guidance of an endoscope 1000, through the patient's mouth, esophagus 1005, and into the stomach 1010, where the deployment device 600 is opened with expansion of the implant 645 and touchdown detectors 648 with a color-coded or otherwise visible gap. The touchdown detectors are then engaged onto the stomach around the gastroesophageal junction 1015 under direct endoscopic control until all touchdown detectors 648 are visually activated. The implant is then attached to the stomach wall, 1020 the umbrella 642 is released and withdrawn, leaving behind the implant 645 and the adjustment elements. The implant is then adjusted until the desired effect is achieved, i.e., minimal acid reflux either by patient symptoms, pH monitoring of the esophagus, imaging studies, or other diagnostic means. If the patient should suffer from gas bloat, a common complication of gastroesophageal junction repair in which the repair is too tight and the patient is unable to belch, the implant can be loosened until a more desirable effect is achieved.

In various embodiments anticipated by the present invention, the implant body may be straight, curved, circular, ovoid, polygonal, or some combination thereof. In various embodiments anticipated by the present invention the implant may be capable of providing a uniform or non-uniform adjustment of an orifice or lumen within the body. The implant body may further completely enclose the native recipient anatomic site, or it may be provided in an interrupted form that encloses only a portion of the native recipient anatomic site. In still other embodiments of the present invention, the implant body may be a solid structure, while in yet other embodiments the implant body may form a tubular or otherwise hollow structure. In one embodiment of the present invention, the body may further be a structure with an outer member, an inner member, and optional attachment members. In such an embodiment, the outer member of the implant body may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or non-woven configuration. The outer member in such an embodiment also serves to house the inner member. In this embodiment, the inner member provides an adjustment means that, when operated by an adjustment mechanism, is capable of altering the shape and/or size of the outer member in a defined manner.

In alternate embodiments according to the present invention, the adjustment means may be located external to or incorporated within the outer member. In yet additional alternate embodiments contemplated by the present invention, the implant body may consist of an adjustment means without a separate outer member covering said adjustment means.

In various embodiments according to the present invention, the adjustment means may include a mechanism which may be threaded or non-threaded, and which may be engaged by the action of a screw or worm screw, a friction mechanism, a friction-detent mechanism, a toothed mechanism, a ratchet mechanism, a rack and pinion mechanism, or such other devices to permit discreet adjustment and retention of desired size a desired position, once the proper size is determined.

In yet other embodiments according to the present invention, the adjustment means may comprise a snare or purse string-like mechanism in which a suture, a band, a wire or other fiber structure, braided or non-braided, monofilament or multifilament, is capable of affecting the anatomic and/or physiologic effects of the implant device on a native anatomic recipient site upon varying tension or motion imparted to said wire or fiber structure by a surgeon or other operator. Such an adjustment means may be provided as a circular or non-circular structure in various embodiments. Changes in tension or motion may change the size and/or shape of the implant.

In various embodiments according to the present invention, the adjustment means may be a metallic, plastic, synthetic, natural, biologic, or any other biologically-compatible material, or combination thereof. Such adjustment means may further be fabricated by extrusion or other molding techniques, machined, or woven. Furthermore, in various embodiments of the present invention, the adjustment means may be smooth or may include slots, beads, ridges, or any other smooth or textured surface.

In various embodiments of the present invention, the implant body may be provided with one or more attachment members such as grommets or openings or other attachment members to facilitate attachment of the implant to the native recipient site. In alternate embodiments, the implant body may attach to or incorporate a mechanical tissue interface system that allows a sutureless mechanical means of securing the implant at the native recipient site. In still other alternate embodiments, sutures or other attachment means may be secured around or through the implant body to affix the implant body to the native recipient site. In yet other embodiments of the present invention, mechanical means of securing the implant body to the native recipient site may be augmented or replaced by use of fibrin or other biologically-compatible tissue glues or similar adhesives.

In additional various embodiments according to the present invention, the adjustable implant may be employed to adjustably enlarge or maintain the circumference or other dimensions of an orifice, ostium, lumen, or anastomosis in which a disease process tends to narrow or constrict such circumference or other dimensions.

In various embodiments according to the present invention, an adjustment mechanism may be provided to interact with the adjustment means to achieve the desired alteration in the size and/or position of the adjustment means. Such an adjustment mechanism may include one or more screws, worm-screw arrays rollers, gears, frictional stops, a friction-detent system, ratchets, rack and pinion arrays, micro-electromechanical systems, other mechanical or electromechanical devices or some combination thereof.

In some embodiments as contemplated by the present invention, an adjustment tool may be removably or permanently attached to the adjustment mechanism and disposed to impart motion to the adjustment mechanism and, in turn, to the adjustment means to increase or decrease the anatomic effect of the implant on the native recipient site.

In alternate embodiments according to the present invention, micromotor arrays with one or more micro-electromechanical motor systems with related electronic control circuitry may be provided as an adjustment means, and may be activated by remote control through signals convey by electromagnetic radiation or by direct circuitry though electronic conduit leads which may be either permanently or removably attached to said micromotor arrays.

In still other various embodiments according to the present invention, the adjustment mechanism may be provided with a locking mechanism disposed to maintain the position of the adjustment means in a selected position upon achievement of the optimally desired anatomic and/or physiologic effect upon the native recipient site and the bodily organ to which it belongs. In other embodiments, no special locking mechanism may be necessary due to the nature of the adjustment means employed.

In yet other alternate embodiments according to the present invention, the adjustment means and/or the outer member structure may be a pliable synthetic material capable of rigidification upon exposure to electromagnetic radiation of selected wavelength, such as ultraviolet light. In such embodiments, exposure to the desired electromagnetic radiation may be achieved by external delivery of such radiation to the implant by the surgeon, or by internal delivery of such radiation within an outer implant member using fiberoptic carriers placed within said outer member and connected to an appropriate external radiation source. Such fiberoptic carriers may be disposed for their removal in whole or in part from the outer implant member after suitable radiation exposure and hardening of said adjustment means.

The present invention also provides methods of using an adjustable implant device to selectively alter the anatomic structure and/or physiologic effects of tissues forming a passageway for blood, other bodily fluids, nutrient fluids, semi-solids, or solids, or wastes within a mammalian body. Various embodiments for such uses of adjustable implants include, but are not limited to, open surgical placement of said adjustable implants at the native recipient site through an open surgical incision, percutaneous or intravascular placement of said implants under visual control employing fluoroscopic, ultrasound, magnetic resonance imaging, or other imaging technologies, placement of said implants through tissue structural walls, such as the coronary sinus or esophageal walls, or methods employing some combination of the above techniques. In various embodiments as contemplated by the present invention, adjustable implants may be placed and affixed in position in a native recipient anatomic site by transatrial, trans-ventricular, trans-arterial, trans-venous (i.e., via the pulmonary veins) or other routes during beating or non-beating cardiac surgical procedures or endoscopically or percutaneously in gastrointestinal surgery.

Furthermore, alternate methods for use of an adjustable implant device may provide for the periodic, post-implantation adjustment of the size of the anatomic structure receiving said implant device as needed to accommodate growth of the native recipient site in a juvenile patient or other changes in the physiologic needs of the recipient patient.

Adjustment of the adjustable implants and the methods for their use as disclosed herein contemplates the use by the surgeon or operator of diagnostic tools to provide an assessment of the nature of adjustment needed to achieve a desired effect. Such diagnostic tools include, but are not limited to, transesophageal echocardiography, echocardiography, diagnostic ultrasound, intravascular ultrasound, virtual anatomic positioning systems integrated with magnetic resonance, computerized tomographic, or other imaging technologies, endoscopy, mediastinoscopy, laparoscopy, thoracoscopy, radiography, fluoroscopy, magnetic resonance imaging, computerized tomographic imaging, intravascular flow sensors, thermal sensors or imaging, remote chemical or spectral analysis, or other imaging or quantitative or qualitative analytic systems.

In one aspect, the implant/delivery system of the present invention comprises a collapsible, compressible, or distensible prosthetic implant and a delivery interface for such a prosthetic implant that is capable of delivering the prosthetic implant to a desired anatomic recipient site in a collapsed, compressed, or non-distended state, and then allowing controlled expansion or distension and physical attachment of such a prosthetic implant by a user at the desired anatomic recipient site. Such a system permits the delivery system and prosthetic implant to be introduced percutaneously through a trocar, sheath, via Seldinger technique, needle, or endoscopically through a natural bodily orifice, body cavity, or region and maneuvered by the surgeon or operator to the desired anatomic recipient site, where the delivery system and prosthetic implant may be operably expanded for deployment. When desirable, the implant/delivery system according to the present invention is also capable of allowing the user to further adjust the size or shape of the prosthetic implant once it has been attached to the desired anatomic recipient site. The delivery system according to the present invention is then capable of detaching from its interface with the prosthetic implant and being removed from the anatomic site by the operator. The delivery system and prosthetic implant may be provided in a shape and size determined by the anatomic needs of an intended native recipient anatomic site within a mammalian patient. Such a native recipient anatomic site may be a heart valve, the esophagus near the gastro-esophageal junction, the anus, or other anatomic sites within a mammalian body that are creating dysfunction that might be relieved by an implant capable of changing the size and shape of that site and maintaining a desired size and shape after surgery.

In various embodiments contemplated by the present invention, the delivery system may be a catheter, wire, filament, rod, tube, endoscope, or other mechanism capable of reaching the desired recipient anatomic site through an incision, puncture, trocar, or through an anatomic passageway such as a vessel, orifice, or organ lumen, or trans-abdominally or trans-thoracically. In various embodiments according to the present invention, the delivery system may be steerable by the operator. The delivery system may further have a delivery interface that would retain and convey a prosthetic implant to the desired recipient anatomic site. Such a delivery interface may be operably capable of distending, reshaping, or allowing the independent distension or expansion of such a prosthetic implant at the desired recipient anatomic site. Furthermore, such a delivery interface may provide an operable means to adjust the distended or expanded size, shape, or physiologic effect of the prosthetic implant once said implant has been attached in situ at the desired recipient anatomic site. In various embodiments according to the present invention, such adjustment may be carried out during the procedure in which the implant is placed, or at a subsequent time. Depending upon the specific anatomic needs of a specific application, the delivery interface and the associated prosthetic implant may be straight, curved, circular, helical, tubular, ovoid, polygonal, or some combination thereof. In still other embodiments of the present invention, the prosthetic implant may be a solid structure, while in yet other embodiments the prosthetic implant may form a tubular, composite, or otherwise hollow structure. In one embodiment of the present invention, the prosthetic implant may further be a structure with an outer member, an inner member, and optional attachment members. In such an embodiment, the outer member of the prosthetic implant may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or non-woven configuration. The outer member in such an embodiment also serves to house the inner member. In this embodiment, the inner member provides an adjustment means that, when operated by an adjustment mechanism, is capable of altering the shape and/or size of the outer member in a defined manner.

In some embodiments according to the present invention, at least some portions of the adjustable inner or outer member may be elastic to provide an element of variable, artificial muscle tone to a valve, sphincter, orifice, or lumen in settings where such variability would be functionally valuable, such as in the treatment of rectal incontinence or vaginal prolapse.

In various embodiments according to the present invention, the delivery interface would have an attachment means to retain and convey the prosthetic implant en route to the native anatomic recipient site and during any in situ adjustment of the prosthetic implant once it has been placed by the operator. Such an attachment means would be operably reversible to allow detachment of the prosthetic implant from the delivery interface once desired placement and adjustment of the prosthetic implant has been accomplished.

Figure 31:
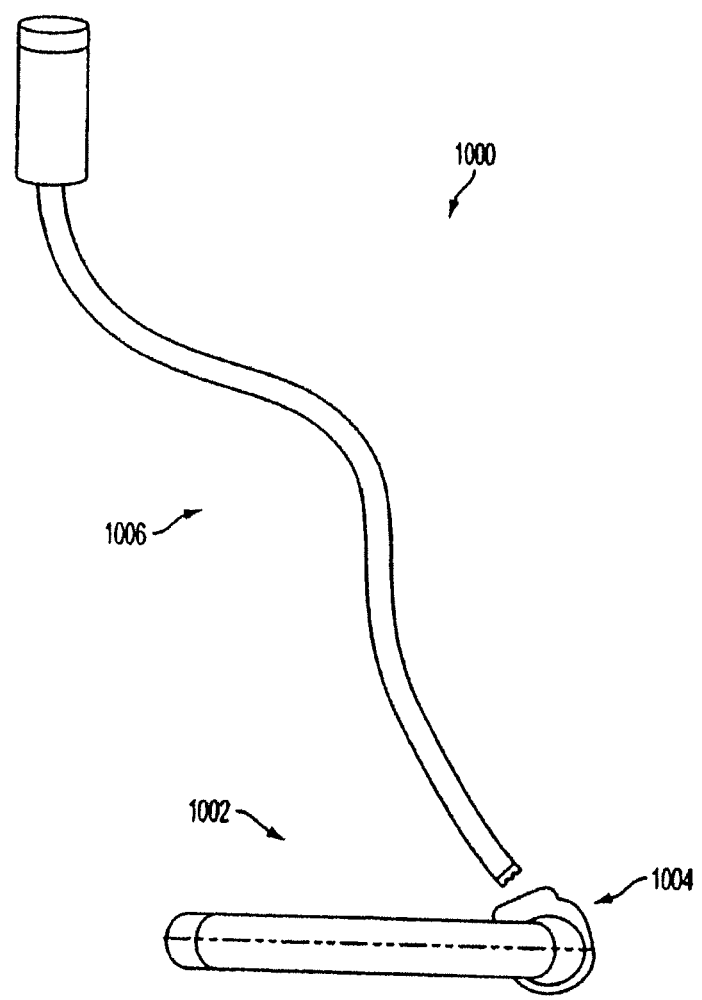
FIG. 31 is a schematic view of an embodiment of an implantable device of the present invention.

In one embodiment of the present invention, illustrated in FIG. 31, an implantable device system 1000 for controlling at least the size or shape of an anatomical structure or lumen includes an implantable device 1002 and an adjustment tool 1006. The anatomical structure or lumen is an anatomic site with dysfunction that can be relieved by the implantable device 1002 to change a size or shape of the anatomic site.

The implantable device 1002, in one exemplary embodiment, has a diameter no larger than 3.5 mm. In another embodiment the implantable device 1002 is configured to have variable size relative to its placement at an annulus of a heart valve. The implantable device 1002 has an adjustable member 1004 configured to adjust the dimensions of the implantable device 1002. In one embodiment, the torqueable adjustment tool 1006 provides adjustment of the dimensions of the implantable device 1002. The adjustable member 1004, in some embodiments, may be oriented to receive the adjustment tool from a direction generally perpendicular to the primary plane defined by the implant device 1002. Such an orientation is advantageous for intravenous access of the tool and in situ adjustment of the implant device 1002. The implantable device 1002 can have a configuration where there are different pulling rates at different sections of the implantable device 1002. The implantable device 1002 may optionally include a flexible tube (1032, FIG. 38) and an outer fabric sheath (810, FIGS. 25 and 26), which are not shown in the subsequent figures for clarity. The outer fabric sheath can be sutured, stapled, clipped, coiled, or otherwise affixed to anatomic tissue in a desired location. Generally the desired location is considered to be the internal surface of the area to be controlled, such as (for example) an interior wall of an organ, artery, or other internal anatomic passage. Also, while the implantable device 1002 is generally shown in the subsequent figures to have a "D"-shaped configuration, it should be understood that other shapes can be used in accordance with embodiments of the present invention.

Still referring to FIG. 31, in certain embodiments, the adjustment tool 1006 is at least partially hollow, and in one specific embodiment at least 50% hollow. The adjustment tool 1006 may be an elongated tool, which has a proximal end and a distal end releasably attached to the adjustable member 1004 of implantable device 1002. The adjustment tool 1006 may extend from its distal end coupled to the adjustable member 1004 to a control interface (e.g., handle) at the proximal end located preferably outside of the patient's body. The adjustment tool 1006, when coupled to the adjustable member 1004 of implantable device 1002, can provide a preferential shape change of the implantable device 1002 in planar and non-planar directions. The adjustment tool 1006 can adjust the implantable device 1002 in terms of narrowing or widening the dimensions of the implantable device 1002.

Figure 32A:
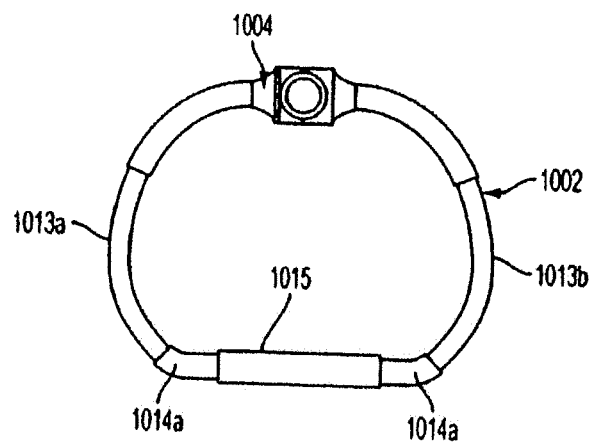
FIG. 32A is a schematic view of another embodiment of an implantable device of the present invention.
Figure 32B:
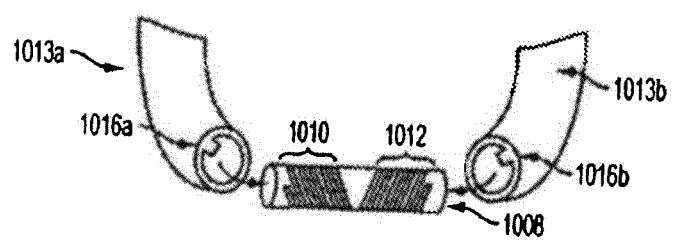
FIG. 32B is a schematic view of a threaded member in an embodiment of an implantable device of the present invention.

FIG. 32A is a schematic of the implant device 1002 without showing an optional flexible outer tube and fabric sheath. The implantable device includes an adjustable member 1004 and adjustable tube portions 1013*a* and 1013*b*, which slide within hollow tube portions 1014*a* and 1014*b*, and retaining tube 1015. FIG. 32B is a schematic of a disassembled portion of implantable device 1002 with retaining tube 1015 removed. As shown in FIG. 32B, in various embodiments, the implantable device 1002 includes a threaded rod 1008 threaded with right-hand helical grooves 1010 and left-hand helical grooves

1012. Other embodiments may include a threaded rod 1008 with helical grooves in a single direction (e.g., all right-hand grooves or all left-hand grooves). Threaded rod 1008 may be a rigid material such as titanium, stainless steel, or a polymer. Adjustable tube portions 1013a and 1013b enclose at least a portion of grooves 1010 and 1012 so that pins 1016a, 1016b or protuberances on the inside diameter of the adjustable tube portions 1013a, 1013b are engaged by the grooves 1010 and 1012, respectively. In other embodiments, pins 1016a, 1016b may be replaced by threads along the inside diameter of the adjustable tube portions 1013a, 1013b. Helical grooves 1010 and 1012 may be single channels or multiple channels to engage single pins 1016a, 1016b or multiple pins. Hollow tube portions 1014a, 1014b are relatively rigid to maintain curvature of the adjustable tube portions 1013a, 1013b regardless of the adjustment position.

The implantable device 1002 can have a coating including, but not limited to, heparin, and antibiotic, collagen, and an agent that promotes tissue in growth, PGLA, a de-calcification agent and the like. The implantable device 1002 can be made of a variety of materials including, but not limited to, a shape memory alloy (SMA), a shape memory polymer (SMP), titanium, stainless steel, polymer, a suture-based material, a biological material and the like.

Figure 33:
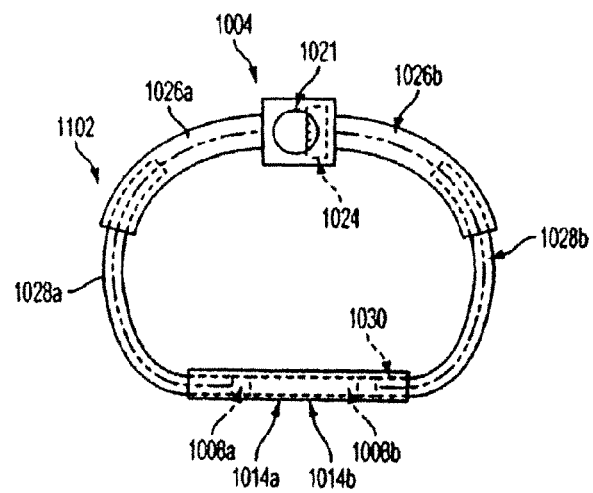
FIG. 33 is a schematic view of an embodiment of an implantable device of the present invention with an outer tubing and an inner tubing in a relative first position.
Figure 34:
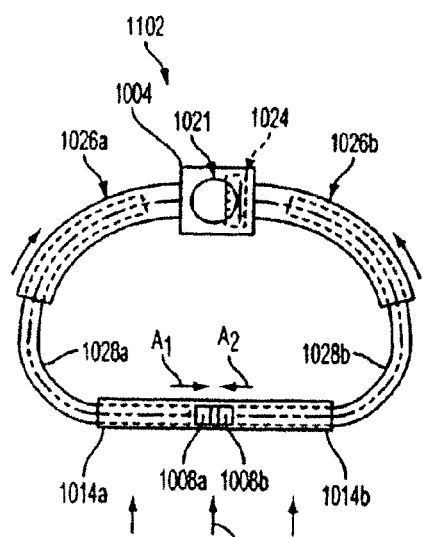
FIG. 34 is a schematic view of an embodiment of an implantable device of the present invention with an outer tubing and an inner tubing in a relative second position.
Figure 35:
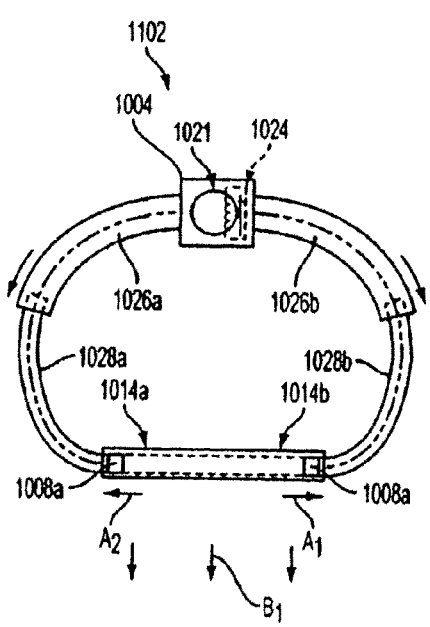
FIG. 35 is a schematic view of an embodiment of an implantable device of the present invention with an outer tubing and an inner tubing in a relative third position.
Figure 36:
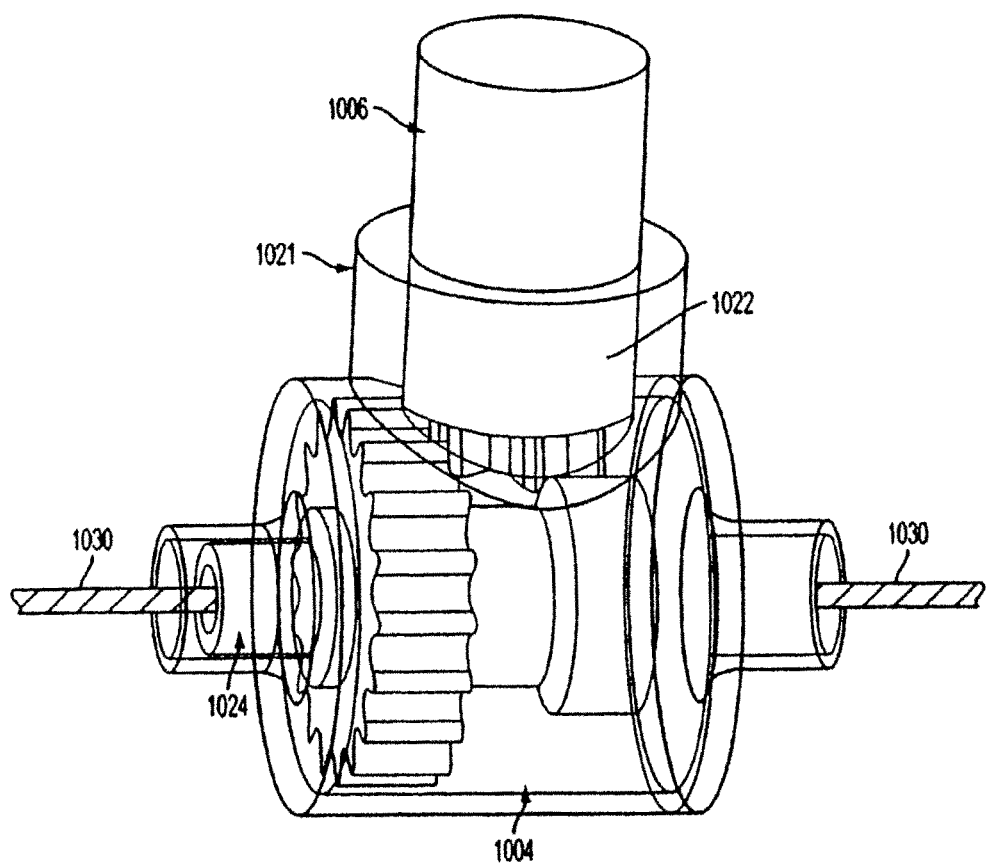
FIG. 36 is a schematic view of an embodiment of an adjustable member of the present invention, with the distal tip of the adjustment tool coupled to the adjustment member.
Figure 37:
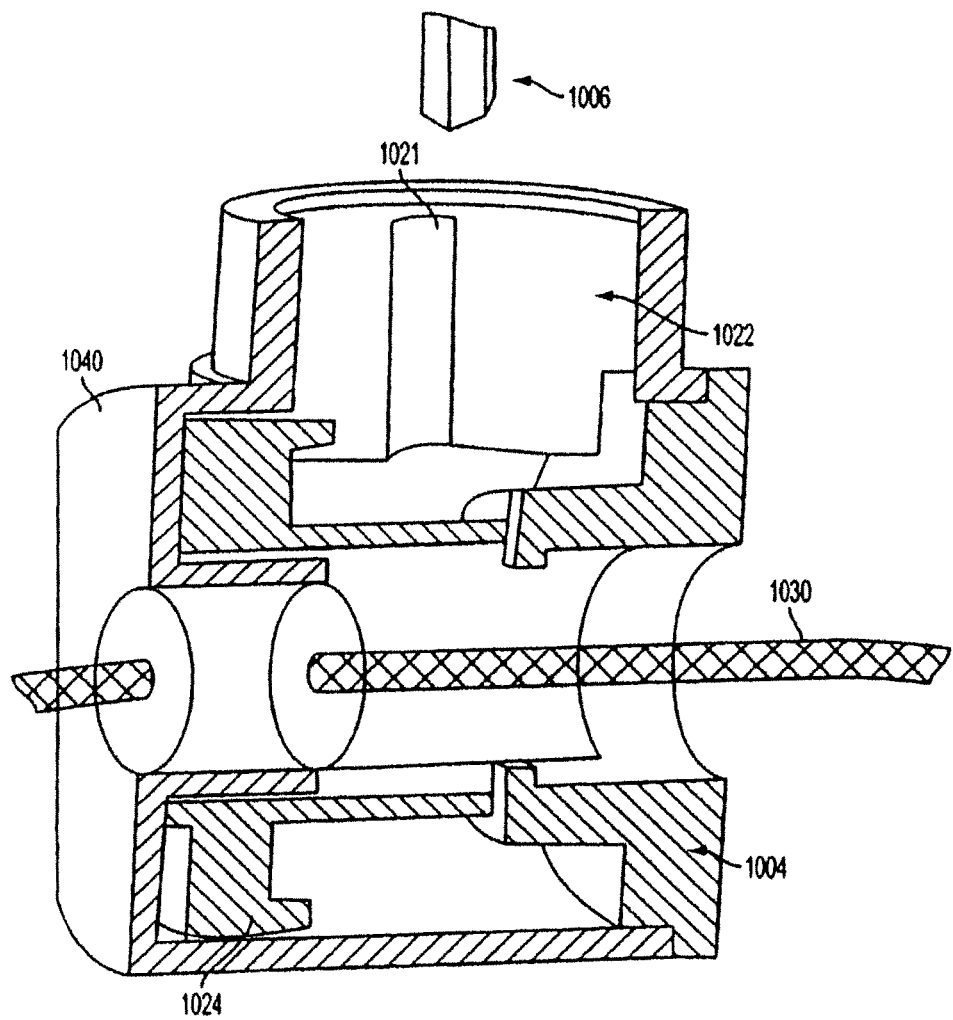
FIG. 37 is a schematic view of an embodiment of an adjustment member of the present invention having an integrated pinion gear.

In another embodiment of the present invention, illustrated in FIGS. 33 through 37, the adjustable member 1004 provides translated motion through rotation. FIGS. 33 through 35 illustrate a theory of operation of an embodiment of the present invention, while FIGS. 36 and 37 shown details of the adjustment member 1004.

Referring to now FIG. 33, adjustable member 1004 of implantable device 1102 is shown including a docking port 1021 to receive the distal tip of the adjustment tool 1006 (FIG. 31). In this embodiment, implant device includes a set of inner tubing 1028a, 1028b and a set of outer tubing 1026a, 1026b that can move relative to each other. The ends of the inner tubing 1028a, 1028b that do not engage the outer tubing 1026a, 1026b are secured to a set of hollow tubing 1014a, 1014b so that the inner tubing 1028a, 1028b does not move relative to the hollow tubing 1014a, 1014b. Although hollow tube portions 1014a, 1014b may be separate pieces that are permanently abutted when assembled, in some embodiments, the hollow tube portions 1014a, 1014b may be formed from a single tubing piece. An inner cable 1030 passes through the various tubing. Thus, the rigidity of the hollow tubing can be used to maintain the adjustable implant 1102 shape in certain dimensions so that adjustment of the device can be restricted to a preferred dimension, for example, an anterior-posterior dimension.

As shown in more detail in FIGS. 36 and 37, adjustable member 1004 may also include a pinion gear 1022 (which may be integral to a docking port 1021) and a crown gear 1024. FIG. 36 provides an isometric view of the adjustable member 1004, and FIG. 37 provides a cut-away view of the adjustable member 1004. As can be seen in the figures, the pinion gear 1022 engages the crown gear 1024. In some embodiments, the pinion gear 1022 may be eliminated from adjustable member 1004, and the distal tip of the adjustment tool 1006 may serve as the pinion gear when the tool is coupled to the docking port 1021. When coupled to the docking port 1021, the adjustment tool 1006 can rotate the pinion gear 1022.

Referring back to FIG. 33, the implantable device 1102 is shown generally at the middle of its adjustment range. Outer tubing 1026a, 1026b is affixed to the adjustable member 1004 and extends along a portion of the circumference of implantable device 1102. Inner tubing 1028a, 1028b is affixed to hollow tubing 1014a, 1014b, respectively. Similar to the single threaded rod 1008 of FIG. 32B, threaded rods 1018a, 1018b sit inside the hollow tubing 1014a, 1014b and are threadedly engaged therewith. Threaded rods 1018a, 1018b may be a rigid material such as titanium, stainless steel, or a polymer. Hollow tube portions 1014a, 1014b enclose the threaded rods 1018a, 1018b such that rotation of the threaded rods 1018a, 1018b causes them to move axially within the hollow tube portions 1014a, 1014b. The threaded rod 1018a may have right-handed threads, and the threaded rod 1018b may have left handed threads. Other embodiments may include threaded rods 1018a, 1018b with threads in a single direction (e.g., all right-hand grooves or all left-hand threads).

The crown gear 1024, and one end of each threaded rod 1018a, 1018b are all attached to an inner cable 1030. Inner cable 1030 may be a cable or tube of any material with sufficient flexibility to conform to a shape of the implantable device 1102 while translating torque. For example, suitable material for inner cable 1030 may include titanium or stainless steel. As shown more clearly in FIGS. 36 and 37, the rotation of crown gear 1024 imparts rotation to cable 1030 in the same direction.

Referring to FIG. 34, when the handle of adjustment tool 1006 (not shown in this figure) is rotated clockwise in docking port 1021, it causes clockwise rotation of the pinion gear 1022 (in FIG. 36). Rotation of the pinion gear 1022 in turn rotates crown gear 1024. The rotation of crown gear 1024 causes rotation of inner cable 1030, which imparts rotational movement to each threaded rod 1018a, 1018b. The rotation applied to the threaded rods 1018a, 1018b causes them to advance into their respective hollow tubing 1014a, 1014b in the directions $A_1$, $A_2$ shown. As shown in FIG. 34, when threaded rods 1018a, 1018b advance toward the middle of the hollow tubing 1014a, 1014b the overall circumference of the implant device 1002 is reduced. Advancing the threaded rods 1018a, 1018b drives the inner cable 1030 into the hollow tubing 1014a, 1014b. Translation of inner cable 1030 into the hollow tubing 1014a, 1014b causes the hollow tubing 1014a, 1014b to move towards adjustable member 1004 in the direction $B_1$ shown. Inner tubing 1028a, 1028b slides into outer tubing 1026a, 1026b to accommodate movement of the inner cable 1030.

Referring to FIG. 35, the handle of adjustment tool 1006 (not shown in this figure) is rotated counter-clockwise in docking port 1021 to cause counter-clockwise rotation of the pinion gear 1022 (FIG. 36). Rotation of the pinion gear 1022, in turn rotates crown gear 1024. The rotation of crown gear 1024 causes rotation of inner cable 1030, which imparts rotational movement to each threaded rod 1018a, 1018b. The rotation applied to the threaded rods 1018a, 1018b causes them to begin to withdraw from their respective hollow tubing 1014a, 1014b in the directions $A_2$, $A_1$ shown. As shown in FIG. 35, as threaded rods 1018a, 1018b withdraw from the middle of the hollow tubing 1014a, 1014b the overall circumference of the implant device 1002 is increased. Withdrawal of the threaded rods 1018a, 1018b pushes the inner cable 1030 out of the hollow tubing 1014a, 1014b. Translation of inner cable 1030 out of the hollow tubing 1014a, 1014b causes the hollow tubing 1014a, 1014b to move away from adjustable member 1004 in the direction $B_2$ shown. Inner tubing 1028a, 1028b telescopes out of outer tubing 1026a, 1026b to accommodate movement of the inner cable 1030.

Figure 38:
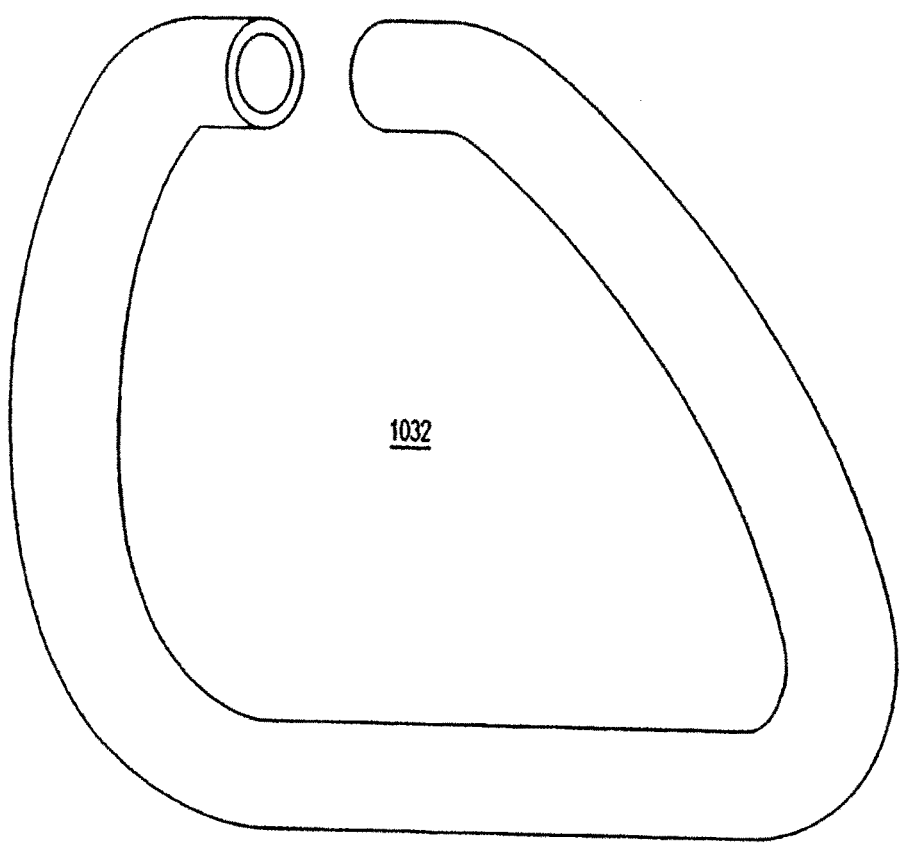
FIG. 38 is a schematic view of an embodiment of a flexible tube cover for an implant device.

The inner tubing 1028a, 1028b, the outer tubing 1026a, 1026b, and the hollow tubing 1014a, 1014b may be covered by a flexible tube 1032, such as a silicone tube, shown in FIG. 38. In one embodiment, outer flexible tube 1032 is provided with no seam in the axial direction of the tube to allow for better tissue ingrowth after the implant procedure. In other embodiments inner tubing 1028a, 1028b may be eliminated, as shown in FIG. 39.

Figure 39:
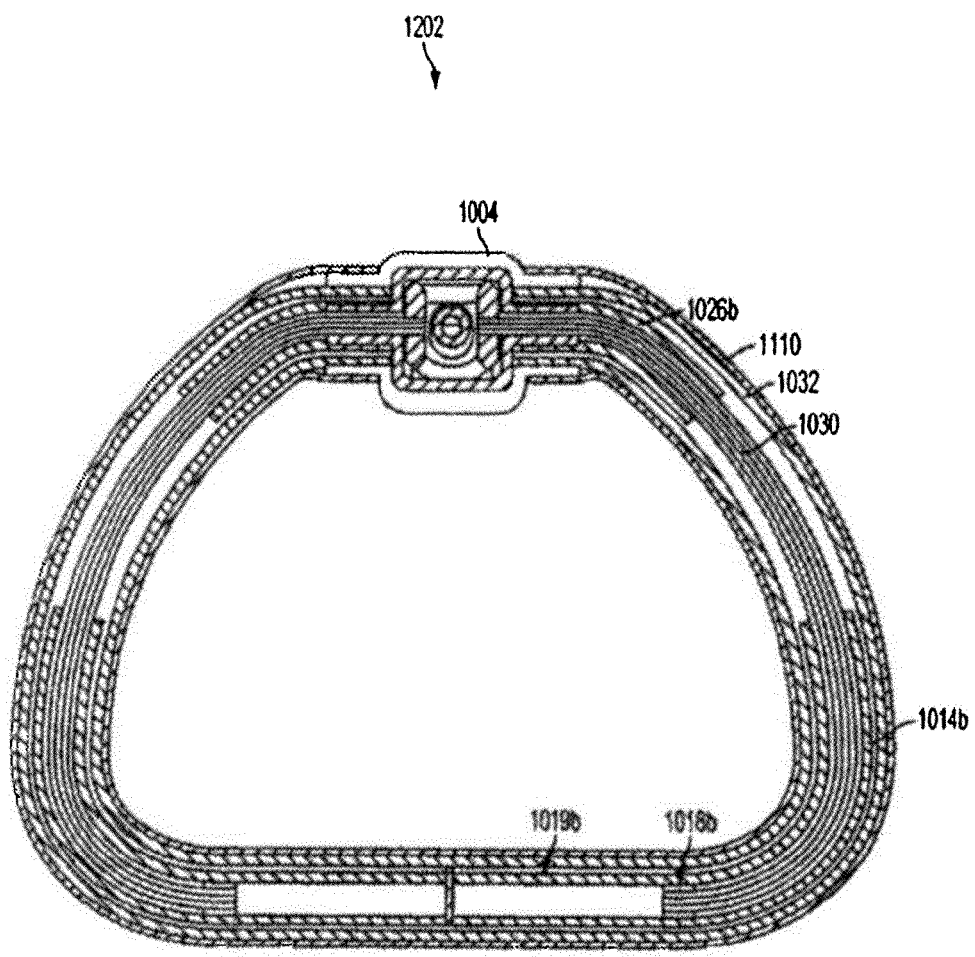
FIG. 39 is a cross-section view of an assembled embodiment of an adjustable implant device.

FIG. 39 provides an assembled cross-section view of an implantable device 1202 according to an embodiment of the invention. The implant device includes the adjustable member 1004, the outer tubing 1026a, 1026b, the hollow tubing 1014a, 1014b, the inner cable 1030, and the threaded rods 1018a, 1018b as discussed in relation to FIGS. 33-35. As shown in FIG. 39, hollow tubing 1014a, 1014b may extend further along the length of inner cable 1030 than shown in other embodiments of FIGS. 33-35 to better maintain a preferred shape of the implant. Hollow tubing 1014a, 1014b may be threaded to receive the threaded rods 1018a, 1018b; or hollow tubing may optionally include a threaded insert (spar 1019a, 1019b) affixed to the inner diameter of hollow tubing 1014a, 1014b. In operation, as previously described, an adjustment tool may impart motion to the adjustable member 1004. Gears in the adjustable member translate motion to the inner cable 1030 that, in turn translate motion to the attached threaded rods 1018a, 1018b. Depending on the direction of rotation, rotation of threaded rods 1018a, 1018b causes the threaded rods 1018a, 1018b to be drawn toward or away from the middle of the hollow tubing 1014a, 1014b, thus reducing or increasing the overall circumference of the implant device 1002. The flexible outer tube 1032 and a seal jacket 1100 (also shown in FIG. 40) encapsulate the device so that no moving parts are exposed. The flexible outer tube 1032 provide sufficient rigidity to maintain a generally planar dimension, while allowing the device to adjust shape generally in a preferred dimension, such as the anterior-posterior dimension. As shown in FIG. 39, the flexible outer tube 1032 may be further covered by an outer fabric sheath 1110 or thin sewing cuff. Elimination of the inner tubing (1028a, 1028b of FIG. 35) eliminates the need for telescoping parts and prevents the possibility of telescoping tubes being sutured or clipped together during attachment of the implant.

Figure 40:
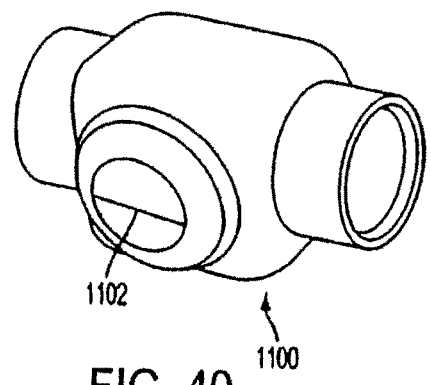
FIG. 40 is a schematic view of an embodiment of a seal jacket for an adjustable member.

Referring to FIG. 40, the adjustable member 1004 can include a seal jacket 1100. FIG. 40 shows an embodiment of the seal jacket 1100. The seal jacket 1100 may include a cover 1102 for the docking port 1021 (FIG. 33) of the adjustable member 1004. The cover 1102 may be in the form of a slit septum, flaps, elastic material or the like. The seal jacket cover 1102 may be included as part of a seal jacket 1100 that covers the entire housing of the adjustable member 1004 or a separate piece. In one embodiment, the seal jacket 1100 may be secured to the flexible tube 1032. The seal jacket 1100 and flexible tube 1032 may be secured by an adhesive bond, a wrap, sutures, or the like. The cover 1102 provides access for an adjustment tool to couple to the docking port, while reducing the possibility of thrombus. In some embodiments, seal jacket cover 1102 and/or the seal jacket 1100 may be made of silicone, and covered by a polyester sewing layer or fabric sheath (e.g., 1110 of FIG. 39). In various embodiments, the seal jacket fits over the housing of the adjustable member 1004 that includes a crown gear coupled to a cable, can provide pinion access, and the like. In operation, the distal tip of an adjustment tool passes through the cover 1102 to engage the rotatable gear of adjustable member 1004.

Figure 41:
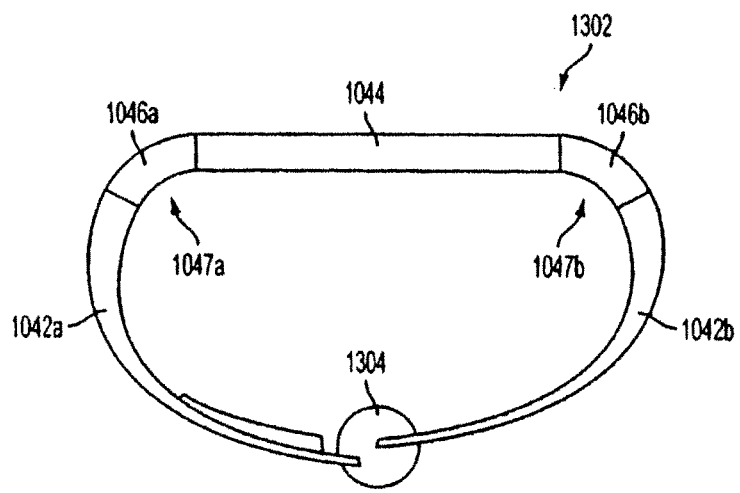
FIG. 41 is a schematic view of an embodiment of an adjustment band in the implantable member of the present invention.

FIG. 41 shows an embodiment of implantable device 1302 including a first adjustment band 1042a and a second adjustment band 1042b. The first and second adjustment bands 1042a, 1042b can be overlapped, and the amount of overlap is effected by how the implantable device 1302 is sized. The first and second bands 1042a, 1042b can be slidable relative to each other. An adjustable member 1304 is coupled to the first band 1042a and the second band 1042b, and pulls or pushes them toward or away from each other. The first band 1042a and the second band 1042b can have flexible portions 1046a, 1046b configured to create a flexible zone at the primary bend regions 1047a, 1047b. The flexible portions 1046a, 1046b can have varying lengths and may also include one or more rigid portions 1044. These rigid portions 1044 can include welded braids or bands, or have a higher durometer material than the flexible portions 1046a, 1046b. The flexible portions 1046a, 1046b and rigid portions 1044 may be part of the same material as the first and second bands 1042a, 1042b, or one or more portions may be separate material that is joined to form continuous piece.

The first and second bands 1042a, 1042b can have different sizes or the same sizes. In one specific embodiment, the first and second bands 1042a, 1042b are about 0.5 to 3 mm in thickness and about 5 to 0 mm in width. The first and second bands 1042a, 1042b can be made of a variety of materials including, but not limited to, an SMA, an SMP, titanium, stainless steel, polymer, a suture-based material, a biological material and the like. In one embodiment, the first and second bands 1042a, 1042b include a plurality of band layers. At least a portion of the first and second bands 1042a, 1042b may have superelastic properties. Implant 1302 may include a flexible, extruded outer layer (not shown) or hollow tube, such as flexible tube 1032 of FIG. 38, to encase the structure formed by the first and second bands 1042a, 1042b flexible portions 1046a, 1046b, and rigid portions 1044. The parts of the first and second bands 1042a, 1042b, that extend past adjustable member 1304 can be contained within the hollow interior of the outer layer.

Figure 42:
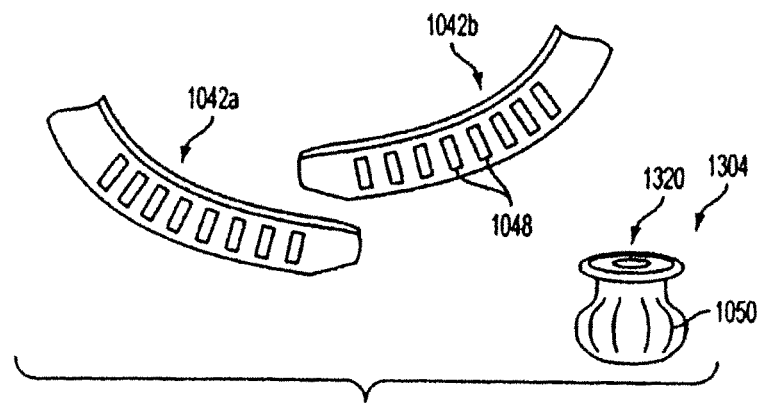
FIG. 42 is a disassembled schematic view of part of the adjustment band and adjustment member of FIG. 41.

FIG. 42 provides a more detailed schematic view of the unassembled adjustment bands and adjustment member of FIG. 41. The first and second bands 1042a, 1042b may include a series of adjustment stops 1048. Adjustment stops may be in the form of holes, detents, dimples, ridges, teeth, raised elements, other mechanical features or the like. These holes 1048 on each of the bands 1042a, 1042b are coupled to an adjustable member 1304. The adjustable member 1304 may be generally cylindrical (such as a spool) with a series of teeth 1050 or protrusions radially positioned to engage the adjustment stops 1048. Adjustable member 1304 may also include a docking port 1320 to receive an adjustment tool to trigger rotational movement of the adjustable member.

Figure 43:
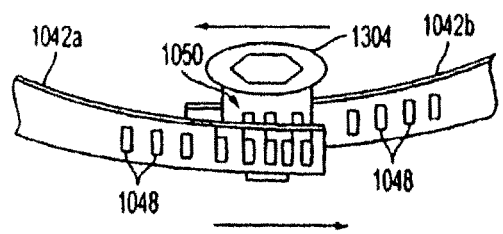
FIG. 43 is an assembled view of the adjustment band and adjustment member of FIG. 42.

FIG. 43 provides an assembled view of the adjustment band and adjustment member of FIG. 42. When mounted in a housing (not shown in FIG. 43), the adjustable member 1304 may be mounted on an axis to allow for rotational movement. The first and second bands 1042a, 1042b pass on either side of adjustable member 1304 so that the teeth 1050 engage the adjustment stops 1048 in each of the bands 1042a, 1042b. Rotating the adjustable member in turn tightens or loosens the bands.

Figure 44:
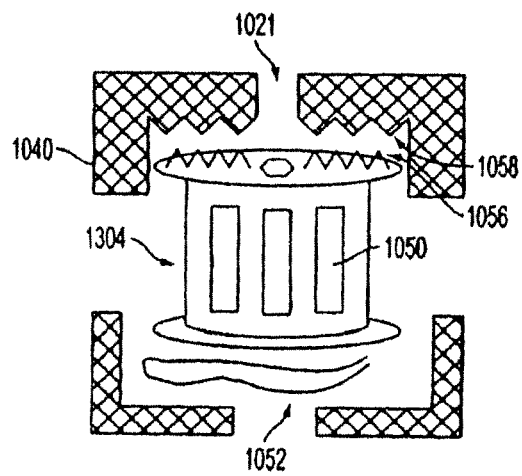
FIG. 44 is a schematic view of an embodiment of the gearbox for the adjustment band of FIG. 41.

FIG. 44 is a cut-away view of an embodiment of the gearbox for the adjustment band of FIG. 41. In this embodiment, the adjustable member 1304 rests on a spring 1052 inside a housing 1040 for the adjustable member. The housing 1040 includes access and guidance for the first and second bands (1042a, 1042b of FIG. 43) to couple with the teeth 1050 of the adjustable member 1304. The spring 1052 forces the adjustable member 1304 upward so that teeth 1056 on the top of the adjustable member 1304 engage with teeth 1058 on the inside upper surface of the housing 1040. Engagement of the adjustable member teeth 1056 with the housing teeth 1058 locks the adjustable member 1304 in place to prevent rotational movement. Downward force, applied for example by an adjustment tool, against the spring 1052 disengages the teeth 1056 and 1058 so that the adjustable member 1304 can be rotated to adjust the size or shape of implantable device 1302.

Figure 45:
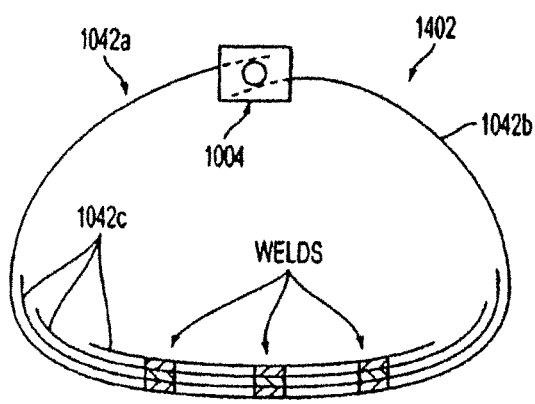
FIG. 45 is a schematic view of an embodiment of the implantable device of the present invention with a sliding band that can be opened and closed to effect a preferential shape change.

In another embodiment, FIG. 45 provides a schematic view of an implantable device 1402 of the present invention with a plurality of sliding bands that can be opened and closed to effect a shape change. As with the previous embodiments of FIGS. 41-44, the first and second bands 1042a, 1042b pass on either side of adjustable member 1304 so that the teeth 1050 engage the adjustment stops 1048 in each of the bands 1042a, 1042b. Additional bands 1042c may be incorporated to increase stiffness at different areas of the implant device 1402 to provide preferential shape change. The additional bands 1042c may be secured to the first and second bands 1042a, 1042b using welds 1043, adhesive or other mechanical techniques known in the art.

Figure 46:
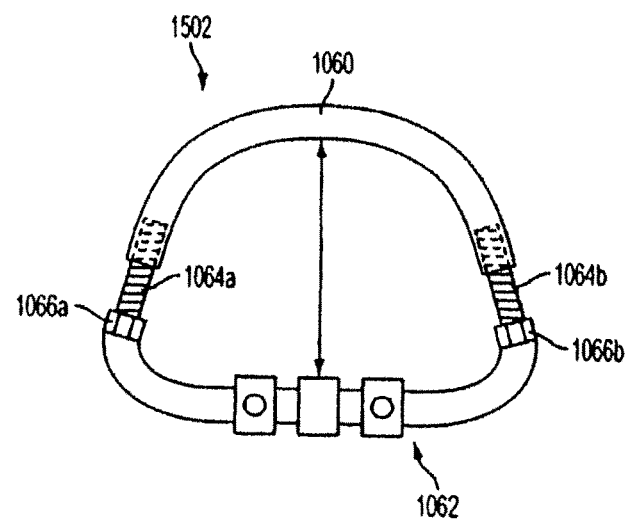
FIG. 46 is a schematic view of an embodiment of the implantable device of the present invention with two adjustable screws used to achieve different pulling rates.

As illustrated in FIG. 46, in one embodiment, an implantable device 1502 has an anterior portion 1060, a posterior portion 1062 and dual threads that provide preferential adjustment of one side or the other of implantable device 1002. The implantable device 1502 has two independently adjustable threaded portions 1064a, 1064b used to achieve different pulling rates and/or lateral dimensions. The adjustable threaded portions 1064a, 1064b can be connected to one or more adjustable member 1004 of the implantable device 1502 and positioned at either the posterior or anterior portions of the implantable device 1502. In one embodiment, the posterior portion 1062 may be a rigid member which includes threaded hex screws 1066a, 1066b, internal threads or similar structures. In one embodiment, the hex screws 1066a, 1066b are attached in a manner that allows rotation of the hex screws so that the threads may engage adjustable threaded portions 1064a, 1064b. Rigid posterior portion 1062 may include one or more of adjustable members 1004 that can receive a tool to impart rotational motion through an inner tube or cable to one or more of hex screws 1066a, 1066b, as described above. Anterior portion 1060 may be a flexible tube to accommodate shape change as the anterior and posterior portions 1060, 1062 move relative to each other.

In another embodiment, differently pitched threads or other mechanisms may be used to provide non-symmetrical shape change of the implant device. For example, referring to FIG. 46, wider threads on threaded portion 1064b, in relation to the threads of threaded portion 1064a, would allow an adjustable member 1004 to expand or contract the implant 1502 more rapidly on the side of threaded portion 1064b to provide preferential shape change for a selected region while using a single adjustable member.

Figure 47:
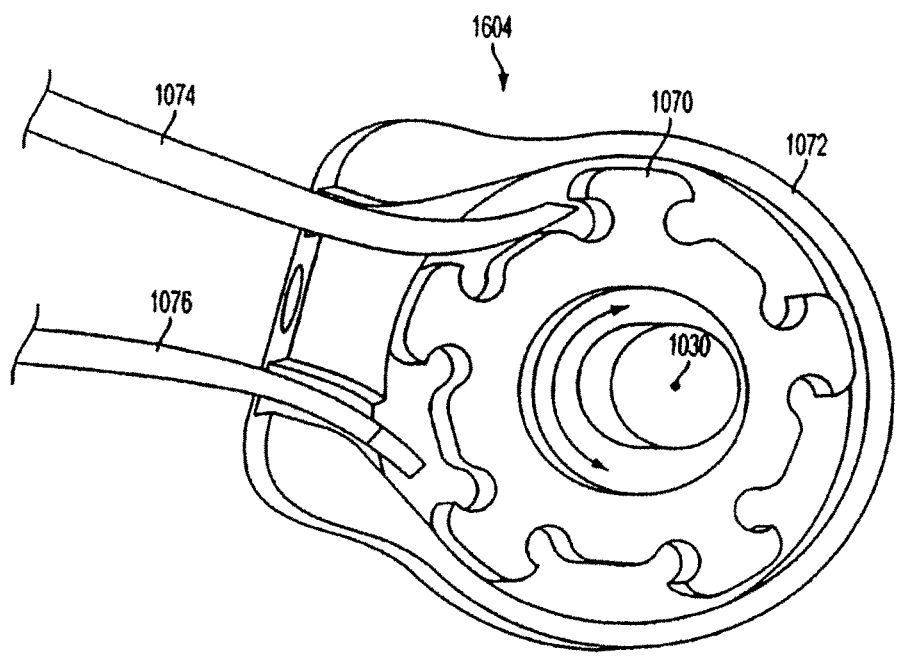
FIG. 47 is a schematic view of an embodiment of the implantable device of the present invention with reciprocating motion and a clover gear.

FIG. 47 is a schematic view of an embodiment of an adjustable member 1604 for an implantable device. An adjustment tool may impart reciprocating motion to the adjustable member 1604 that includes a clover gear 1070 mounted in a housing 1072. The inner cable 1030 (FIG. 33) of the implantable device, for example, is affixed to the clover gear 1070 such that rotation of the clover gear transmits torque through the inner cable 1030 to a screw or other adjustable portion of the implantable device as previously disclosed. In this embodiment, the adjustment tool can provide reciprocating action to provide for adjustment. The adjustable member takes an axial force applied to the control portion at the proximal end of the adjustment tool and converts it to a rotational force applied to the inner cable 1030 of the implantable device. Reciprocating axial force may be provided from an adjustment tool by using spring-mounted buttons pressed by the user. Pressing a first button may transmit a downward axial motion to a first ribbon 1074 which engages the clover gear 1070 to cause clockwise rotation of the clover gear 1070. A spring or other return force pushes the first ribbon back to its original position after each click or press of the button. Similarly, pressing a second button may transmit a downward axial motion to a second ribbon 1076 that engages the clover gear 1070 to cause counter-clockwise rotation of the clover gear 1070.

In another embodiment, the adjustment tool provides coarse adjustment and fine adjustment. This varied adjustment can be achieved with the adjustment tool having screws with different threads.

Figure 48:
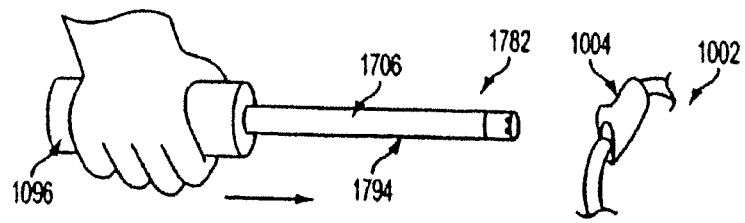
FIG. 48 is a schematic view of an embodiment of the implantable device system of the present invention with an adjustment tool having high column strength and stiffness.

FIG. 48 provides a schematic view of an embodiment of the implantable device system 1000 including an adjustment tool 1706 with high column strength and stiffness. The adjustment tool 1706 has a shaft 1794 and a handle 1096 with sufficient column strength to ensure a downward axial force on the handle 1096 provides proper engagement with the adjustable member 1004 of the implantable device 1002. The handle 1096 may be a grip-like handle, as shown, or a smaller pen-type handle. The adjustment tool 1706 can include mechanical locking at the distal region 1782 to lock with the adjustable member 1004. The mechanical locking is configured to provide engagement and disengagement tactile feel to the physician.

Figure 49:
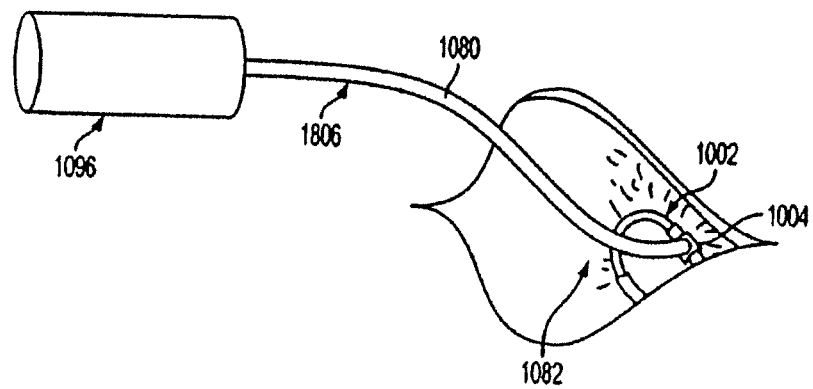
FIG. 49 is a schematic view of an embodiment of the implantable device of the present invention shown in vivo with an adjustment tool having reduced column stiffness.

FIG. 49 is a schematic view of another embodiment of the implantable device system 1000 including an adjustment tool 1806 with reduced column stiffness. The adjustment tool 1806 has a handle 1096 a shaft 1080 with reduced column stiffness for greater flexibility and easier articulation of the adjustment tool 1806. The handle 1096 may be a grip-like handle, as shown, or a smaller pen-type handle. The easier articulation offered by the this embodiment may facilitate user positioning of the device in vivo and clearing adjacent biological structures, particularly when it is docketed to the adjustable member 1004 of the implant 1002. Flexibility may be varied along the length of the adjustment tool shaft 1080. Flexibility may be increased at the distal region 1082 of the adjustment tool shaft 1006, particularly in the region immediately proximal to the gear/fitting at the distal tip of the adjustment tool 1006. This gear/fitting is constrained orthogonally to the adjustable member 1004, and it is important that the adjustment tool 1006 be easy to insert/connect and remain clear of biological structures.

Figure 50:
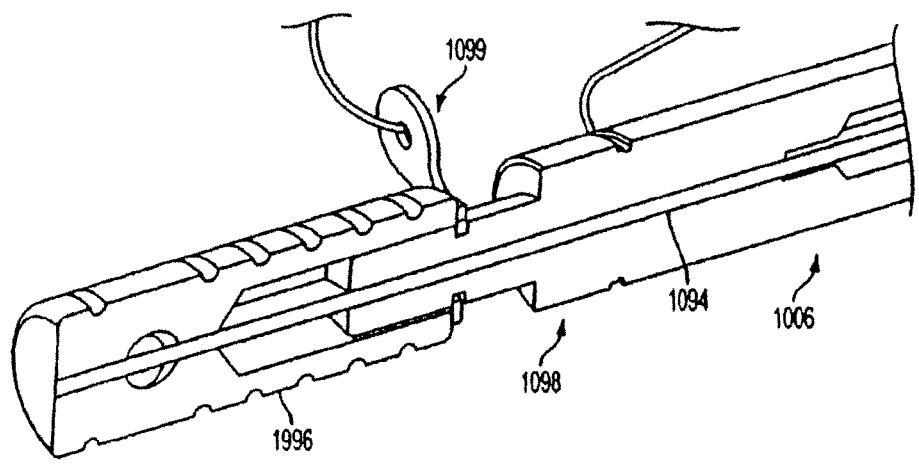
FIG. 50 is a cut-away view of an embodiment of the proximal portion of an adjustment tool.

FIG. 50 provides a view of an embodiment of the proximal end of the adjustment tool 1006. Referring to FIG. 50, adjustment tool 1006 includes a flexible cable 1094 or similar structure that is affixed to and rotates with a handle 1996. In other embodiments, the adjustment tool 1006 can have cables, a band, tubes, rods, and the like to impart rotational and/or axial motion from the proximal end to the distal tip of the tool 1006. The flexible cable 1094 may be enclosed by a flexible, low-friction cable jacket 1098 that allows the cable 1094 to rotate freely within the jacket 1098. In some embodiments, adjustment tool 1006 may also include a spring release mechanism to allow disengagement of the distal tip of the tool from the docking port 1021 (FIG. 33) with minimal force being applied to the sutures (or other mechanisms) securing the implant device to the tissue of an anatomic orifice or lumen. As shown in FIG. 50, in some embodiments, an e-clip 1099 or similar device may be used near the handle 1996 of the adjustment tool 1006 to secure the release mechanism in the docking station until adjustments are complete.

Figure 51:
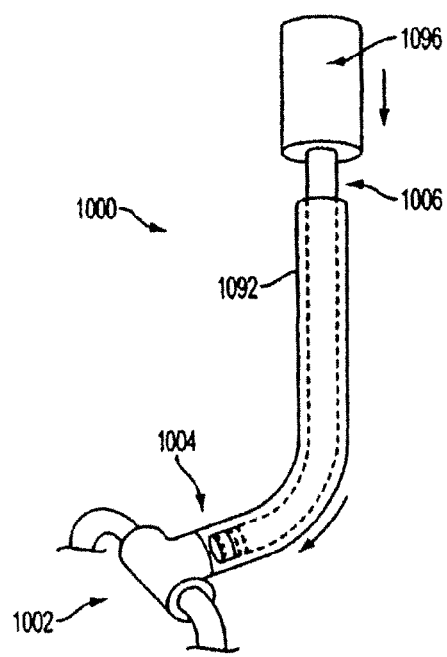
FIG. 51 is a schematic view of an embodiment of the implantable device of the present invention with an articulated shape.

In one embodiment illustrated in FIG. 51, the adjustment tool 1006 may be inserted inside a rigid sheath 1092 that reaches the implantable device 1002. Thus, FIG. 51 is a schematic view of an embodiment of the implantable device system 1000 of the present invention with an articulated shape. The rigidness of the sheath 1092 provides the necessary column strength to support the flexible adjustment tool 1006. An added benefit to this embodiment is that the sheath may be left in place, docked to the implantable device 1002. The flexible adjustment tool 1006 may be removed and then reinserted at some future time to engage with the adjustable member 1004 of implantable device 1002.

The adjustment tool 1006 can have a handle 1096 that can be adjustable. The handle 1096 can have a length of at least 8 inches, and in one embodiment at least 10 inches. Other embodiments may have a shorter or longer handle length. The handle 1096 may be thick to provide a hand-grip, or, in other embodiments, smaller to provide a pen-like grip. The handle can have a device to quantify a size change of the implantable device 1002. For example, a half-turn of the adjustment tool handle can be correlated to a distance of travel of the threaded rods 1018a, 1018b (FIG. 33) of an implant 1002, thus allowing for measured adjustment of the implant. The handle may include a click-counter or other known device to measure rotational movement. In one embodiment, the adjustment tool 1006 may be included in a percutaneous delivery catheter.

A sensor, such as the touchdown sensor described in relation to FIGS. 12-18 above, can be coupled to the implantable device 1002. A variety of different sensors can be utilized, including but not limited to, sensors that measure pressure, temperature and flow across the implantable device 1002. Pacing leads are coupled to the sensor and the implantable device 1002, and in this embodiment, the sensor is responsive to flow through the implantable device 1002.

In another embodiment the implantable device system may include a micro-electromechanical motor system in conjunction with or instead of a separate adjustment tool to commence rotational movement in an adjustable member. Power and control of the micro-electromechanical motor system can be provided by electromagnetic radiation or through a direct wire connection and previously described herein.

Finally, it will be understood that the preferred embodiment has been disclosed by way of example, and that other modifications may occur to those skilled in the art without departing from the scope and spirit of the appended claims.

Figure 52:
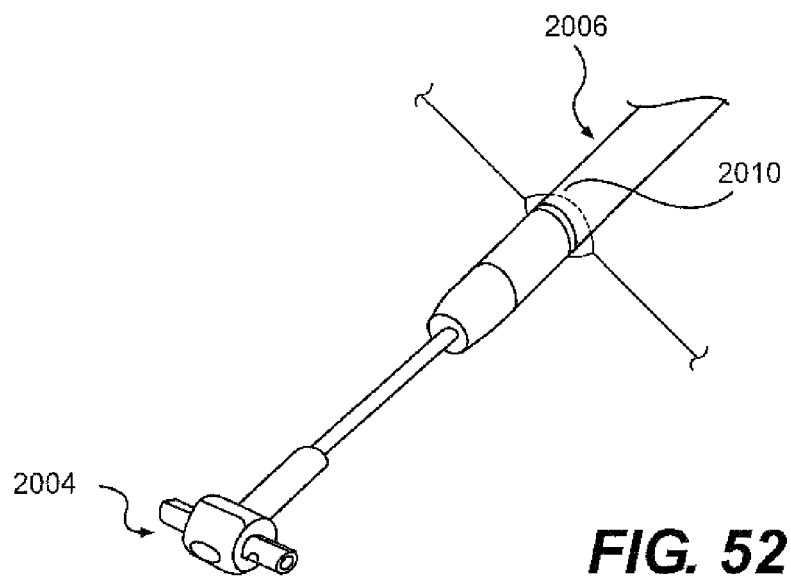
FIGS. 52-59 show one embodiment of an adjustment tool that can be reinserted into the body and reconnected to the adjustable member, so that additional adjustments to the implantable device can be made post-operatively.
Figure 53:
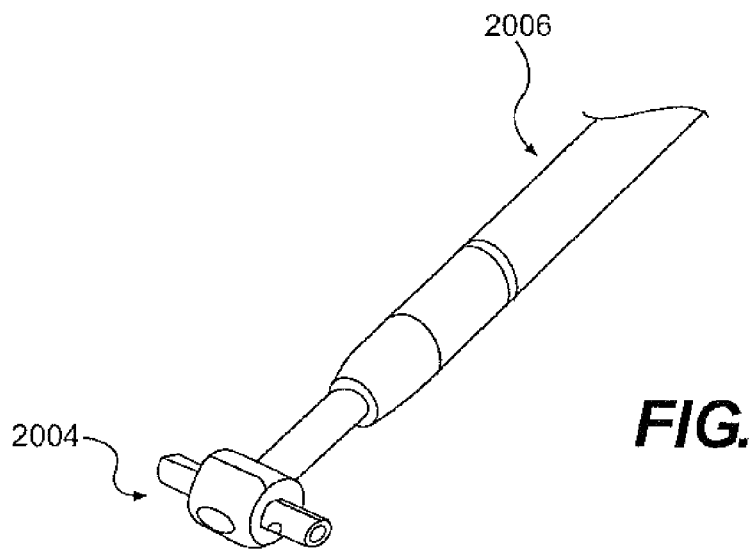

As discussed above, it is contemplated that the flexible adjustment tool 1006 may be removed and then reinserted at some future time to engage with the adjustable member 1004 of implantable device 1002. FIGS. 52-59 show one embodiment of an adjustment tool 2006 that can be reinserted into the body and reconnected to the adjustable member 2004, so that additional adjustments to the implantable device can be made post-operatively. More specifically, FIG. 52 shows the adjustment tool 2006 after it has been re-inserted into the left atrium, but before it has been reconnected to the adjustable member 2004. In this example, the adjustment tool 2006 is re-inserted into the left atrium via a purse string suture 2010. This procedure can be performed using a purse string suture tensioning device, such as the one described in International Patent Application No. PCT/US2008/080522, which is hereby incorporated by reference. FIG. 53 shows the adjustment tool 2006 after it has been reconnected to the adjustable member 2004.

Figure 54:
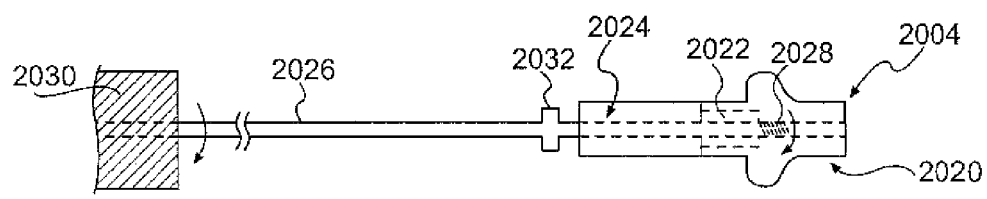
Figure 55:
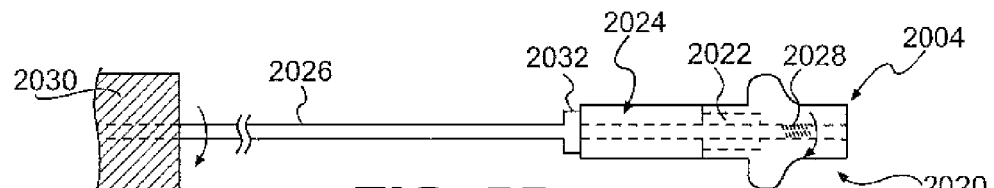

FIGS. 54-59 show the procedure for reconnecting the adjustment tool 2006 to the adjustable member 2004 of the implantable device. FIG. 54 shows an adjustable member 2004 with a gear 2020 that can be designed to control the size and/or shape of the implantable device, in accordance with any of the embodiments of the present invention previously described herein. The gear 2020 of the adjustable member 2004 is functionally connected to a gear hex fitting 2022, which in turn is functionally connected to a shaft hex fitting 2024. In a preferable embodiment, the shaft hex fitting 2024 is made of a rigid material that will allow it to most effectively transmit torque to the gear 2020. After the implantable device has been attached to an anatomic orifice or lumen, both the gear hex fitting 2022 and the shaft hex fitting 2024 remain connected to the adjustable member 2004 so that the adjustment tool 2006 can be reconnected to the adjustable member 2004 at a later time. In order to post operatively reconnect the adjustment tool 2006 to the adjustable member 2004, first, a guidewire 2026 is inserted into the body and connected to the gear 2020 of the adjustable member 2004 by rotating a threaded screw 2028 on the distal end of the guidewire 2026 using a knob component 2030 attached to the proximal end of the guidewire 2026, as shown in FIG. 54. The knob component 2030 and screw 2028 are rotated until a shoulder portion 2032 of the guidewire 2026 contacts the shaft hex fitting 2024, as shown in FIG. 55.

Figure 56:
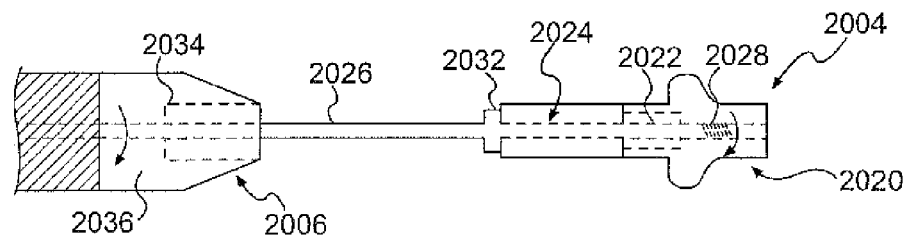
Figure 57:
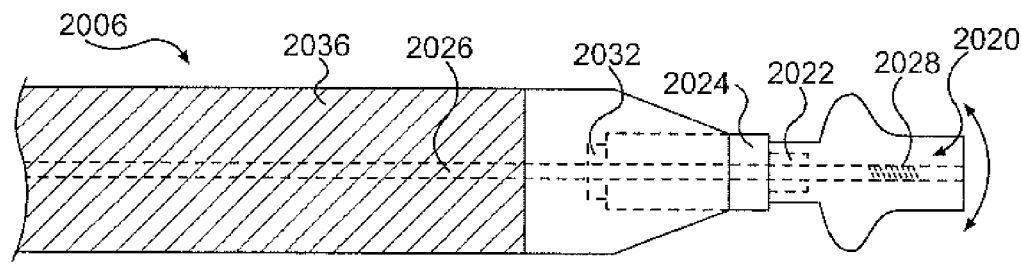
Figure 58:
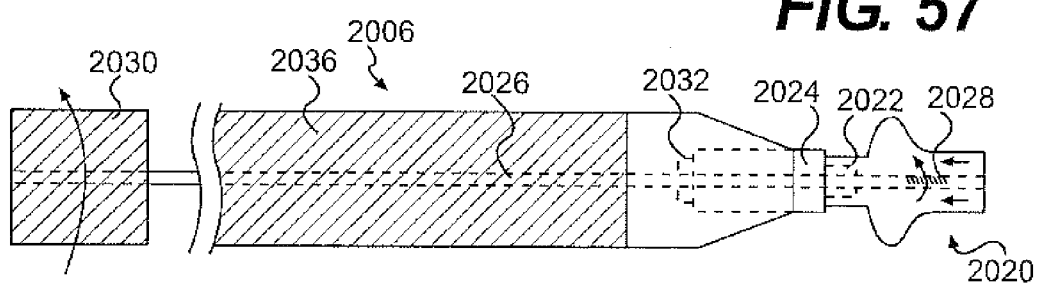
Figure 59:
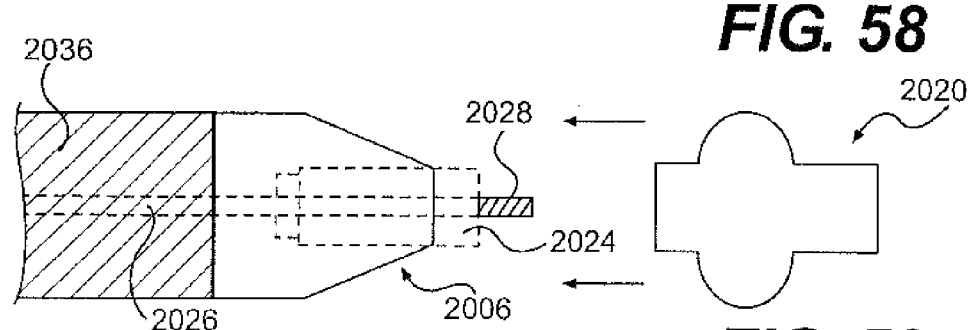

FIG. 56 shows the adjustment tool 2006 being reinserted along the guidewire 2026. The distal end of the adjustment tool 2006 includes a shaft hex tip 2034 with an internal hex that mates with shaft hex fitting 2024 connected to the adjustable member 2004. Once the adjustment tool 2006 has been mated with the shaft hex fitting 2024, the shaft 2036 of the adjustment tool 2006 can be rotated in order to impart rotation on the shaft hex fitting 2024. As shown in FIG. 57, this will cause the gear 2020 to rotate, which will cause the implantable device to change shape and/or size, as was explained above with respect to embodiments of the implantable device. After the desired adjustment has been completed, the adjustment tool 2006 can be detached from the adjustable member 2004 by rotating the knob component 2030 and unscrewing the guidewire 2026 from the gear 2020, as shown in FIG. 58. Finally, FIG. 59 shows that, after the guidewire 2026 has been unscrewed, the adjustment tool 2006, guidewire 2026, and shaft hex fitting 2024 can all be removed from the body.

Figure 60:
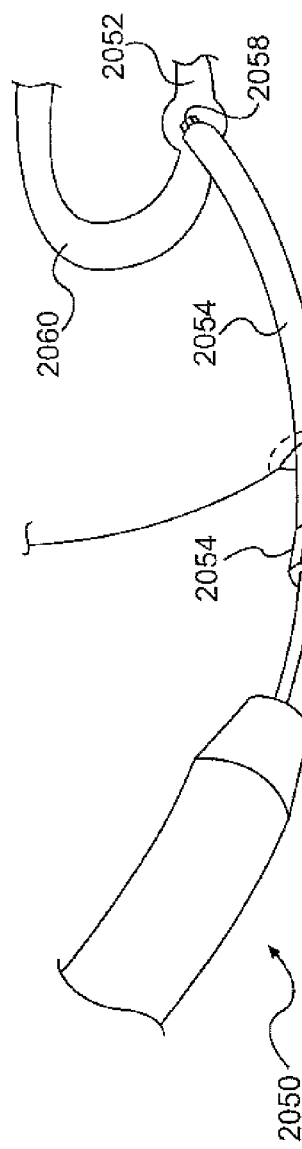
FIGS. 60-62 show a second embodiment of an adjustment tool that can be reinserted into the body and reconnected to the adjustable member so that additional adjustments to the implantable device can be made post-operatively.
Figure 61:
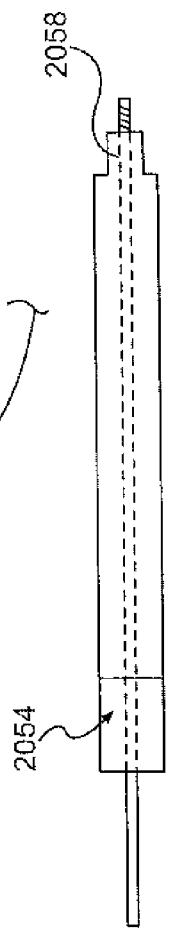
Figure 62:
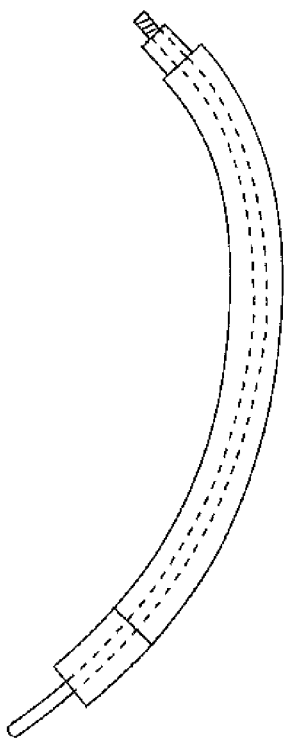

FIGS. 60-62 show a second embodiment of an adjustment tool 2050 that can be reinserted into the body and reconnected to the adjustable member 2052 so that additional adjustments to the implantable device can be made post-operatively. In this embodiment, the shaft hex fitting 2054 is constructed so that it is long enough to extend through the purse string suture 2056. Similar to the previous embodiment, the shaft hex fitting 2054 and gear hex fitting 2058 are left in the body when the adjustable implant 2060 is attached to the anatomic orifice or lumen. The advantage of this embodiment is that, as shown in FIG. 60, it allows the adjustment tool 2050 to connect to the shaft hex fitting 2054 without having to be re-inserted through the purse string suture 2056. This is beneficial because it reduces the stress placed on the purse string suture during reconnection of the adjustment tool. The process for re-inserting and reconnecting the adjustment tool 2050 to the adjustable member 2052 is similar to that discussed above with respect to FIGS. 54-59, with one difference being that the connection takes place outside the purse string suture 2056. Furthermore, because the shaft hex fitting 2054 is longer in this embodiment, it will need to be flexible (rather than rigid) to accommodate the anatomy of the heart, as shown in FIGS. 61-62.

As discussed above, in various embodiments contemplated by the present invention, an adjustable implant may be placed and affixed in position in a native recipient anatomic site by a percutaneous or other minimally invasive routes during beating or non-beating cardiac surgical procedures. FIGS. 63-72 show a reversible attachment apparatus that can be used to attach an adjustable implant to an anatomic orifice or lumen using a minimally invasive procedure. It will be understood that the preferred embodiments disclosed below are by way of example, and that other modifications may occur to those skilled in the art without departing from the scope and spirit of the appended claims.

Another aspect of the present invention enables implantation and adjustment of an implantable device using minimally invasive techniques. A further aspect enables an implantable device to be repositioned numerous times without invasive procedures. By way of non-limiting example, one aspect of the current invention relates to a mitral ring that can be positioned and then removed numerous times in order to ensure that it is in the proper location.

By way of non-limiting example, a surgeon could deliver an adjustable implantable device using a French catheter and approaching the annulus in at least two ways. One way of approaching would be through the jugular vein to the superior vena cava to the right atrium to the transseptal and to the left atrium. Another way to approach would be through the femoral vein, to the inferior vena cava, to the right atrium, to the transseptal then to the left atrium. Other minimally invasive techniques would also function without departing from the invention.

Once the implantable device is at the location where it is to be deployed, the present invention allows for positioning and repositioning of the device to ensure that it is in its proper location. For example, a surgeon could access the positioning of the device remotely using transesophageal echocardiography (TEE) or other diagnostic device or tools such that the position of the device can be ascertained. If the device is not in the correct position, then it can be detached and repositioned. This process can be repeated until the device is in an acceptable location. Once the device is in an acceptable position, its dimensions can be adjusted remotely. These adjustments can be tracked by TEE or other diagnostic imaging device.

By way of example, FIG. 63 shows a side view of a device that embodies the invention. The ring has at least an upper and a lower compartment. The upper compartment 2999 can contain mechanical components such as those described and illustrated in FIG. 76-86, 6-11 or 21-24. Similar components or no mechanical components can be in the upper compartment without departing from the present invention. The lower compartment 2998 can contain a reversible attachment apparatus that enables repeated repositioning of the ring.

By way of further example, FIG. 64 shows an embodiment of the invention. A movable retainer ring guide 3001 that can be moved in either direction and forms the floor of the upper compartment. A foam material 3002 is included through which all retainers pass. This foam can be made of a biocompatible, compressible or resilient material. The floor 3003 of the lower compartment 2988 is made of Dacron, or similar material, and makes contact with an annulus 2997. The retainers pass through the Dacron. The combination of the foam and the Dacron create a ring that can approximate the surface of the annulus 2997. In one embodiment displayed in FIG. 64, the Dacron is woven to a housing with a guide 3004 that is made of material such as titanium. This guide 3004 serves to position the barbed retainer 3005 into the annulus 2997 tissue that, in turn, does the same for the common retainers 3006. The guide 3004 serves to act as a stop or distance limiter between the Dacron cover and the movable retainer guide 3001 or roof of the lower compartment. Thus, when the ring attachments need to be removed so that the ring can be repositioned, the lower compartment 2998 returns to its original shape.

Figure 65:
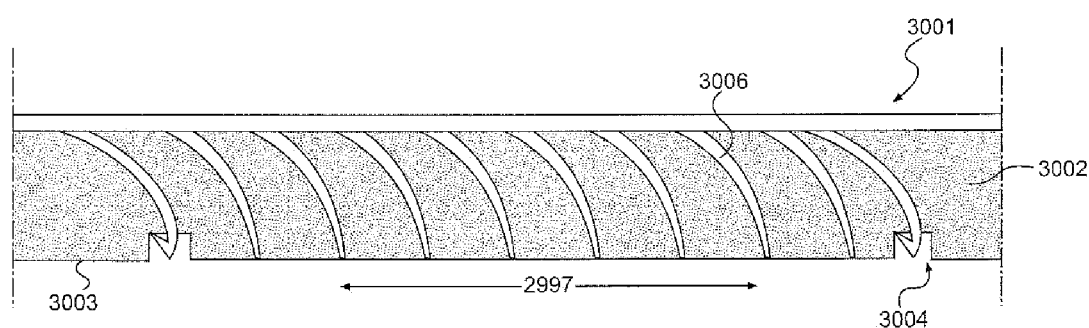
Figure 66:
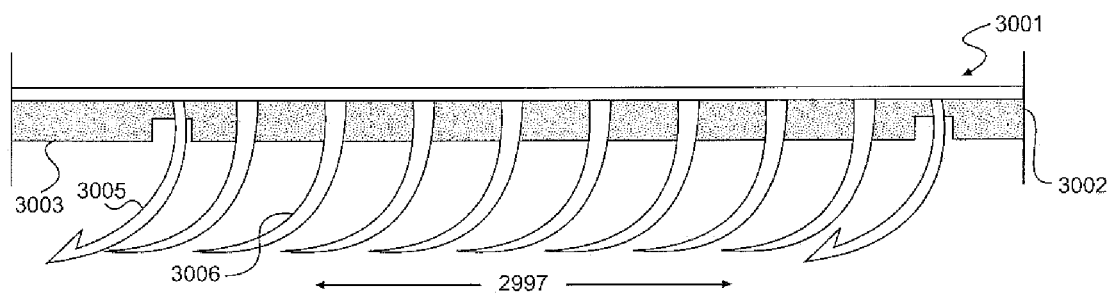

The barbed retainer 3005 can be made of titanium or similar material and is rigid where it enters the annulus 2997 tissue but flexible where it attaches to the movable retainer guide 3001. In FIG. 65-66, another lateral view of an embodiment of the invention is shown. In this view, the lower compartment 2998 of the implantable device is shown in contact with the annulus 2997 surface in an inactivated mode and then with both the barbed and common retainers deployed.

FIG. 66 shows both retainers being deployed in the annulus 2997 tissue. When the movable retainer guide 3001 is moved to the right, in this example, the barbed retainers 3005 leave their housing and deploy into the annulus 2997 in a circular direction in the manner of a fish hook. The barbed retainers 3005 are guided by the guide portion of the housing 3004. The common retainers 3006 deploy through the foam 3002 covered with Dacron. The foam 3002 is compressed resulting in an intimate contact with the annulus 2997 that comports to the shape of the annulus 2997.

Figure 67:
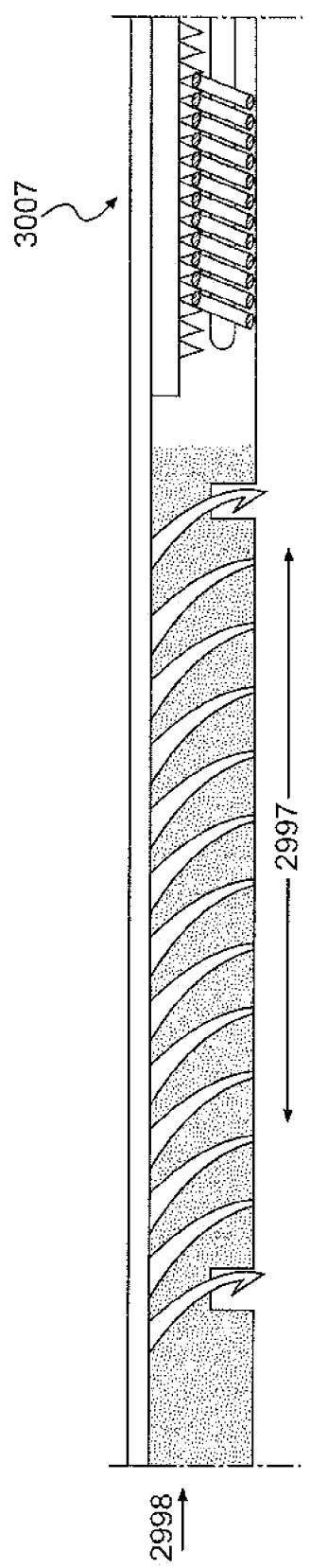
Figure 68:
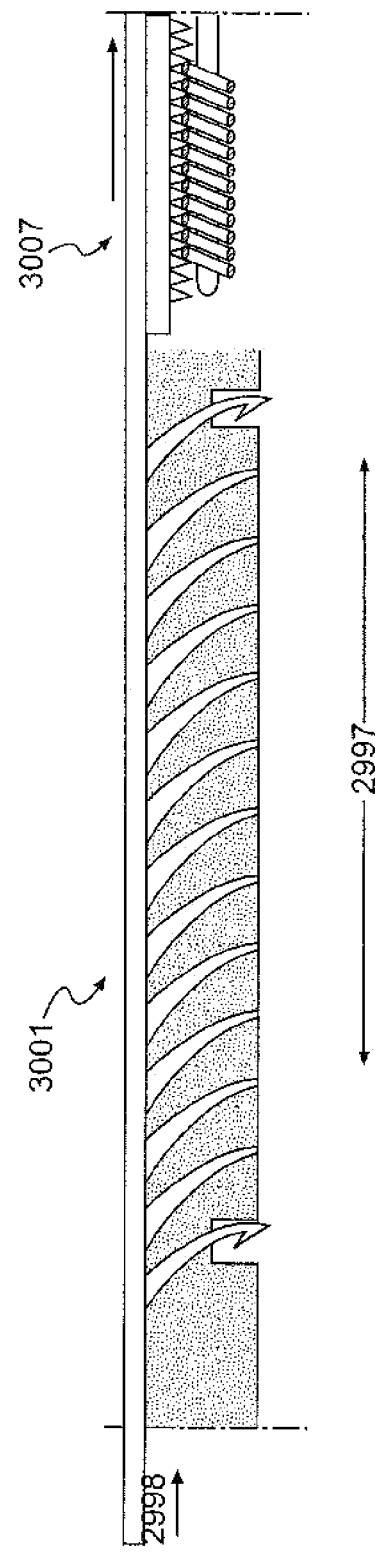

In another example of an embodiment of the invention, FIG. 67 shows an implantable device. In this Figure, the lower compartment 2998 is compressed such that the device is ready to be inserted into a #20 French canula (not shown). A drive mechanism 3007 moves the guide 3004 which, in turn, compresses the foam 3002 and flattens the barbed retainers 3005 and common retainers 3006. FIG. 68 shows an implantable device deployed out of the canula and resting passively on the annulus 2997. The drive mechanism 3007 can be used to move the movable retainer guide 3001 to enlarge toe foam 3002 to its maximum size. The drive mechanism 3007 may also be used to move the retainers 3005, 3006 to their upright position.

Figure 69:
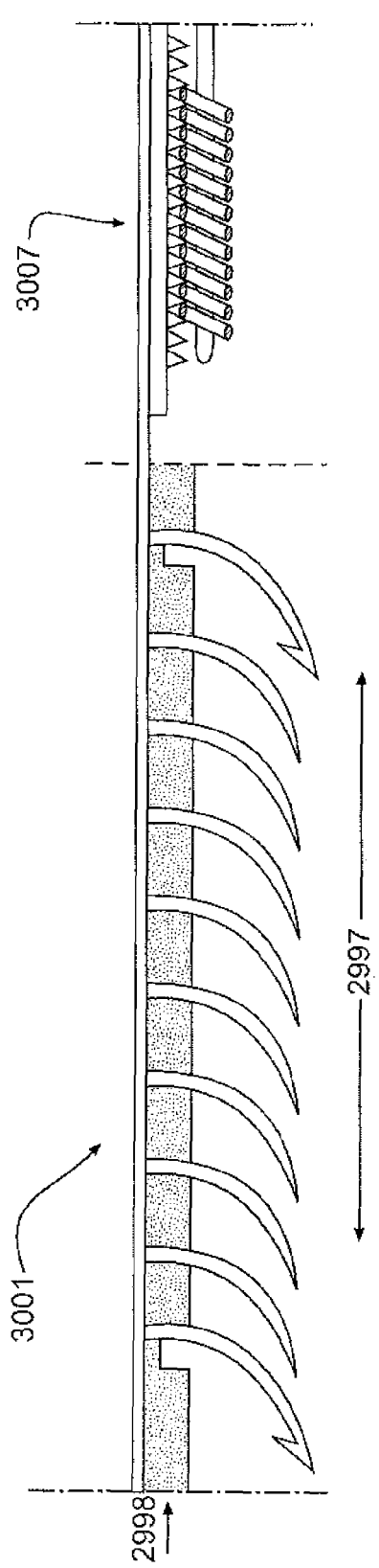

In the activated mode, an example of which is shown in FIG. 69, the drive mechanism 3007 moves the movable retainer guide 3001 in order to compress the foam 3002 and drive the barbed 3005 and common 3006 retainers into the annuls 2997 tissue.

Figure 70:
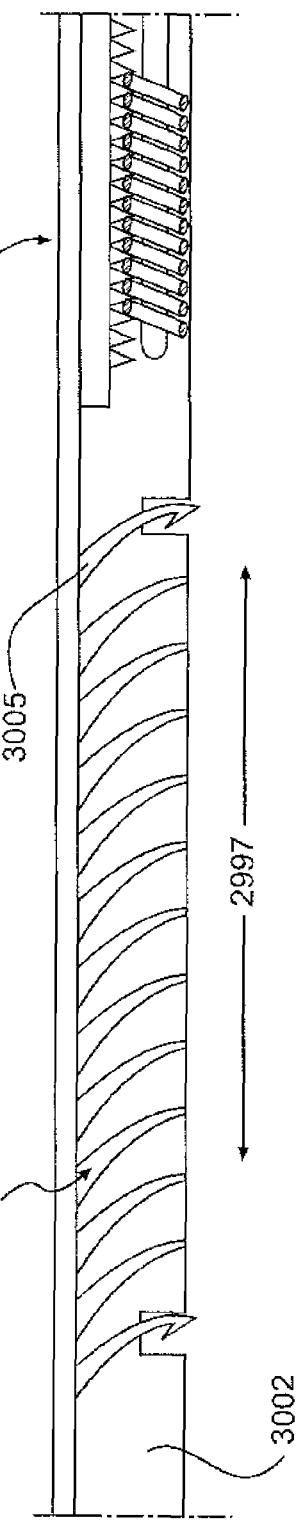
Figure 71:
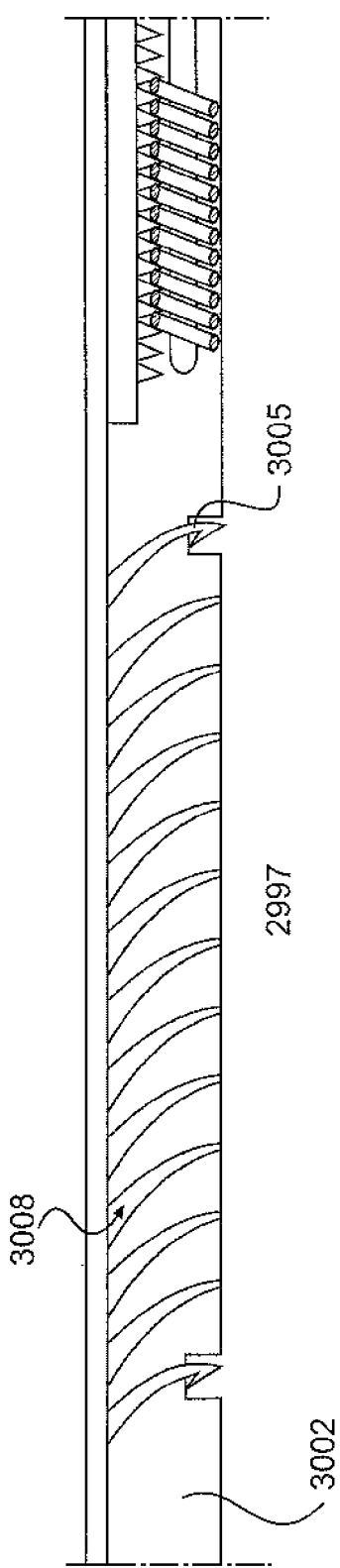
Figure 72:
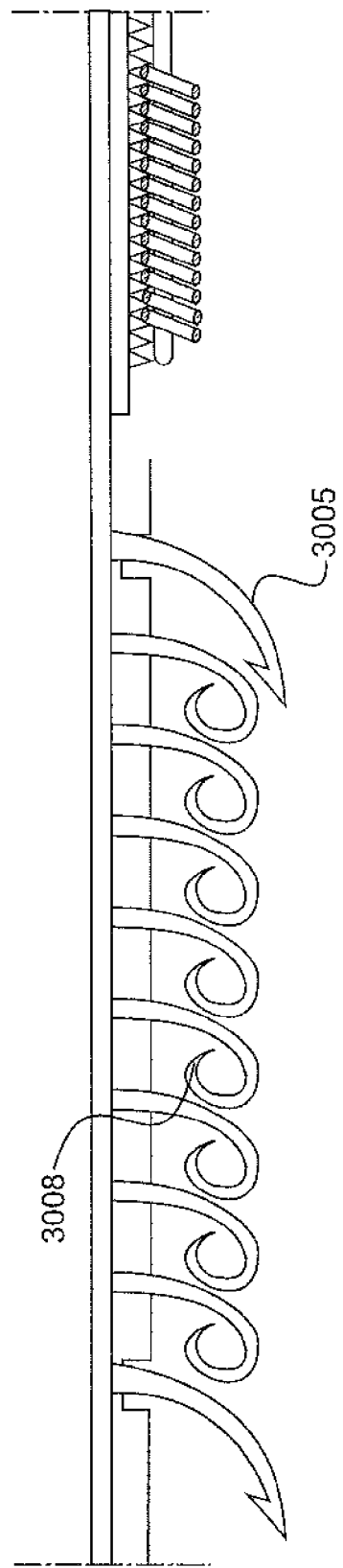

Another embodiment of the invention is displayed in FIG. 70-72. In this figure, the common retainers 3008 are made of a nickel titanium alloy and are pre-stressed. When deployed the common retainers 3008 will spiral in the tissue thereby increasing retention. The common retainers 3008 made of nickel titanium alloy can be retracted into the foam 3002 where they resume their original shape. The retention and common barbs of the invention, as illustrated above by the non-limiting examples discussed, allow for repeatable attachment and detachment of an implantable device while removing or minimizing tissue damage.

As discussed above, it is contemplated that embodiments of the present invention can be used to adjust the shape and/or size of other heart valves, such as the tricuspid valve. The tricuspid valve has three leaflets: the anterior leaflet, the septal leaflet, and the posterior leaflet. Regurgitation in the tricuspid valve is often due to a loss of coaptation between the anterior and posterior leaflets. The atrioventricular node (AV node) is located near the septal leaflet of the tricuspid valve. This is significant because causing trauma near the AV node, such as by suturing, can result in heart block. FIGS. 73-78 show one embodiment of an implantable device that can be used to adjust the shape and/or size of the tricuspid valve. In this embodiment, the implantable device 4002 has an open ring design, and can be positioned so that no suturing is needed near the AV node.

Figure 73:
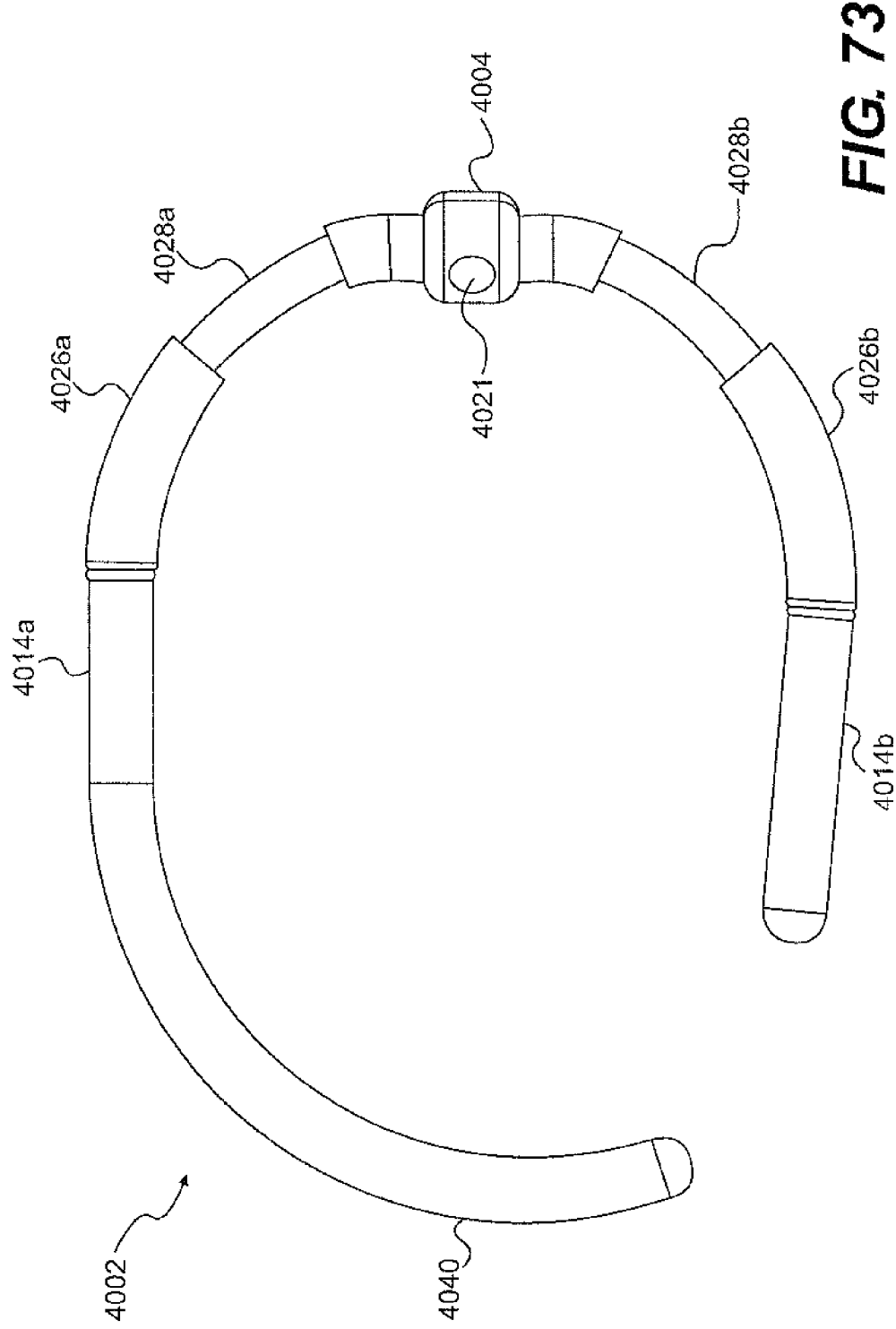
FIGS. 73-84 show embodiments of an implantable device that can be used to adjust the shape and/or size of a tricuspid valve.

FIG. 73 shows an implantable device 4002 with an adjustable member 4004 that includes a docking port 4021 to receive the distal end of an adjustment tool, such as the adjustment tool shown in FIG. 31 and described above. The adjustable member 4004 can have a pinion gear that engages with a crown gear, such as the adjustable member shown in FIGS. 36 and 37 and described above. The implantable device 4002 includes a set of inner tubing 4028*a*, 4028*b* and a set of outer tubing 4026a, 4026b, which can move relative to one another. The ends of the inner tubing 4028a, 4028b that do not engage the outer tubing 4026a, 4026b are secured to the adjustable member 4004 so that the inner tubing 4028a, 4028b does not move relative to the adjustable member 4004. The implantable device 4002 also includes a set of hollow tube portions 4014a, 4014b. The hollow tube portions 4014a, 4014b may be separate pieces of tubing that are permanently attached to the outer tubing 4026a, 4026b when the implantable device 4002 is assembled, or the hollow tube portions 4014a, 4014b may be formed from the same piece of tubing as the outer tubing 4026a, 4026b. The hollow tube portions 4014a, 4014b may be threaded on the inside to receive threaded rods 4018a, 4018b (shown in FIG. 77), or a threaded insert may be affixed to the inner diameter of the hollow tube portions 4014a, 4014b. The implantable device 4002 also includes a passive tube portion 4040, which is a portion of the implantable device 4002 that does not include any of the mechanisms used to adjust the size and/or shape of the implantable device 4002. This is shown in more detail in FIG. 77. It is contemplated that the passive tube portion 4040 can be either flexible or rigid.

Figure 74:
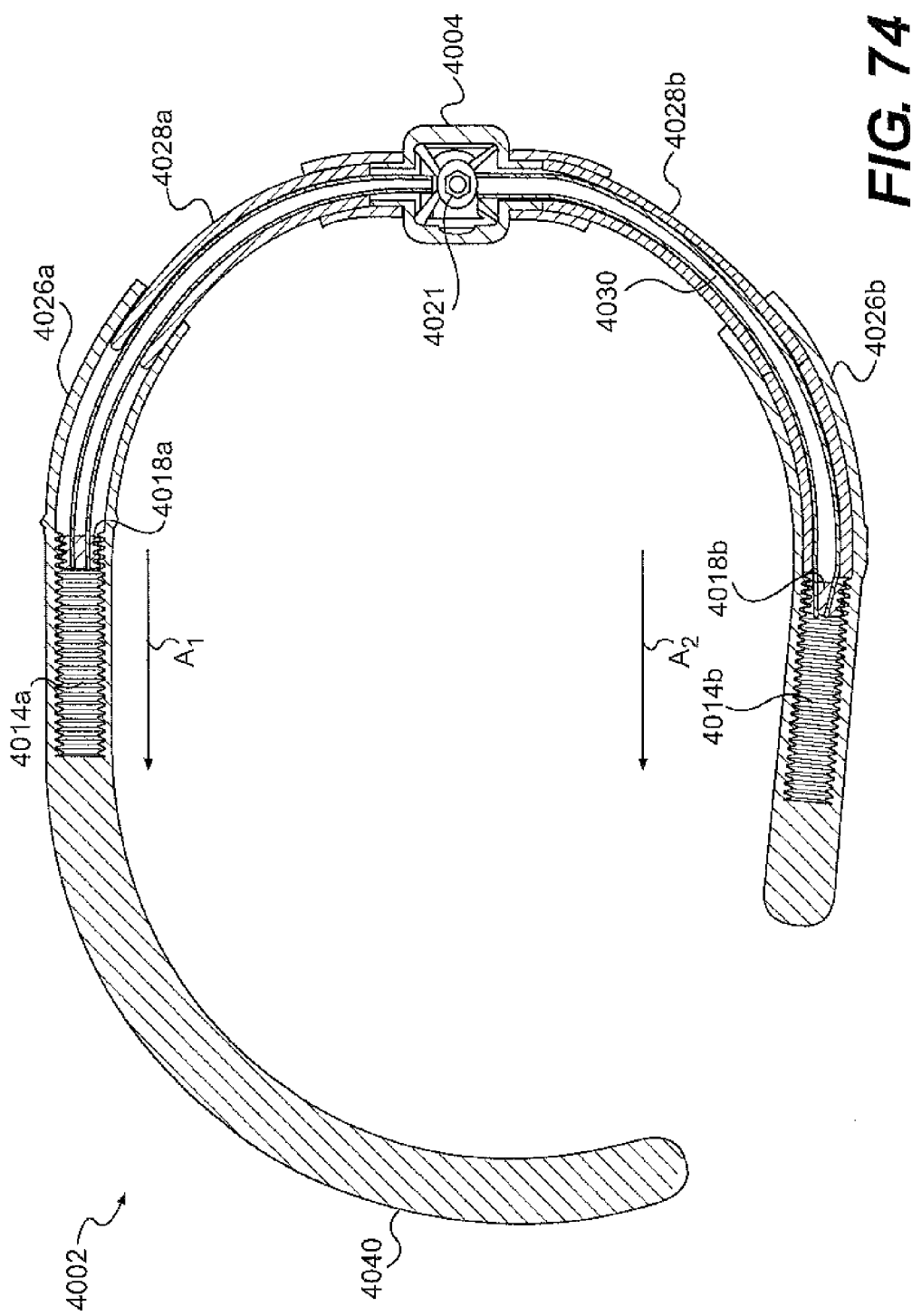
Figure 76:
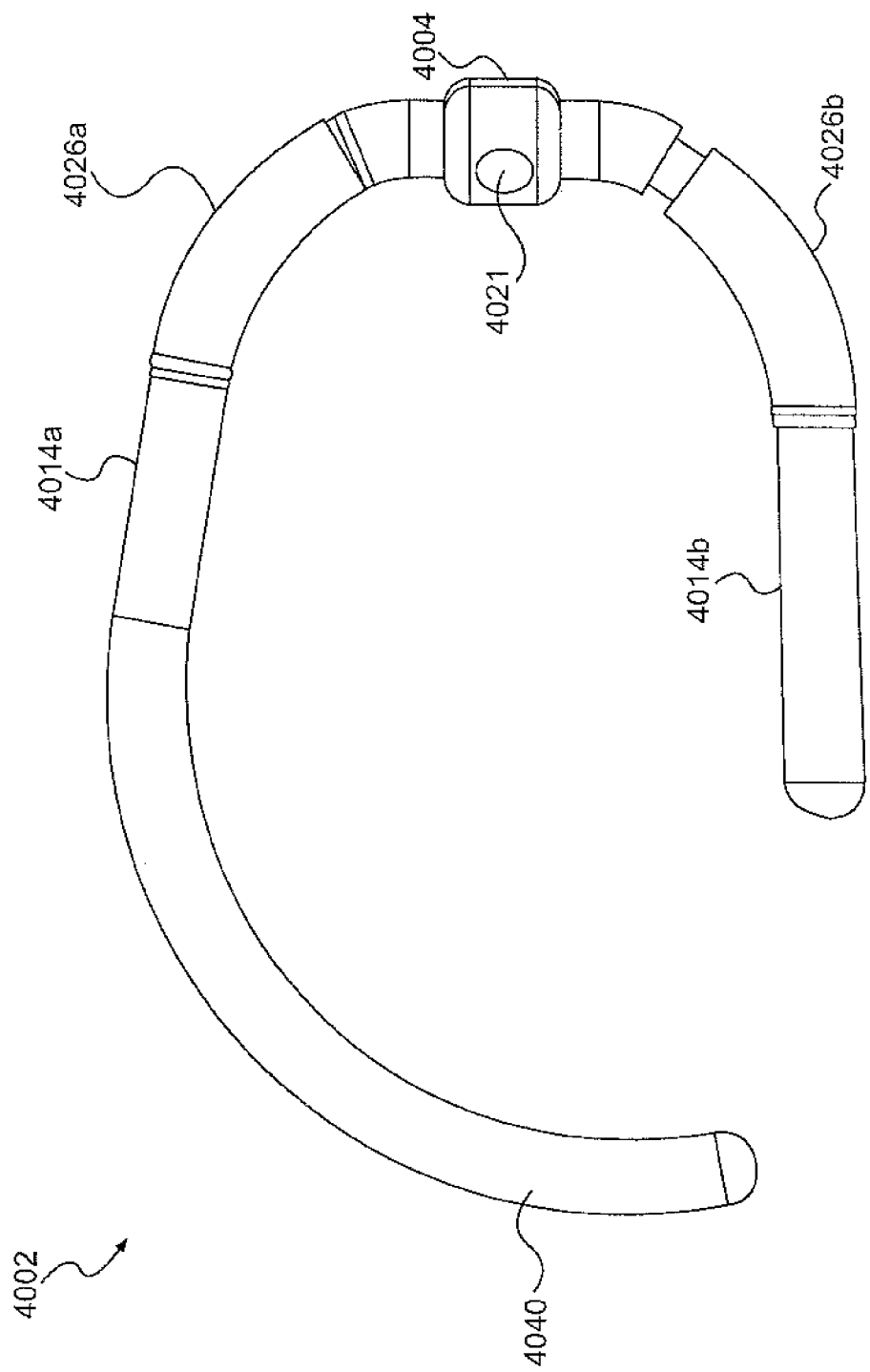

FIG. 74 shows a cross-sectional view of the implantable device 4002 of FIG. 76. As discussed above, the inner tubing 4028a, 4028b is affixed to the adjustable member 4004 and extends into the outer tubing 4026a, 4026b. The outer tubing 4026a, 4026b is affixed to the hollow tube portions 4014a, 4014b. An inner cable 4030 is functionally connected to the adjustable member 4004, as shown in FIGS. 36 and 37 above, and passes thorough the inner tubing 4028a, 4028b and the outer tubing 4026a, 4026b. The inner cable 4030 is also connected to a set of threaded rods 4018a, 4018b, which are engaged with the threads on the inside of the hollow tube portions 4014a, 4014b. The threaded rods 4018a, 4018b may be a rigid material such as titanium, stainless steel, or a polymer. The hollow tube portions 4014a, 4014b enclose the threaded rods 4018a, 4018b, such that rotation of the threaded rods 4018a, 4018b causes them to move axially within the hollow tube portions 4014a, 4014b. In one embodiment, the threaded rod 4018a may have right-handed threads, and the threaded rod 4018b may have left-handed threads. In other embodiments, the threaded rods 4018a, 4018b may both have right-handed threads or left-handed threads. The inner cable 4030 may be a cable or tube of any material with sufficient flexibility to conform to the shape of the implantable device 4002 while translating torque. For example, suitable materials for the inner cable 4030 may include titanium or stainless steel. As shown more clearly in FIGS. 36 and 37, rotating the crown gear of the adjustable member 4004 imparts rotation to the inner cable 4030 in the same direction.

Figure 75:
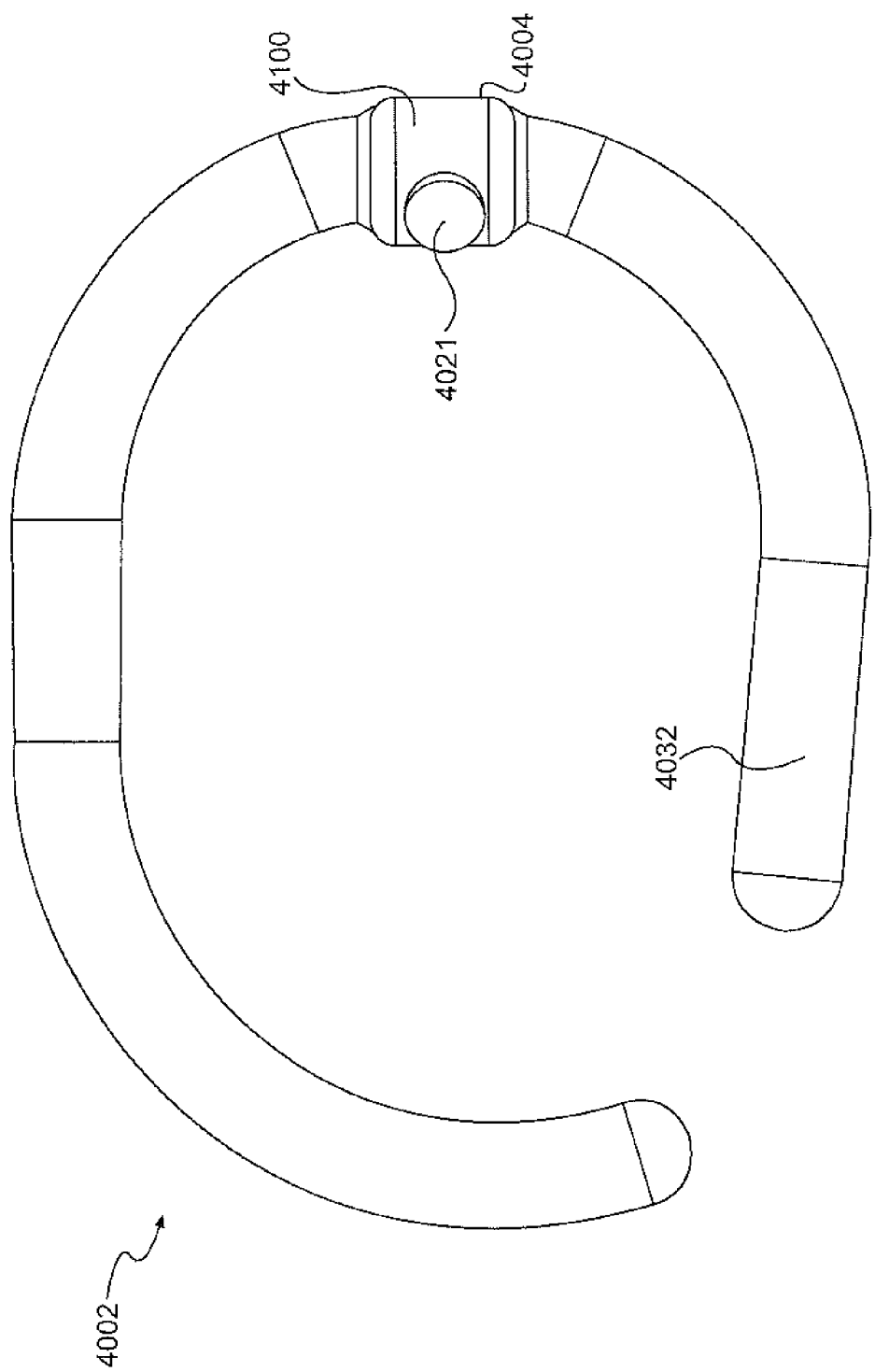

FIG. 75 shows an embodiment of the present invention where the implantable device 4002 is covered by an outer flexible tube 4032 (such as a silicone tube) and a seal jacket 4100, so that no moving parts are exposed. The flexible outer tube 4032 can provide sufficient rigidity so that the implantable device 4002 maintains a generally planar dimension, while allowing it to adjust shape in a preferred dimension, such as the anterior-posterior dimension. In one embodiment, the outer flexible tube 4032 is provided without a seam in the axial direction in order to allow for better tissue in-growth after it has been implanted. The flexible outer tube 4032 may be further covered by an outer fabric sheath. The seal jacket 4100 may cover the adjustable member 4004 and also include a cover for the docking port 4021 in the form of a slit septum, flaps, elastic material or the like. In one embodiment, the seal jacket 4100 may be secured to the outer flexible tube 4032. The seal jacket 4100 and the outer flexible tube 4032 may be secured by an adhesive bond, a wrap, sutures, or the like. The seal jacket 4100 provides access for an adjustment tool to couple to the docking port 4021, while reducing the possibility of thrombus formation. In some embodiments, the seal jacket 4100 may be made of silicone and covered by a polyester sewing layer or fabric sheath.

FIGS. 73-75 show the implantable device 4002 in an open position where it has its largest circumference. In order to reduce the circumference of the implantable device 4002, the handle of the adjustment tool (not shown) is rotated in the docking port 4021, such that it causes rotation of the pinion gear (not shown) of the adjustable member 4004. As described above, rotation of the pinion gear (not shown) in turn rotates the crown gear (not shown). The rotation of crown gear (not shown) then causes rotation of the inner cable 4030, which imparts rotational movement to each of the threaded rods 4018a, 4018b. The rotation applied to the threaded rods 4018a, 4018b causes them to advance into their respective hollow tube portions 4014a, 4014b in the directions $A_1$, $A_2$ shown in FIG. 77. As the threaded rods 4018a, 4018b advance into the hollow tube portions 4014a, 4014b, the inner cable 4030 also advances into the hollow tube portions 4014a, 4014b. The advancement of the inner cable 4030 into the hollow tube portions 4014a, 4014b causes the inner tubing 4028a, 4028b to slide into the outer tubing 4026a, 4026b, which reduces the overall circumference of the implantable device 4002.

Figure 77:
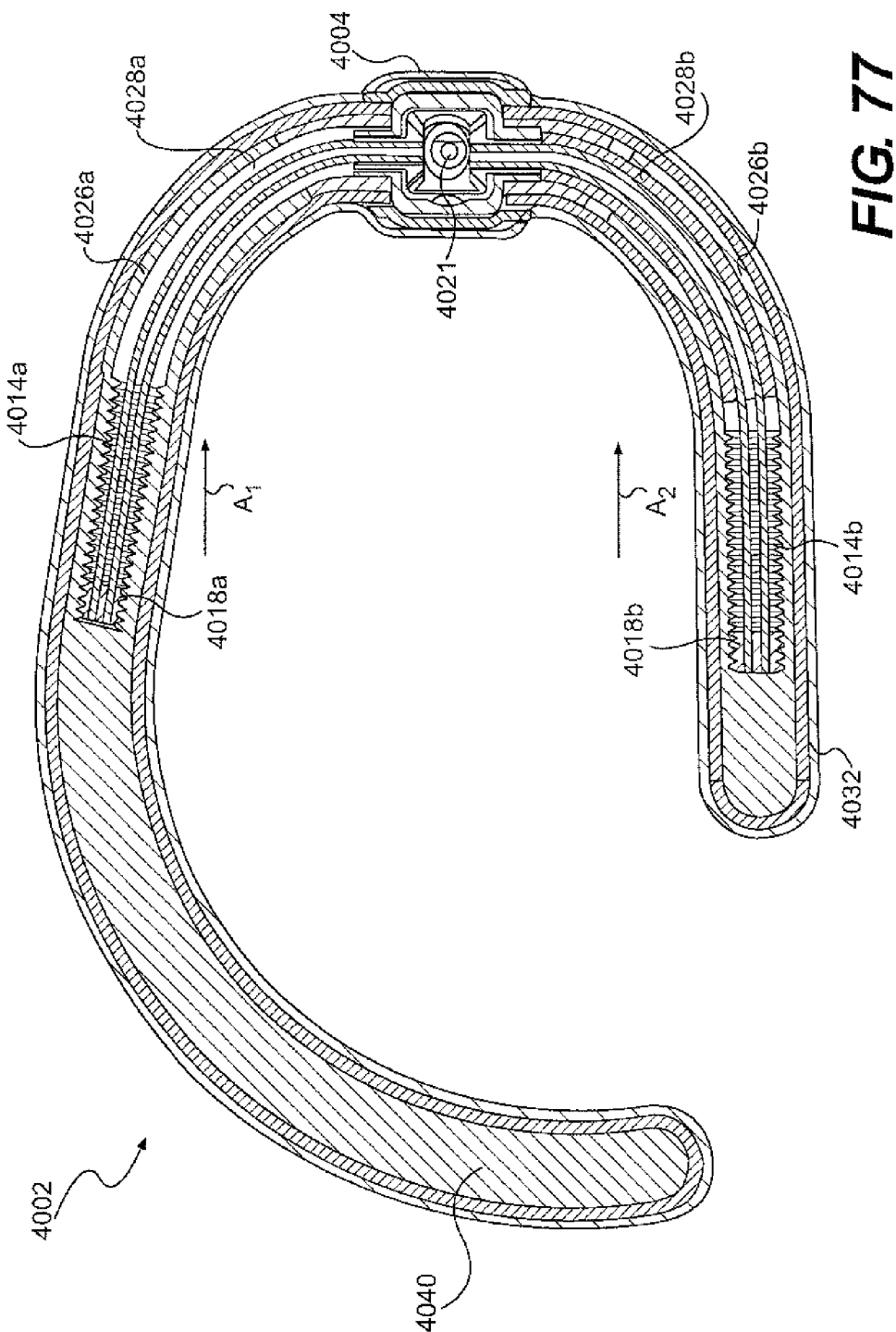
Figure 78:
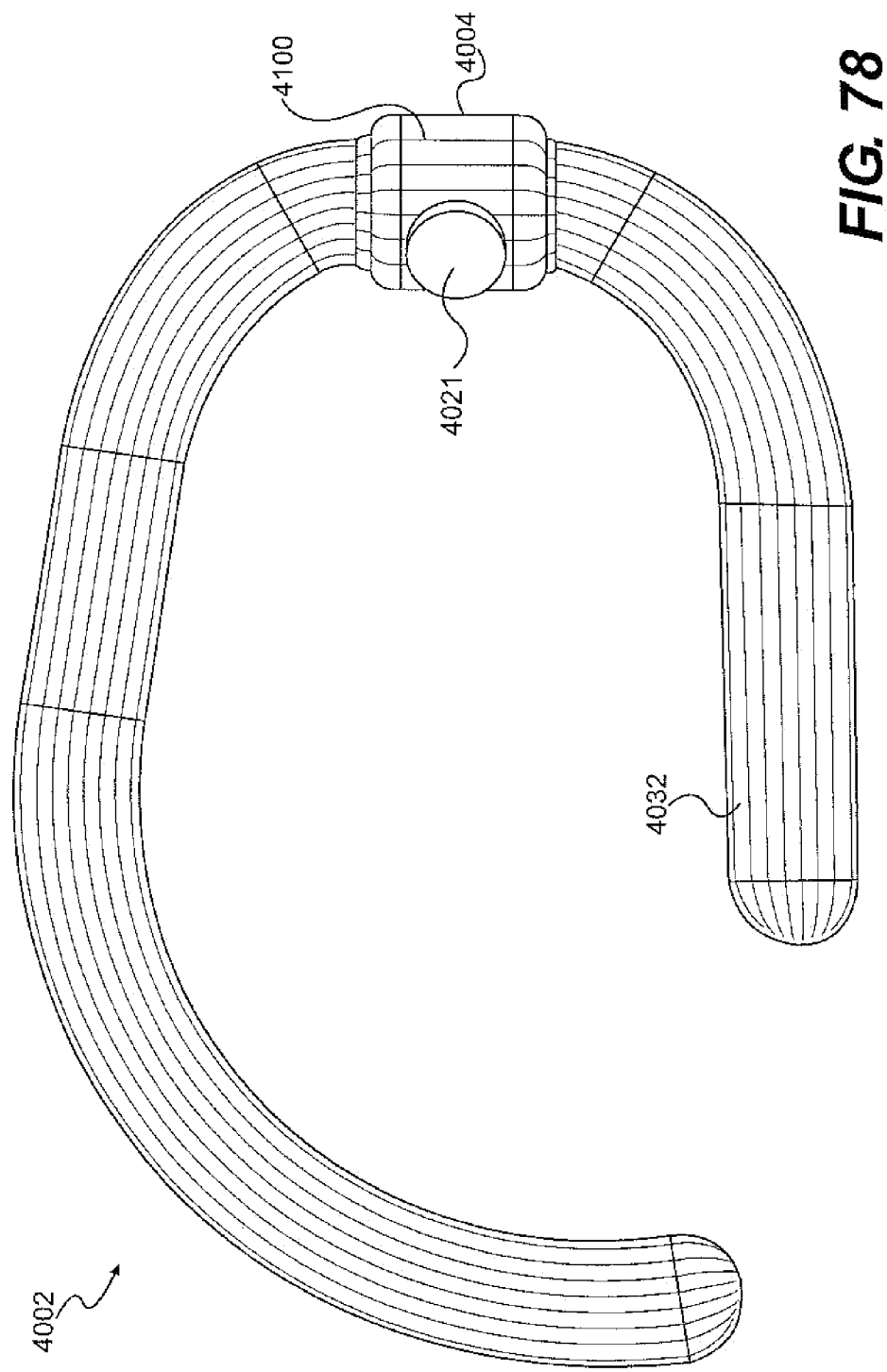

FIGS. 76-78 show the implantable device 4002 in a closed position where it has its smallest circumference. More specifically, as shown in FIG. 77, the threaded rods 4018a, 4018b are advanced completely into the hollow tube portions 4014a, 4014b, and the inner tubing 4028a, 4028b is completely inside the outer tubing 4026a, 4026b. In order to enlarge the circumference of the implantable device 4002, the handle of the adjustment tool (not shown) is rotated in a direction opposite to the direction used to reduce the circumference, so that it causes an opposite rotation of the pinion gear (not shown) of the adjustable member 4004. As described above, rotation of the pinion gear (not shown) in turn rotates the crown gear (not shown). The rotation of crown gear (not shown) then causes rotation of the inner cable 4030, which imparts rotational movement to each of the threaded rods 4018a, 4018b. The rotation applied to the threaded rods 4018a, 4018b causes them to withdraw from their respective hollow tube portions 4014a, 4014b in the directions $A_1$, $A_2$ shown in FIG. 77. As the threaded rods 4018a, 4018b withdraw from the hollow tube portions 4014a, 4014b, the inner cable 4030 also withdraws from the hollow tube portions 4014a, 4014b. The withdrawal of the inner cable 4030 from the hollow tube portions 4014a, 4014b causes the inner tubing 4028a, 4028b to telescope out of the outer tubing 4026a, 4026b, which increases the overall circumference of the implantable device 4002.

Figure 79:
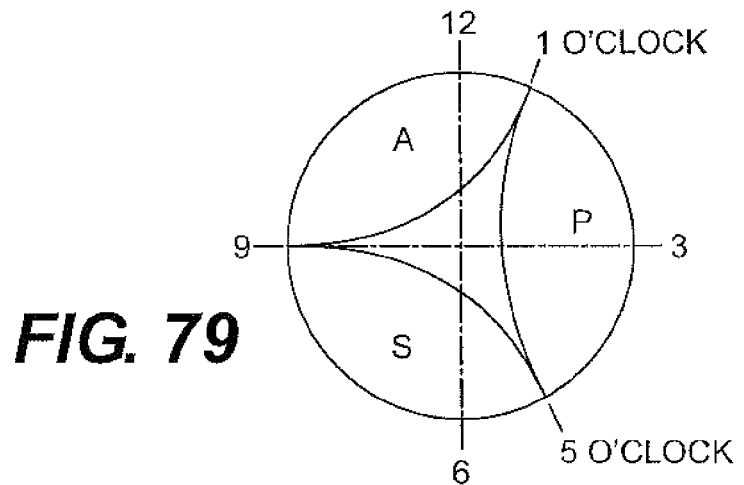
Figure 80:
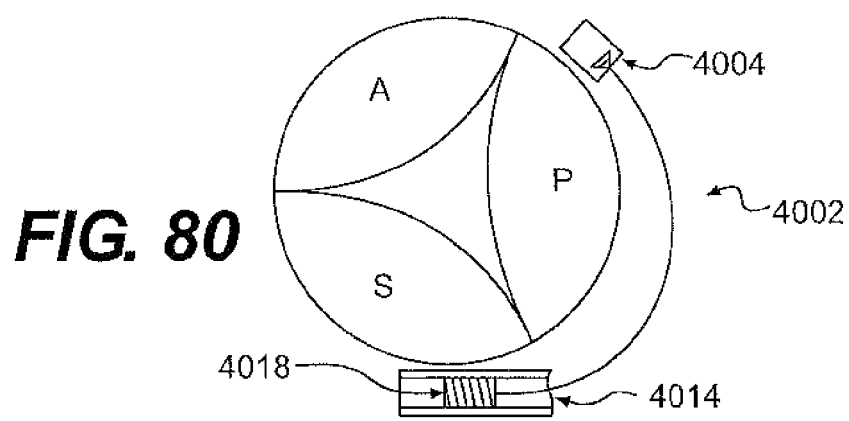
Figure 81:
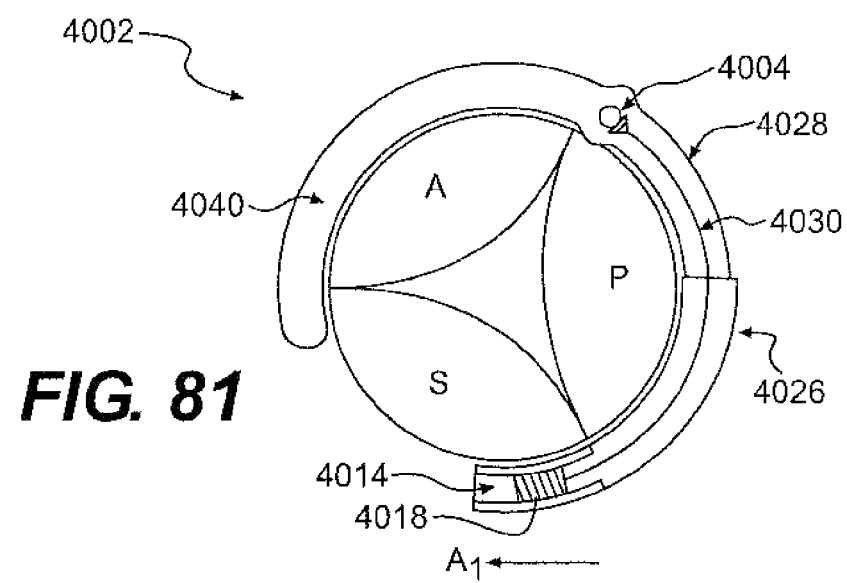
Figure 82A:
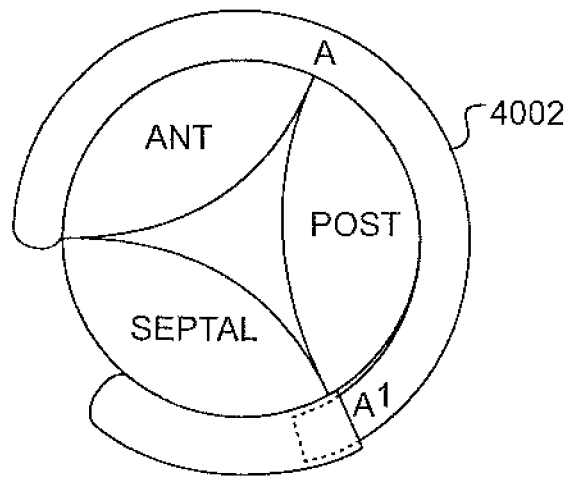
Figure 82B:
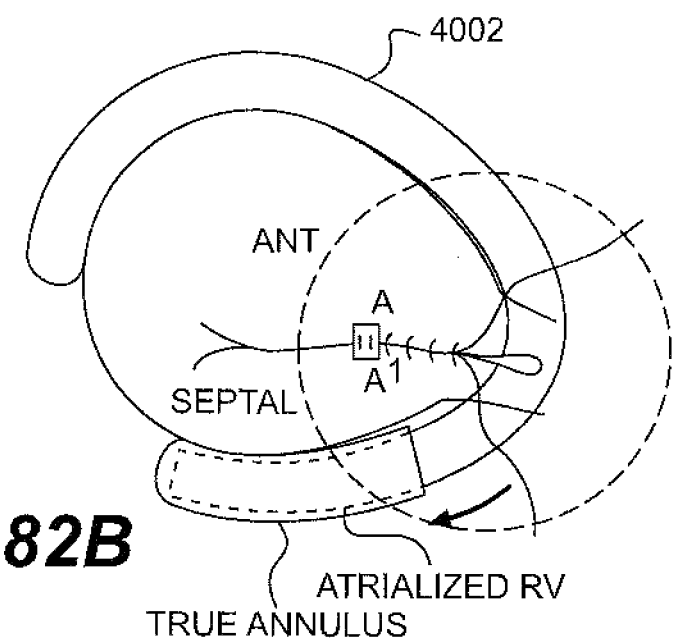

FIGS. 79-81 show another embodiment of an implantable device 4002 for adjusting the shape and/or size of a tricuspid valve. In this embodiment, the implantable device 4002 has an adjustable member 4004, a passive tube portion 4040, and a single threaded rod 4018 that is engaged with a single hollow tube portion 4014. One end of an inner cable 4030 is connected to the adjustable member 4004 and the other end is connected to the threaded rod 4018. The implantable device 4002 also includes an inner tube 4028 that can move relative to an outer tube 4026. The implantable device 4002 shown in FIGS. 79-81 can be adjusted in a similar fashion to the device shown in FIGS. 73-78 above. More specifically, in order to reduce the circumference of the implantable device 4002, the handle of the adjustment tool (not shown) is rotated in the docking port (not shown), such that it causes rotation of the inner cable 4030 (as described above), which imparts rotational movement to the threaded rod 4018. The rotation applied to the threaded rod 4018 causes it to advance into the hollow tube portion 4014 in the direction $A_1$ shown in FIG. 81. As the threaded rod 4018 advances into the hollow tube portion 4014, the inner cable 4030 also advances into the hollow tube portion 4014. The advancement of the inner cable 4030 into the hollow tube portion 4014 causes the inner tubing 4028 to slide into the outer tubing 4026, which reduces the overall circumference of the implantable device 4002. In order to enlarge the circumference of the implantable device 4002, the handle of the adjustment tool (not shown) is rotated in a direction opposite to the direction used to reduce the circumference, so that it causes an opposite rotation of the inner cable 4030. One advantage of this design is that the adjustable member 4004 can be made with smaller gears.

Figure 83:
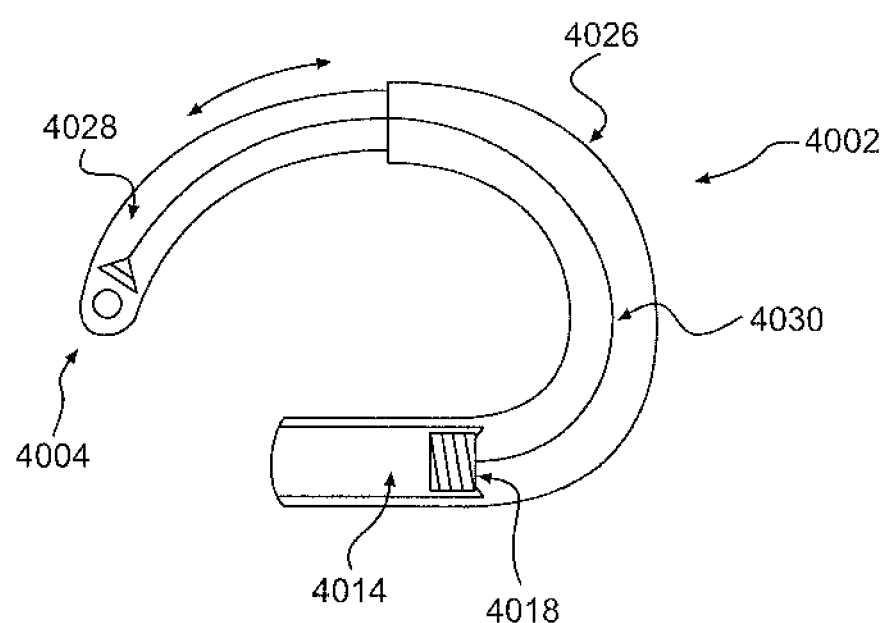

FIG. 83 shows another embodiment of an implantable device 4002 for adjusting the shape and/or size of a tricuspid valve. This embodiment is similar to that shown in FIGS. 79-81, because it has a single threaded rod 4018 engaged with a single hollow tube portion 4014. One difference is that an adjustable member 4004 is located at one end of the implantable device 4002, and a hollow tube portion 4014 is located at the other end. As a result, the implantable device 4002 in FIG. 83 does not include a passive tube portion. To adjust the size of the implantable device 4002, an adjustment tool (not shown) is rotated which causes an inner cable 4030 to rotate. The rotation of the inner cable 4030 causes the threaded rod 4018 to move in or out of the hollow tube portion 4014, which in turn causes an inner tube 4028 to move in or out of an outer tube 4026, thus decreasing or increasing the circumference of the implantable device 4002. One advantage of this design is that the entire device can be made with a uniform flexibility or stiffness.

Figure 84A:
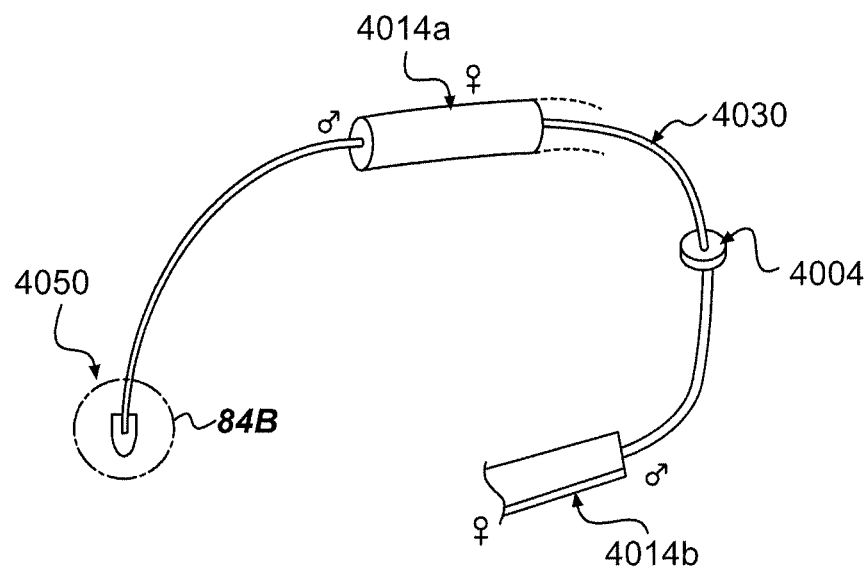
Figure 84B:
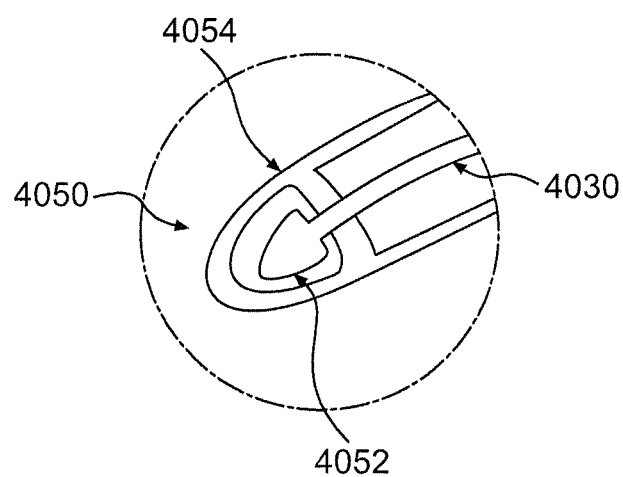

FIGS. 84A and 84B show another embodiment of an implantable device 4002 for adjusting the shape and/or size of a tricuspid valve. This embodiment is similar to that described above with respect to FIGS. 73-78, in that it has a set of hollow tube portions 4014*a*, 4014*b*. Although not shown, the implantable device 4002 also includes a set of threaded rods that are engaged with the hollow tube portions 4014*a*, 4014*b*, and a set of inner tubing that can move relative to a set of outer tubing. In the embodiment shown in FIGS. 84A and 84B, the hollow tube portion 4014*a* can be curved, and the hollow tube portion 4014*b* can be straight. The hollow tube portion 4014*a* has fewer threads on the inside for engaging with the threaded rod than the hollow tube portion 4014*b*. This design enables the implantable device 4002 to have a more curved profile. By varying the thread pitch on the hollow tube portions 4014*a*, 4014*b* and the threaded rods they are engaged with, it also allows the implantable device 4002 to make more fine adjustments on certain portions of the tricuspid valve and more coarse adjustments on other portions of the tricuspid valve.

It is further contemplated that embodiments of the implantable device 4002 described above can have both planar and non-planar designs. For example, the implantable device 4002 can have a spiral shape. It is also contemplated that, in some embodiments, the implantable device 4002 is a full, complete ring.

It is also contemplated that the adjustable member 4004 can be positioned in varying locations on the implantable device 4002 described in the embodiments above.

It is also contemplated that the implantable device 4002 can be used to make adjustments to the tricuspid valve after a patient has been taken "off pump" and normal flow of blood through the heart has resumed. It is also understood that the adjustment tool for making post-operative adjustments described above can be used to make post-operative adjustments to the implantable device 4002.

Finally, it will be understood that the preferred embodiment has been disclosed by way of example, and that other modifications may occur to those skilled in the art without departing from the scope and spirit of the appended claims.

The invention claimed is:

1. An implantable device system for controlling at least one of a shape and size of an anatomical structure or lumen, comprising:
    an implantable device adapted for attachment to an anatomical structure or lumen, said implantable device comprising an adjustable member configured to adjust at least one of a shape and size of the implantable device;
    an adjustment tool configured to be coupled to the adjustable member such that the adjustment tool can be used to activate and control adjustment of the implantable device;
    an attachment mechanism coupled to the implantable device and configured to attach the implantable device to the anatomical structure or lumen, and wherein the attachment mechanism permits repeated repositioning of the implantable device with respect to the anatomical structure or lumen, the attachment mechanism comprising:
    a resilient layer having first and second opposing surfaces; a moveable retainer ring guide supported on the first surface of the resilient layer adjacent the implantable device; a plurality of retainers attached to the retainer ring guide and extending into the resilient layer, whereby compression of the resilient layer by movement of the retainer ring guide causes a portion of the retainers to extend outwardly beyond the second surface of the resilient layer; and
    a rigid retainer guide positioned adjacent the second surface of the resilient layer for receiving an end of one of the retainers, the retainer guide configured as a stop member for limiting a distance between the second surface of the resilient layer and the retainer ring guide upon compression of the resilient layer by the retainer ring guide.

2. The system of claim 1, wherein the retainers can be deployed into the anatomical structure or lumen upon compression of the resilient layer.

3. The system of claim 2, wherein the retainers can be retracted out of the anatomical structure or lumen such that the implantable device can be repositioned.

4. The system of claim 1, wherein the implantable device is constructed so that it conforms to a surface of the anatomical structure or lumen when attached to the anatomical structure or lumen.

5. The system of claim 1, wherein the attachment mechanism is configured to attach the implantable device to the anatomical structure or lumen in a minimally invasive manner.

6. The system of claim 1, wherein at least one of the retainers includes a barb adapted to engage the anatomical structure or lumen.

7. The system of claim 1, wherein the attachment mechanism is contained in a lower compartment adjacent the implantable device.

8. The system of claim 1, wherein the resilient layer comprises a foam layer.

9. The system of claim 1, wherein the retainers are pre-stressed, whereby the retainers assume a spiral shape when extending outwardly beyond the second surface of the resilient layer.

10. The system of claim 9, wherein the at least one of the retainers includes a barb adapted to engage the anatomical structure or lumen.

11. An implantable device system for controlling at least one of a shape and size of an anatomical structure or lumen, comprising:
- an adjustable implantable device adapted to adjust at least one of the shape and size of an anatomical structure or lumen;
- an adjustment tool configured to be coupled to the implantable device for adjusting at least one of a shape and size of the implantable device; and
- an attachment assembly coupled to the implantable device, the attachment assembly comprising a resilient layer having first and second opposing surfaces, a moveable retainer ring guide supported on the first surface of the resilient layer adjacent the adjustable implantable device, a plurality of retainers attached to the retainer ring guide and extending into the resilient layer, whereby compression of the resilient layer by movement of the retainer ring guide causes an end portion of the retainers to extend outwardly beyond the second surface of the resilient layer, and a rigid retainer guide positioned adjacent the second surface of the resilient layer for receiving an end of one of the retainers, the retainer guide configured as a stop member for limiting a distance between the second surface of the resilient layer and the retainer ring guide upon compression of the resilient layer by the retainer ring guide.

12. The system of claim 11, wherein at least one of the retainers includes a barb adapted to engage the anatomical structure or lumen.

13. The system of claim 11, wherein the resilient layer comprises a foam layer.

* * * * *